US008865763B2

(12) United States Patent
Lyons et al.

(10) Patent No.: US 8,865,763 B2
(45) Date of Patent: Oct. 21, 2014

(54) METHODS AND COMPOSITIONS FOR ALTERING CELL FUNCTION

(75) Inventors: Thomas P. Lyons, Nicholasville, KY (US); Ronan Power, Lexington, KY (US)

(73) Assignee: Alltech, Inc., Nicholasville, KY (US)

( * ) Notice: Subject to any disclaimer, the term of this patent is extended or adjusted under 35 U.S.C. 154(b) by 784 days.

(21) Appl. No.: 11/581,282

(22) Filed: Oct. 16, 2006

(65) Prior Publication Data
US 2007/0122491 A1    May 31, 2007

Related U.S. Application Data

(60) Provisional application No. 60/726,951, filed on Oct. 14, 2005.

(51) Int. Cl.
| A61K 31/28 | (2006.01) |
| A61K 33/04 | (2006.01) |
| A61K 38/28 | (2006.01) |
| A61K 45/06 | (2006.01) |
| A61K 33/24 | (2006.01) |
| A61K 31/426 | (2006.01) |
| A61K 31/155 | (2006.01) |
| A61K 31/17 | (2006.01) |

(52) U.S. Cl.
CPC ............... *A61K 33/04* (2013.01); *A61K 38/28* (2013.01); *A61K 45/06* (2013.01); *A61K 33/24* (2013.01); *A61K 31/426* (2013.01); *A61K 31/155* (2013.01); *A61K 31/17* (2013.01)
USPC .......................................... 514/492; 424/702

(58) Field of Classification Search
None
See application file for complete search history.

(56) References Cited

U.S. PATENT DOCUMENTS

| 5,116,624 | A | 5/1992 | Horrobin et al. |
| 5,221,545 | A | 6/1993 | Borschel |
| 5,497,666 | A | 3/1996 | Patten et al. |
| 5,734,112 | A | 3/1998 | Bose et al. |
| 6,092,429 | A | 7/2000 | Cunningham et al. |
| 6,197,295 | B1 | 3/2001 | Hsia |
| 6,412,354 | B1 | 7/2002 | Birchak et al. |
| 6,576,233 | B2 | 6/2003 | Hsia |
| 6,911,550 | B2 | 6/2005 | Abdel-Monem |
| 7,168,329 | B2 | 1/2007 | Bell et al. |
| 7,275,448 | B2 | 10/2007 | Bitto et al. |
| 2001/0043925 | A1 | 11/2001 | Hsia |
| 2003/0036079 | A1 | 2/2003 | Weindruch et al. |
| 2005/0069594 | A1 | 3/2005 | Lubinski |
| 2005/0089530 | A1 | 4/2005 | Moesgaard |
| 2007/0077238 | A1 | 4/2007 | Teo et al. |

FOREIGN PATENT DOCUMENTS

| CA | 2325041 | 5/2002 |
| CN | 1403017 | 10/2002 |
| CN | 1440665 A | 9/2003 |
| CN | 1569123 | 1/2005 |
| DE | 4413839 C1 | 10/1995 |
| EP | 0345247 | 12/1989 |
| EP | 0440341 | 12/1993 |
| FR | 2774596 | 8/1999 |
| JP | H07-033655 | 2/1995 |
| JP | 09-323939 | 12/1997 |
| JP | 2002-513383 | 11/1998 |
| JP | 2-32015 A | 2/1999 |
| JP | 2000-516606 | 2/1999 |
| JP | H11-199599 | 7/1999 |
| JP | 2001-027648 | 1/2001 |
| JP | 2005-511063 | 6/2003 |
| JP | 2005-525329 | 8/2003 |
| JP | 2004-344079 | 12/2004 |
| TW | 200404558 A | 4/2004 |
| WO | 9940911 A | 8/1999 |
| WO | 00/12102 | 3/2000 |
| WO | 0059936 | 10/2000 |
| WO | 03034837 | 1/2003 |
| WO | 03/050249 | 6/2003 |
| WO | 03066071 | 8/2003 |
| WO | 03/078605 | 9/2003 |
| WO | 03101380 | 11/2003 |
| WO | 2005/055996 | 6/2005 |
| WO | 2005/065069 | 7/2005 |
| ZA | 9904296 | 4/1998 |

OTHER PUBLICATIONS

Stranges et al., Effects of Long-Term Selenium Supplementation on the Incidence of Type 2 Diabetes, Annals of Internal Medicine (2007), vol. 147, pp. 217-223.*
Search Report for Taiwan Patent Application No. 094138021 dated Apr. 25, 2008.
Takashima et al., "tau protein kinase I is essential for amyloid β-protein-induced neurotoxicity" PNAS, 1993, 90: pp. 7789-7793.
Apostolski S. et al., "Glutathione Peroxidase in Amyotrophic Lateral Sclerosis: The Effects of Selenium Supplementation" 1998, Journal of Environmental Pathology, Toxicology and Oncology, pp. 325-329.
Database WPI Section Ch, Week 200346 Derwent Publications Lts, London GB; AN 2003-483169 XP002391876, Mar. 19, 2003.
Database WPI Section Ch, Week 200382 Derwent Publications Ltd., London, GB; AN 2003-878187 XP002367269 & CN 1 440 665 A (Dairy Ind Branch Ningxia Changning Ind G) Sep. 10, 2003.

(Continued)

*Primary Examiner* — Abigail Fisher
*Assistant Examiner* — Frank Choi
(74) *Attorney, Agent, or Firm* — Valerie L. Calloway; Merchant & Gould PC

(57) ABSTRACT

The present invention relates to compositions and methods for altering cell function. In particular, the present invention provides compositions comprising selenium (e.g., SEL-PLEX) and methods of using the same (e.g., as a therapeutic and/or prophylactic treatment for neurodegenerative disease). Additionally, the present invention demonstrates that specific forms of selenium (e.g., SEL-PLEX) possess the ability to alter expression of genes associated with disease and/or aging while other forms of selenium (e.g., selenomethionine) do not.

6 Claims, 4 Drawing Sheets

(56) References Cited

OTHER PUBLICATIONS

Database WPI Section Ch, Week 200501 Derwent Publications Ltd., London, GB; AN 2005-004594 XP002391875 & JP 2004344079 (Sety Co. Ltd) Dec. 9, 2004.
De Lustig et al, Peripheral Markers and Diagnostic Criteria in Alzheimer's Disease: Critical Evaluations, Rev in Neurosciences, 1994, 5: 213-225.
Douillet C et al. "Selenium in Diabetes: Effects of Selenium on Nephropathy in Type I Streptozocin-Induced Diabetic Rats" 1999 Journal of Trace Elements in Experimental Medicine Wiley-Liss, pp. 379-392 Abstract.
Douillet C. et al., "Effect of Selenium and Vitamin E Supplements on Tissue Lipids, Peroxides, and Fatty Acid Distribution in Experimental Diabetes" Lipids, Champaign IL vol. 33, No. 4, 1998 pp. 393-399.
Elvers et al., TGF-β2 neutralization inhibits proliferation and activates apoptosis of cerebellar granule cell precurors in the developing cerebellum, Mechanisms of Development, Dec. 15, 2004, 122, pp. 587-602.
Gray et al., Is Antioxidant Use Protective of Cognitive Function in the Community-Dwelling Elderly?, Am J Geriatric Pharacotherapy, 2003; 1: 3-10.
Hou, Inhibitory Effect of Selenite and Other Antioxidants on Complement-Mediated Tissue Injury in Patients with Epidemic Hemorrhagic Fever, Biological Trace Element Research, 1997; 56: 125-130.
Lee et al, Gene-expression profile of the ageing brain in mice, Nature Genetics, 25, 294-297 (2000).
McGeer et al., Inflammatory processes in Alzheimer's disease, Progress in Neuro-Psychopharmacology & Biological Psychiatry, 2003; 27: 741-749.
Rayman, The use of high-selenium yeast to raise selenium status: how does it measure up?, British Journal of Nutrition (2004), 92, 557-573.
Small et al, Cerebral metabolic and cognitive decline in persons at genetic risk for Alzheimer's disease, Proc Natl Acad Sci USA, 2000, 97: 6037-6042.
Vickers, A Vaccine Against Alzheimer's Disease, Drug Aging, 2002, 19(7): 487-494.
Website article at: medicalnewstoday.com/article /147201.php; downloaded Apr. 29, 2009, 2 pages.
Website publication at: alz.org/national/documents/ report_alzfactsfigures2009. Pdf; downloaded Apr. 29, 2009, 80 pages.
Webster et al., Structural and functional evidence for microglial expression of C1qRp the C1q receptor that enhances phagocytosis, Journal of Leukocyte Biology; 2000; 67: 109-116.
Winblad and Jelic, Treating the full spectrum of dementia with memantine, Int J Geratr Psychiatry, 2003; 18: S41-S46.
Yasojima et al., High stability of mRNAs postmortem and protocols for ther assessment by RT-PCT, Brain Res. Protocols, 2001; 67: 212-218.
Lovell et al., Organoselenium (Sel-Ples diet) decreases amyloid burden and RNA and DNA oxidative damage in APP/PS1 mice, Free Radical Biology & Medicine, 46, pp. 1527-1533, 2009.
Jang et al., Comparison the SE Bioavailability of Organic SE Sources in Growing-Finishing PIG, AAAP Animal Science Congress 2006 Korea.
Jang et al. Efficacy of three organic selenium sources for growing-finishing pigs 2008 Trace Elements in Animal Production Systems p. 264.
Suhajda et al. Preparation of selenium yeasts. I : Preparation of selenium-enriched *Saccharomyces cerevisiae* 2000 Journal of trace elements in medicine and biology vol. 14 No. 1 pp. 43-47.
Barger et al. Differential Biological Effects of Sodium Selenite, Selenomethionine and Yeast-derived Selenium in the Mouse unpublished.
Farkas et al., Transofrming Growth Factor-βs Are Essential for the Development of Midbrain Dopaminergic Neurons In Vitro and In Vivo, The Journal of Neuroscience, Jun. 15, 2003, 23(12), pp. 5178-5186.

Sakamoto et al., Adenoviral Gene Transfer of GDNF, BDNF and TGFβ2, but not CNTF, Cardiotrophin-1 or IGF1, Protects Injured Adult Motoneurons After Facial Nerve Avulsion, Journal of Neuroscience Research, 2003, 72, pp. 54-64.
Arthur, "The glutathione peroxidases"; Cell. Mol. Life Sci., 57:1825-1835 (2000).
Bedwal et al., "Selenium—Its Biological Perspectives"; Medical Hypotheses; 41(2):150-159 (1993).
Blumenthal, "Fidelity assurance mechanisms of the brain with special reference to its immunogenic CNS compartment: Their role in aging and aging-associated neurological disease"; J. Gerontol. Biol Sci. Med., 52A(1):B1-B9 (1997).
Bonifati et al., "Mutations in the DJ-1 gene associated with autosomal recessive early-onset Parkinsonism"; Science, 299(5604):256-259 (2003).
Borchelt et al., "Accelerated amyloid deposition in the brains of transgenic mice coexpressing mutant Presenilin 1 and amyloid precursor proteins"; Neuron, 19:939-945 (1997).
Brooks et al., "Plasma Selenium level before diagnosis and the risk of prostate cancer development"; J Urol., 166:2034-2038 (2001).
Bush et al., "A novel Zinc(II) binding site modulates the function of the βA4 amyloid protein precursor of Alzheimer's disease"; J. Biol. Chem., 268:16109-16112 (1993).
Bush, "Rapid induction of Alzheimer Aβ amyloid formation by zinc"; Science, 265:1464-1467 (1994).
Bush, "Metal complexing agents as therapies for Alzheimer's disease"; Aging, 23:1031-1038 (2002).
Bush et al., "Copper, zinc, and the metallobiology of Alzheimer disease"; Alzheimers Dis. Assoc. Disorder; 7:147-150 (2003).
Chapman et al., "Impaired synaptic plasticity and learning in aged amyloid precursor protein transgenic mice"; Nat. Neurosci., 2(3):271-276 (1999).
Cherny et al., "Treatment with a copper-zinc chelator markedly and rapidly inhibits β-amyloid accumulation in Alzheimer's disease transgenic mice"; Neuron, 30:665-676 (2001).
Chung et al., "S-nitrosylation of Parkin regulates ubiquitination and compromises Parkin's protective function" Science, 304:1328-1331 (2004).
Clark et al., "Effects of selenium supplementation for cancer prevention in patients with Carcinoma of the skin: A randomized controlled trial"; J. Am. Med. Assoc., 276(24): 1957-1963, (1996).
Clement et al, "Effects of selenium on 7,12-dimethylbenz(A)anthracene-induced mammary carcinogenesis and DNA adduct formation"; Cancer Res., 45:61-65 (1985).
Clement, "Lessons from basic research in selenium and cancer prevention"; J. Nutr, 128:1845-1854 (1998).
Coyle, "Oxidative stress, glutamate, and neurodegenerative disorders"; Science, 262(5134):689-695 (1993).
Crochemore et al., "Disease-related regressive alterations of forebrain cholinergic system in SOD1 mutant transgenic mice", NeuroChem Int, 46(5):357-368 (2005).
De Strooper et al., "Deficiency of presenilin-1 inhibits the normal cleavage of amyloid precursor protein"; Nature, 391:387-390 (1998).
Deleve et al., "Glutathione metabolism and its role in hepatotoxicity"; Pharmac. Ther., 52:287-305 (1991).
Dong et al., "Metal binding and oxidation of amyloid-β within isolated senile plaque cores: Raman microscopic evidence"; Biochemistry, 42:2768-2773 (2003).
Duan et al; "Mattson, dietary restriction and 2-deoxyglucose administration improve behavioral outcome and reduce degeneration of dopaminergic neurons in models of Parkinson's disease"; J. Neurosci. Res., 57:195-206 (1999).
Edbauer et al., "Reconstitution of gamma-secretase activity", Nat. Cell Biol., 5:486-488 (2003).
Fairris et al., "The effect of supplementation with selenium and vitamin E in psoriasis"; Ann Clin Biochem., 26 (1):83-88 (1989).
Furnsinn et al., "Improved glucose-tolerance by acute vanadate but not by selenite exposure in genetically-obese rats (FA/FA)"; Int. J. of Obesity and Related Matab. Dis., 19(7):458-463 (1995).
Gafni, "Inhibition of calpain cleavage of Huntingtin reduces toxicity: Accumulation of calpain/caspase fragments in the nucleus"; J. Biol Chem, 279(19):20211-20220 (2004).

(56) References Cited

OTHER PUBLICATIONS

Garland et al., "Antioxidant micronutrients and breast-cancer"; J. Am. Coll. Nutr., 12(4):400-411 (1993).
Gerloff et al., "Effect of Selenium Supplementation on Dairy Cattle"; J. Anim. Sci., 70:3934-3940 (1992).
Ghadirian et al., "A case-control study of toenail selenium and cancer of the breast, colon, and prostate"; Cancer Detect Prey 24(4):305-313 (2000).
Goehring et al., "Effects of seleniferous grains and inorganic selenium on tissue and blood composition and growth-performance of rats and swine"; J. Anim. Sci. 59:725-732 (1984).
Gradwohl et al., "Neurogenin3 is required for the development of the four endocrine cell lineages of the pancreas"; PNAS, 97(4):1607-1611 (2000).
Haass et al., "Alzheimer disease γ-secretase: a complex story of GxGD-type presenilin proteases"; Trends Cell Biol., 12(12):556-562 (2002).
Haass, "Take five—BACE and the γ-secretase quartet conduct Alzheimer's amyloid β-peptide generation" Embo J., 23:483-488 (2004).
Hayes et al., "Glutathione Transferases"; Annu. Rev. Phramacal Toxicol, 45:51-88 (2005).
Hardy et al., "Genes and parkinsonism"; Lancet Neurol, 2(4):221-228 (2003).
Heremans et al., "Recapitulation of embryonic neuroendocrine differentiation in adult human pancreatic duct cells expressing neurogenin 3"; the Journal of Cell Biology, 159(2):303-311 (2002).
Hough et al., "Dimer destabilization in superoxide dismutase may result in disease-causing properties: Structures of motor neuron disease mutants"; PNAS, 101(16):5976-5981 (2004).
Huang et al., "Neuronal Protection in Stroke by an sLex-Glycosylated Complement Inhibitory Protein"; Science, 285:595-599 (1999).
Huang et al., "The Aβ peptide of Alzheimer's disease directly produces hydrogen peroxide through metal ion reduction"; Biochemist, 38:7609-7616 (1999).
Hutton et al., Genetics of Alzheimer's disease; Essays Biochem, 33:117-131 (1998).
Ingram et al., "Dietary restriction benefits learning and motor performance of aged mice" J. Gerontol, 42(1):78-81 (1987).
Jenny et al., "Neurogenin3 is differentially required for endocrine cell fate specification in the intestinal and gastric epithelium"; The Embo Journal, 21(23):6338-6347 (2002).
Jin et al., "Expression of calsenilin in neurons and astrocytes in the Alzheimer's disease brain"; Neuroreport, 16 (5):451-455 (2005).
Jo et al., "Overexpression of calsenilin enhances γ-secretase activity"; Neurosci Lett, 378:59-64, (2005).
Kawahara et al., "Glutamate receptors: RNA editing and death of motor neurons"; Nature, 427:801 (2004).
Kitada et al., "Mutations in the parkin gene cause autosomal recessive juvenile parkinsonism"; Nature, 392:605-608 (1998).
Koo et al., "Amyloid diseases: Abnormal protein aggregation in neurodegeneration"; PNAS USA, 96:9989-9990 (1999).
Larsen et al., "Nutritional and hormonal regulation of Thyroid hormone deiodinases"; Annu Rev Nutr., 15:323 (1995).
Lee et al., "Neurogenin 3 is essential for the proper specification of gastric enteroendocrine cells and the maintenance of gastric epithelial cell identity"; Genes Dev., 16:1488-1497 (2002).
Lemere et al., "The Lysosomal Cysteine Protease, Cathepsin S, is Increased in Alzheimer's Disease and Down Syndrome Brain"; Am J Pathol 146(4):646-666 (1995).
Lemere et al., "The AMY antigen co-occurs with Aβ and follows its deposition in the amyloid plaques of Alzheimer's disease and Down Syndrom"; 155(1):29-37 (1999).
Lipton, "Sporadic ALS: blame it on the editor"; Nat Med 10(4):347 (2004).
Lovell et al., "Copper, iron and zinc in Alzheimer's disease senile plaques"; J. Neurol. Sci., 158:47-52, 1998.
Mahan, "Organic selenium: using nature's model to redefine selenium supplementation for animals"; Biotechnology in the Feed Industry, Proceedings of Alltech's Fiftheenth Annual Symposium, Nottingham University Press, pp. 523-535 (1999).
McEwen, "Stress and the aging hippocampus"; Fron. Neuroendocrin; 20:49-70 (1999).
Meister et al., "Glutathione" Annu. Rev. Bio Chem, 52:711-760(1983).
Milligan, "Caspase cleavage of APP results in a cytotoxic proteolytic peptide"; Nat. Med. 6(4):385-386 (2000).
Morgan et al., "Complement central to innate immunity and bridging to adaptive responses"; Immunol Lett., 97:171 (2005).
Mori et al., "The LIM homeobox gene, L3/Lhx8, is necessary for proper development of basal forebrain cholinergic neurons"; Eur. J. Neurosci., 19:3129-3141 (2004).
Moroi-Fetters et al., "Dietary restriction suppresses age-related-changes in dendritic spines"; Neurobiology of Aging , 10:317-322 (1989).
Morrison et al.; "Life and death of neurons in the aging brain"; Science, 278:412-419 (1997).
Opazo et al., "Metalloenzyme-like activity of Alzheimer's disease beta-amyloid. Cu-dependent catalytic conversion of dopamine, cholesterol, and biological reducing agents to neurotoxic $H(2)O(2)$"; J. Biol Chem, 277(43):40302-40308 (2002).
Palmer et al., "Reactive oxygen species and antioxidants in signal transduction and gene expression"; Nutr. Rev., 55 (10):353-361 (1997).
Pasinetti et al.,"Glial gene expression during aging in rat striatum and in long-term responses to 6-OHDA lesions"; Synapse 31(4):278-284 (1999).
Peinado et al., "Light microscopic quantification of morphological changes during aging in neurons and glia of the rat parietal cortex"; Anat Rec, 247:420-425 (1997).
Polymeropoulos et al., "Mutation in the α-synuclein gene identified in families with Parkinson's disease"; Science, 276:2045-2047 (1997).
Rao et al., "Gene expression profiling of low selenium status in the mouse intestine: Transcriptional activation of genes linked to DNA damage, cell cycle control and oxidative stress"; Am Society of Nutr Sci, pp. 3175-3181 (2001).
Ray et al., "A possible therapeutic target for Lou Gehrig's disease"; PNAS USA, 101(16):5701-5702 (2004).
Rayman, "The importance of selenium to human health"; Lancet, 356: 233-241 (2000).
Rosen et al., "Mutations in Cu/Zn superoxide dismutase gene are associated with familial amyotrophic lateral sclerosis"; Nature, 362:59-62 (1993).
Roses, "Apolipoprotein E in neurology"; Curr Opin Neurol 9(4):265-270 (1996).
Rukstalis et al., "Neurogenin3: A master regulator of pancreatic islet differentiation and regeneration"; Islets 1 (3):177-184 (2009).
Salonen et al., "Association between serum selenium and the risk of cancer"; American J. Epidemiology, 120 (3):342-349 (1984).
Schwab et al., "Complement activated C4d immunoreactive oligodendrocytes delineate small cortical plaques in Multiple Sclerosis"; Experimental Neurology, 174(1):81-88 (2002).
Selkoe, "Folding proteins in fatal ways"; Nature, 426:900-904 (2003).
Sohal et al, "Oxidative stress, caloric restriction, and aging"; Science, 273:59-63 (1996).
Stewart et al., "Risk of Alzheimer's disease and duration of NSAID use"; Neurology, 48:626-632 (1997).
Subramaniam et al., "Mutant SOD1 causes motor Neuron Disease Independent of Copper Chaperone—Mediated Copper Loading"; Nat. Neurosci., 5(4):301-307 (2002).
Turner et al, "Impaired extracellular secretion of mutant superoxide dismutase 1 associates with neurotoxicity in familial amyotrophic lateral sclerosis"; J. Neurosci, 25:108-117 (2005).
Valente et al., "Hereditary early-onset Parkinson's disease caused by mutations in PINK1"; Science, 304 (5674):1158-1160 (2004).
Villiers et al., "Complement receptors and B lymphocytes"; Crit Rev Immunol, 24(6):465-478 (2004).
Virtamo et al., "Serum selenium and risk of cancer: A prospective follow-up of nine years"; Cancer, 60:145-148 (1987).

(56) References Cited

OTHER PUBLICATIONS

Walsh et al., "Naturally secreted oligomers of amyloid β protein potently inhibit hippocampal long-term potentiation in vivo"; Nature, 416:535-539 (2002).

Watada, "Neurogenin 3 is a key transcription factor for differentiation of the endocrine pancreas"; Endocrine J, 51 (3):255-264 (2004).

Weggen et al., "A subset of NSAIDs lower amyloidogenic Abeta42 independently of cyclooxygenase activity"; Nature, 414:212-216 (2001).

Willett et al., "Prediagnostic serum selenium levels and risk of cancer"; Lancet, 322(8342):130-134 (1983).

Xu et al., "Dopamine-dependent neurotoxicity of α-synuclein: A mechanism for selective neurodegeneration in Parkinson disease"; Nature Medicine, 8(6):600-606 (2002).

Yasojima et al., "Up-regulated production and activation of the complement system in Alzheimer's disease brain"; Am J Pathology, 154(3):927-936 (Mar. 1999).

Yechoor et al., "Neurogenin3 is sufficient for in vivo transdetermination of hepatic progenitor cells into islet-like cells but not transdifferentiation of hepatocytes"; Dev Cell., 16(3):358-373 (2009).

Yechoor et al., "Gene therapy with neurogenin 3 and betacellulin reverses major metabolic problems in insulin-deficient diabetic mice"; Endocrinology 150(11):4863-4873 (2009).

Yoshizawa et al., "Study of prediagnostic selenium level in toenails and the risk of advanced prostate cancer"; J Natl Cancer Inst., 90(16):1219-1224, (1998).

Yu et al., "Protective role of selenium against Hepatitis B virus and Primary Liver cancer in qidong"; Biol Trace Elem Res, 56:117-124 (1997).

Zhao et al., "The LIM-homeobox gene Lhx8 is required for the development of many cholinergic neurons in the mouse forebrain"; PNAS 100(15):9005-9010 (2003).

* cited by examiner

METHODS AND COMPOSITIONS FOR ALTERING CELL FUNCTION

This invention claims priority to U.S. Provisional Patent Application No. 60/726,951, filed Oct. 14, 2005, the entire contents of which are herein incorporated by reference.

FIELD OF THE INVENTION

The present invention relates to compositions and methods for altering cell function. In particular, the present invention provides compositions comprising selenium (e.g., SEL-PLEX) and methods of using the same (e.g., as a therapeutic and/or prophylactic treatment for neurodegenerative disease). Additionally, the present invention demonstrates that specific forms of selenium (e.g., SEL-PLEX) possess the ability to alter expression of genes associated with disease and/or aging.

BACKGROUND OF THE INVENTION

Selenium is a trace element important for proper physiological function in humans. Selenium is ingested through the diet which can have a varying content of selenium. For example, in large parts of the world, crops with poor levels of selenium are cultivated because of low levels of selenium in the soil.

Selenium is incorporated into different organic molecules including, for example, amino acids such as 1-selenomethionine, selenocysteine, and selenocystine. Thus, selenium can be a component part of proteins, many of which are of structural importance to the body. Furthermore, selenium is an important ingredient in a number of enzymes which influence metabolism, reproduction, the prevention of cancer, and immune defense in humans (See, e.g., Rayman, M, Lancet 356:233-241 (2000)).

Multiple forms of selenium have been examined. These include inorganic selenium such as selenite, and organic sources, including selenium yeast. There is a significant difference between absorption and toxicity of inorganic and organic selenium, the inorganic compounds usually being absorbed and utilized less efficiently and also being more toxic than organic sources of selenium.

Multiple studies have attempted to reveal potential health benefits resulting from the ingestion of low levels of selenium. For example, low concentrations of an inorganic form of selenium, sodium selenate, have shown some potential health benefits (See, e.g., Furnsinn et al., Int. J of Obesity and Related Metab. Dis., 19, 458-463 (1995)). However, at elevated dosage levels, beneficial effects are reversed and dangerous toxicity is manifested.

Research over the last two decades has suggested that selenium is effective in the reduction of cancer incidence when provided to animals at doses only 5- to 10-fold above nutritional requirement (See, e.g., El-Bayoumy, The role of selenium in cancer prevention, Philadelphia, Lippincott, 1-15, 1991). Chemoprevention studies with selenium in animal model systems have indicated that this element is effective for most, if not all of the organ systems and is protective against the carcinogenic effects of a wide variety of insults (See, e.g., El-Bayoumy, The role of selenium in cancer prevention, Philadelphia, Lippincott, 1-15, 1991). Both epidemiological studies and supplementation trials have also supported its efficacy in lowering the incidence of cancers of the liver, colon, prostate and lung (See, e.g., Yu et al. Biol Trace Elem Res, 56: 117-124 (1997); Clark et al., J Am Med Assoc, 276: 1957-1963 (1996); Yoshizawa et al., J Natl Cancer Inst, 90: 1219-1224, (1998); Brooks, et al., J Urol, 166: 2034-2038, (2001)). Other studies have demonstrated no beneficial effect for selenium reduction of cancers (See, e.g., Garland et al., J. Am. Coll Nutr., 12: 400-11 (1993); Ghadirian et al., Cancer Detect Prev, 24: 305-13 (2000)).

Heart disease has also been shown to be reduced in persons who consume certain amounts of selenium in their diet. The levels of selenium in the blood stream were correlated with the degree of progression of cardiovascular disease with those patients having the lowest levels of selenium having the most extensive coronary artery blockage A need exists to identify new targets for selenium treatment that provide beneficial effects to a subject. Additionally, there is a need for information regarding what forms of selenium can and cannot be used for bringing about these effects. For example, it would be of great value to elucidate various ways in which different forms of selenium (e.g., organic, inorganic, or both) might be used to benefit certain systems (e.g., nervous, endocrine, and metabolic systems) of a subject (e.g., a human, bovine or other mammal). Furthermore, understanding how various forms of selenium differ in their ability to exert effects on a subject provides the ability to customize treatments for subjects suffering from, or at risk of, a disease or disorder that might be benefited by such treatment (e.g., specific forms of selenium could be used independently or with other known agents to treat or prevent diseases or disorders). Identification of unwanted effects from the consumption of certain forms of selenium could also be identified and avoided.

SUMMARY OF THE INVENTION

The present invention relates to compositions and methods for altering cell function. In particular, the present invention provides compositions comprising selenium (e.g., SEL-PLEX) and methods of using the same (e.g., as a therapeutic and/or prophylactic treatment for neurodegenerative disease). Additionally, the present invention demonstrates that specific forms of selenium (e.g., SEL-PLEX) possess the ability to alter expression of genes associated with disease and/or aging while other forms of selenium (e.g., free selenomethionine) do not. Accordingly, the present invention provides a method of treatment or preventative for Alzheimer's or reduction of signs or symptoms associated with Alzheimer's disease or prophylactically preventing or minimizing biological events associated with the onset or progression of Alzheimer's or reducing gene expression of genes correlated to the onset or progression of Alzheimer's disease comprising administering to a subject (e.g., a subject suffering from Alzheimer's disease, a subject with early-onset Alzheimer's disease, a subject having Alzheimer's disease, a subject displaying signs or symptoms or pathology indicative of Alzheimer's disease, a subject suspected of having Alzheimer's disease, a subjects suspected of displaying signs or symptoms or pathology indicative of Alzheimer's disease, a subject at risk of Alzheimer's disease (e.g., a subject predisposed (e.g., with a family history or genetically (e.g., possessing an APO E variant) etc.), a subject at risk of displaying pathology indicative of Alzheimer's disease, an animal model of Alzheimer's disease, or a healthy subject wishing to reduce risk of Alzheimer's disease) a composition comprising selenium (e.g., organic selenium (e.g., selenized yeast (e.g., SEL-PLEX))) under conditions such that the expression of a complement gene is reduced (e.g., in the cerebral cortex) in the subject or under conditions such that one or more signs or symptoms of Alzheimer's disease is reduced or eliminated or that onset or progression of Alzheimer's disease is delayed or prevented. In some embodiments, the treatment is prophylactic. In some embodiments, the complement gene expression is age related. In some embodiments, the complement gene is C1q, C1q alpha, C1q beta, C1q gamma, C1qr or other complement gene. In some embodiments, the prophylactic treatment prevents the onset of signs and symptoms of Alzheimer's disease in the subject. In some embodiments, the composition comprising selenium (e.g., organic selenium (e.g., selenized yeast (e.g., SEL-PLEX))) comprises one or more other forms of selenium. The present invention is not limited by the type of selenium co-administered. Indeed, a variety of forms of selenium are contemplated to be useful in co-administration including, but not limited to, selenomethionine, selenocysteine, a selenite compound, a selenate compound, or derivatives, salts, or modifications thereof. In some embodiments, providing selenium (e.g., organic selenium (e.g., selenized yeast (e.g., SEL-PLEX))) and one or more different forms of selenium provides an additive reduction in the expression of a complement gene. In some embodiments, providing selenium (e.g., organic selenium (e.g., selenized yeast (e.g., SEL-PLEX))) and one or more different forms of selenium provides a synergistic (e.g., more than additive) reduction in the expression of a complement gene. In some embodiments, providing selenium (e.g., organic selenium (e.g., selenized yeast (e.g., SEL-PLEX))) and one or more different forms of selenium provides altered (e.g., reduced) expression of more genes than are altered (e.g., reduced) with either form of selenium alone. In some embodiments, the composition comprising selenium (e.g., organic selenium (e.g., selenized yeast (e.g., SEL-PLEX))) is co-administered with an antioxidant. The present invention is not limited by the antioxidant used. Indeed, a variety of antioxidants are contemplated to be useful for co-administration with selenium (e.g., organic selenium (e.g., selenized yeast (e.g., SEL-PLEX))) including, but not limited to, alkylated diphenylamines, N-alkylated phenylenediamines, phenyl-α-naphthylamine, alkylated phenyl-α-naphthylamine, dimethyl quinolines, trimethyldihydroquinolines, hindered phenolics, alkylated hydroquinones, hydroxylated thiodiphenyl ethers, alkylidenebisphenols, thiopropionates, metallic dithiocarbamates, 1,3,4-dimercaptothiadiazole, an oil soluble copper compound, NAUGALUBE 438, NAUGALUBE 438L, NAUGALUBE 640, NAUGALUBE 635, NAUGALUBE 680, NAUGALUBE AMS, NAUGALUBE APAN, Naugard PANA, NAUGALUBE TMQ, NAUGALUBE 531, NAUGALUBE 431, NAUGALUBE BHT, NAUGALUBE 403, NAUGALUBE 420, ascorbic acid, tocopherols, alpha-tocopherol, a sulfhydryl compound, sodium metabisulfite, N-acetyl-cysteine, lipoic acid, dihydrolipoic acid, resveratrol, lactoferrin, ascorbic acid, ascorbyl palmitate, ascorbyl polypeptide, butylated hydroxytoluene, retinoids, retinol, retinyl palmitate, tocotrienols, ubiquinone, a flavonoid, an isoflavonoid, genistein, diadzein, resveratrol, grape seed, green tea, pine bark, propolis, IRGANOX, Antigene P, SUMILIZER GA-80, beta-carotene, lycopene, vitamin C, vitamin E, and vitamin A. In some embodiments, the composition comprising selenium (e.g., organic selenium (e.g., selenized yeast (e.g., SEL-PLEX))) is co-administered with an Alzheimer's therapeutic. The present invention is not limited to any particular Alzheimer's therapeutic. Indeed, a variety of Alzheimer's therapeutics are contemplated to be useful in the present invention including, but not limited to, a NMDA antagonist, an AChE inhibitor, and a metal chelator. In some embodiments, the NMDA antagonist is memantine. In some embodiments, the AChE inhibitor is tacrine, donepezil, rivastigmine, or galantamine. In some embodiments, the metal chelator is clioquinol. In some embodiments, the clioquinol chelates zinc and copper.

The present invention also provides a method of treating a subject having Alzheimer's disease comprising administering to the subject a composition comprising selenium (e.g., organic selenium (e.g., selenized yeast (e.g., SEL-PLEX))) under conditions such that the expression of a gene (e.g., C1q, C1q alpha, C1q beta, C1q gamma, C1qr, Cathepsin B, Cathepsin D, Cathepsin Z, and Cathepsin O, calsenilin, presenilin 1, presenilin 2, nicastrin, Apbb1/Fe65, Aplp 1, and/or Apba1) is altered; and testing the expression of the gene. In some embodiments, the composition comprising selenium comprises SEL-PLEX. In some embodiments, testing the expression of the gene (e.g., presenilin 1 or presenilin 2) comprises use of an oligonucleotide probe. In some embodiments, testing the expression of a gene (e.g., presenilin 1 or presenilin 2) comprises use of PCR. In some embodiments, the PCR comprises RT-PCR. In some embodiments, testing is: before, during and/or after administration. In some embodiments, testing is for diagnostic uses. In some embodiments, testing is used for research uses.

The present invention also provides a method of treatment for Alzheimer's disease comprising administering to a subject a composition comprising selenium (e.g., organic selenium (e.g., selenized yeast (e.g., SEL-PLEX))) under conditions such that the expression of a cathepsin gene is reduced (e.g., in the cerebral cortex) in the subject. In some embodiments, the treatment is prophylactic. In some embodiments, the cathepsin gene expression is age related. In some embodiments, the cathepsin gene is Cathepsin B, Cathepsin D, Cathepsin Z, Cathepsin O or an other cathepsin gene. In some embodiments, reducing the expression of a cathepsin gene reduces processing of amyloid precursor protein (APP) to amyloid β-peptide. In some embodiments, reducing levels of the amyloid β-peptide reduces formation of Alzheimer's disease plaques in the brain of the subject. In some embodiments, the prophylactic treatment prevents the onset or progression of signs and symptoms of Alzheimer's disease in the subject.

The present invention also provides a method of treatment for Alzheimer's disease comprising administering to a subject a composition comprising selenium (e.g., organic selenium (e.g., selenized yeast (e.g., SEL-PLEX))) under conditions such that the expression of presenilin (e.g., presenilin 1 or presenilin 2) is reduced (e.g., in the cerebral cortex) in the subject. In some embodiments, the treatment is prophylactic. In some embodiments, the expression of presenilin is age related. In some embodiments, reducing the expression of presenilin reduces processing of amyloid precursor protein (APP) to amyloid β-peptide. In some embodiments, reducing levels of the amyloid β-peptide reduces formation of Alzheimer's disease plaques in the brain of the subject. In some embodiments, prophylactic treatment prevents the onset or progression of signs and symptoms of Alzheimer's disease in the subject.

The present invention also provides a method of treatment for Alzheimer's disease comprising administering to a subject a composition comprising selenium (e.g., organic selenium (e.g., selenized yeast (e.g., SEL-PLEX))) under conditions such that the expression of nicastrin is reduced (e.g., in the cerebral cortex) in the subject. In some embodiments, the treatment is prophylactic. In some embodiments, the expression of nicastrin is age related. In some embodiments, reducing the expression of nicastrin reduces processing of amyloid precursor protein (APP) to amyloid β-peptide. In some embodiments, reducing levels of the amyloid β-peptide reduces formation of Alzheimer's disease plaques in the brain of the subject. In some embodiments, prophylactic treatment prevents the onset or progression of signs and symptoms of Alzheimer's disease in the subject.

The present invention also provides a method of treatment for Alzheimer's disease comprising administering to a subject a composition comprising selenium (e.g., organic selenium (e.g., selenized yeast (e.g., SEL-PLEX))) under conditions such that the expression of nicastrin and/or calsenilin is reduced (e.g., in the cerebral cortex) in the subject. In some embodiments, the treatment is prophylactic. In some embodiments, the expression of nicastrin and/or calsenilin is age related. In some embodiments, reducing the expression of nicastrin and/or calsenilin reduces processing of amyloid precursor protein (APP) to amyloid β-peptide. In some embodiments, reducing levels of the amyloid β-peptide reduces formation of Alzheimer's disease plaques in the brain of the subject. In some embodiments, prophylactic treatment prevents the onset or progression of signs and symptoms of Alzheimer's disease in the subject.

The present invention also provides a method of inhibiting the expression of a gene involved in processing amyloid precursor protein in a subject comprising administering to the subject a composition comprising selenium (e.g., organic selenium (e.g., selenized yeast (e.g., SEL-PLEX))) under conditions such that the expression of a gene involved in processing amyloid precursor protein is reduced. In some preferred embodiments, the gene involved in processing amyloid precursor protein is C1q, C1q alpha, C1q beta, C1q gamma, C1qr, Cathepsin B, Cathepsin D, Cathepsin Z, and Cathepsin O, presenilin 1, presenilin 2, nicastrin, calsenilin, Apbb1/Fe65, Aplp 1, and/or Apba1. In some embodiments, the composition comprising selenium is administered to the subject as a prophylactic or therapeutic treatment for neurodegenerative disease. Methods of the present invention can be used to treat a variety of subjects, including, but not limited to a subject at risk of displaying pathology indicative of Alzheimer's disease and a subject having Alzheimer's disease. In some embodiments, the composition comprising selenium comprises SEL-PLEX. In some embodiments, the composition comprising SEL-PLEX comprises one or more other forms of selenium. In some embodiments, the composition comprising selenium is co-administered with an Alzheimer's therapeutic. In some embodiments, administering the composition comprising selenium inhibits the onset of Alzheimer's disease signs and symptoms in the subject. In some embodiments, the composition comprising selenium is co-administered with an antioxidant.

The present invention also provides a method of inhibiting the expression of a gene involved in the generation of β-amyloid peptide in a subject comprising administering to the subject a composition comprising selenium (e.g., organic selenium (e.g., selenized yeast (e.g., SEL-PLEX))) under conditions such that the expression of a gene involved in the generation of β-amyloid peptide is reduced. In some preferred embodiments, the gene involved in the generation of β-amyloid peptide is C1q, C1q alpha, C1q beta, C1q gamma, C1qr, Cathepsin B, Cathepsin D, Cathepsin Z, and Cathepsin O, presenilin 1, presenilin 2, calsenilin, nicastrin, Apbb1/Fe65, Aplp 1, and/or Apba1. In some embodiments, the composition comprising selenium is administered to the subject as a prophylactic or therapeutic treatment for neurodegenerative disease. Methods of the present invention can be used to treat a variety of subjects, including, but not limited to a subject at risk of displaying pathology indicative of Alzheimer's disease and a subject having Alzheimer's disease. In some embodiments, the composition comprising selenium comprises SEL-PLEX. In some embodiments, the composition comprising SEL-PLEX comprises one or more other forms of selenium. In some embodiments, the composition comprising selenium is co-administered with an Alzheimer's therapeutic. In some embodiments, administering the composition comprising selenium inhibits the onset of Alzheimer's disease signs and symptoms in the subject. In some embodiments, the composition comprising selenium is co-administered with an antioxidant.

The present invention also provides a composition comprising SEL-PLEX and an Alzheimer's therapeutic. In some embodiments, the Alzheimer's therapeutic is selected from the group consisting of a NMDA antagonist, an ACHE inhibitor, and a metal chelator. In some embodiments, the NMDA antagonist is memantine. In some embodiments, the ACHE inhibitor is tacrine, donepezil, rivastigmine, or galantamine. In some embodiments, the metal chelator is clioquinol.

The present invention also provides a composition comprising selenium, an Alzheimer's therapeutic, and an antioxidant. In some embodiments, the composition comprising selenium comprises SEL-PLEX. In some embodiments, the Alzheimer's therapeutic is selected from the group consisting of a NMDA antagonist, an ACHE inhibitor, and a metal chelator.

The present invention also provides a method of altering cognitive function or reducing signs or symptoms associated with a decline in cognitive function or prophylactically preventing or minimizing biological events associated with the onset of a decline in cognitive function or altering (e.g., enhancing or reducing) gene expression of genes correlated with an increase or decline in cognitive function in a subject (e.g., a subject suffering from a decline in cognitive function, a subject wishing to enhance cognitive function, a subject displaying signs or symptoms or pathology of a decline in cognitive function, a subject suspected of having a decline of cognitive function, a subject at risk for a decline in cognitive function (e.g., an elderly subject), or an animal model of cognitive function) comprising administering to the subject a composition comprising selenium (e.g., organic selenium (e.g., selenized yeast (e.g., SEL-PLEX))) under conditions such that the expression of Lhx8 is enhanced in the subject or under conditions such that one or more signs or symptoms of a decline in cognitive function is reduced or eliminated or that onset or progression of a decline of cognitive function is delayed or prevented. In some embodiments, the altering cognitive function inhibits decline of cognitive function of the subject. In some embodiments, inhibiting decline of cognitive function in the subject comprises promoting development of basal forebrain cholinergic neurons. In some embodiments, inhibiting decline of cognitive function in the subject comprises maintenance of basal forebrain cholinergic neurons. In some embodiments, the composition comprising selenium (e.g., organic selenium (e.g., selenized yeast (e.g., SEL-PLEX))) comprises one or more different forms of selenium. In some embodiments, the composition comprising selenium (e.g., organic selenium (e.g., selenized yeast (e.g., SEL-PLEX))) is co-administered with an antioxidant.

The present invention further provides a method of altering cognitive function in a subject comprising administering to the subject a composition comprising selenium (e.g., organic selenium (e.g., selenized yeast (e.g., SEL-PLEX))) under conditions such that the expression of TGFβ2 is enhanced in the subject. In some embodiments, altering cognitive function inhibits decline of cognitive function of the subject. In some embodiments, inhibiting decline of cognitive function in the subject comprises promoting neuronal proliferation in the subject. In some embodiments, the neuronal proliferation occurs in the cerebellum of the subject. In some embodiments, the composition comprising selenium (e.g., organic selenium (e.g., selenized yeast (e.g., SEL-PLEX))) comprises one or more other forms of selenium. In some embodiments, the composition comprising selenium (e.g., organic selenium (e.g., selenized yeast (e.g., SEL-PLEX))) is co-administered with an antioxidant.

The present invention also provides a prophylactic treatment for inhibiting decline of cognitive function in a subject comprising administering to a subject a composition comprising SEL-PLEX. In some embodiments, the composition comprising selenium (e.g., organic selenium (e.g., selenized yeast (e.g., SEL-PLEX))) is administered under conditions such that the expression of Lhx8 is enhanced in the subject. In some embodiments, enhanced expression of Lhx8 promotes development and/or maintenance of basal forebrain cholinergic neurons. In some embodiments, the composition comprising selenium (e.g., organic selenium (e.g., selenized yeast (e.g., SEL-PLEX))) is administered under conditions such that the expression of TGFβ2 is enhanced in the subject. In some embodiments, enhanced expression of TGFβ2 promotes neuronal proliferation in the subject. In some embodiments, the neuronal proliferation occurs in the cerebellum of the subject. In some embodiments, the composition comprising selenium (e.g., organic selenium (e.g., selenized yeast (e.g., SEL-PLEX))) comprises one or more other forms of selenium. In some embodiments, the composition comprising selenium (e.g., organic selenium (e.g., selenized yeast (e.g., SEL-PLEX))) is co-administered with an antioxidant. In some embodiments, the prophylactic treatment prevents (e.g., prevents the onset of, recurrence of, and/or ameliorates) signs and symptoms of Alzheimer's disease in the subject. In some embodiments, the prophylactic treatment prevents (e.g., prevents the onset of, recurrence of, and/or ameliorates) signs and symptoms of multiple sclerosis in the subject. In some embodiments, the prophylactic treatment prevents (e.g., prevents the onset of, recurrence of, and/or ameliorates) signs and symptoms of ALS in the subject. In some embodiments, the prophylactic treatment prevents (e.g., prevents the onset of, recurrence of, and/or ameliorates) signs and symptoms of Parkinson's disease in the subject. In some embodiments, the prophylactic treatment prevents (e.g., prevents the onset of, recurrence of, and/or ameliorates) signs and symptoms of Huntington's disease in the subject. In some embodiments, the composition comprising selenium (e.g., organic selenium (e.g., selenized yeast (e.g., SEL-PLEX))) is administered under conditions such that the expression of a complement gene is reduced. Multiple complement genes have been demonstrated to be reduced using the compositions and methods of the present invention including, but not limited to, C1q, C1q alpha, C1q beta, C1q gamma and C1qr.

The present invention is not limited by the amount of selenium (e.g., organic selenium (e.g., selenized yeast (e.g., SEL-PLEX))) administered to a subject. Indeed a variety of different doses are contemplated to be useful in the presenting invention. In some embodiments, the composition comprising selenium (e.g., organic selenium (e.g., selenized yeast (e.g., SEL-PLEX))) is administered to the subject so as to provide between 200-500 µg of selenium to the subject each day. In some embodiments, the composition comprising selenium (e.g., organic selenium (e.g., selenized yeast (e.g., SEL-PLEX))) is administered to the subject so as to provide between 300-600 µg of selenium to the subject each day. In other embodiments, the composition comprising selenium (e.g., organic selenium (e.g., selenized yeast (e.g., SEL-PLEX))) is administered to the subject so as to provide between 50 and 5000 µg of selenium to the subject each day. In some embodiments, a composition comprising two or more different forms of selenium (e.g., selonmethionine, Sod-sel and/or SEL-PLEX) is administered to a subject so as to provide the subject between 50 and 5000 µg of selenium each day.

The present invention also provides a method of altering age associated expression of a gene (e.g., a complement or cathepsin gene) or reducing signs or symptoms associated with age or prophylactically preventing or minimizing biological events associated with the aging process (e.g., a decline in cognitive function) or altering (e.g., enhancing or reducing) gene expression of genes correlated with an increase in age in a subject (e.g., a subject older than 16 years old, or a subject older than 25 years old, or preferably a subject older than 40 years old, or more preferably a subject older than 50, or even more preferably a subject older than 60 years old, or a subject suffering from a decline in cognitive function, or a subject displaying signs or symptoms or pathology (e.g., decline in cognitive function) of the aging process, an animal model of aging or a subject wishing to prevent the onset or progression of the aging process) in a subject comprising administering to the subject a composition comprising selenium (e.g., organic selenium (e.g., selenized yeast (e.g., SEL-PLEX))) under conditions such that age associated gene expression (e.g., complement or cathepsin genes) is reduced or under conditions such that one or more signs or symptoms of aging (e.g., a loss of cognitive function) is reduced or eliminated or that the onset or progression of the aging process is delayed or prevented. Many genes whose expression is altered (e.g., elevated) with age are contemplated to be altered (e.g., reduced) with compositions and methods of the present invention including, but not limited to, complement genes (e.g., C1q, C1q alpha, C1q beta, C1q gamma, and C1qr), cathepsin genes (e.g., Cathepsin B, Cathepsin D, Cathepsin Z, and Cathepsin O) junb and homeobox (Hox) transcription factor genes. In some embodiments, the composition comprising selenium (e.g., organic selenium (e.g., selenized yeast (e.g., SEL-PLEX))) is administered to the subject so as to provide between 200 and 500 µg of selenium to the subject each day. In some embodiments, the composition comprising selenium (e.g., organic selenium (e.g., selenized yeast (e.g., SEL-PLEX))) is administered to the subject so as to provide between 300 and 600 µg of selenium to the subject each day. In some embodiments, the composition comprising selenium (e.g., organic selenium (e.g., selenized yeast (e.g., SEL-PLEX))) comprises one or more different forms of selenium. In some embodiments, the one or more different forms of selenium comprises sodium-selenite. In some embodiments, the composition comprising selenium (e.g., organic selenium (e.g., selenized yeast (e.g., SEL-PLEX))) is co-administered with an Alzheimer's therapeutic. In some embodiments, administering the composition comprising selenium (e.g., organic selenium (e.g., selenized yeast (e.g., SEL-PLEX))) inhibits (e.g., prevents the onset of, recurrence of, and/or ameliorates) Alzheimer's disease signs and symptoms in the subject. In some embodiments, the composition comprising selenium (e.g., organic selenium (e.g., selenized yeast (e.g., SEL-PLEX))) is co-administered with an antioxidant. In some embodiments, the composition comprising selenium (e.g., organic selenium (e.g., selenized yeast (e.g., SEL-PLEX))) is administered to the subject as a prophylactic or therapeutic treatment for neurodegenerative disease.

In some embodiments, a composition comprising selenium (e.g., organic selenium (e.g., selenized yeast (e.g., SEL-PLEX))) is administered to a subject in combination with a calorie restricted diet in order to prevent aging or the aging process (e.g., attenuate age-associated gene expression). In some preferred embodiments, the present invention provides a method of altering cognitive function (e.g., neuronal circuit changes) associated with age comprising administering to a subject a composition comprising selenium (e.g., organic selenium (e.g., selenized yeast (e.g., SEL-PLEX))) under conditions such that the expression of Lhx8 is enhanced and/or elevated.

The present invention also provides a method of treatment or preventative for diabetes or reduction of signs or symptoms associated with diabetes or prophylactically preventing or minimizing biological events associated with the onset or progression of diabetes or reducing gene expression of genes correlated to the onset or progression of diabetes comprising administering to a subject (e.g., a subject suffering from diabetes, a subject with type I or type II diabetes, a subject having diabetes, a subject displaying signs or symptoms or pathology indicative of diabetes, a subject suspected of having diabetes, a subjects suspected of displaying signs or symptoms or pathology indicative of diabetes, a subject at risk of diabetes (e.g., a subject predisposed (e.g., with a family history of diabetes, genetically, etc.), a subject at risk of displaying pathology indicative of diabetes, an animal model of diabetes, or a healthy subject wishing to reduce risk of diabetes) a composition comprising selenium (e.g., organic selenium (e.g., selenized yeast (e.g., SEL-PLEX))) under conditions such that the expression of neurogenin-3 (Neurog3) is reduced in the subject or under conditions such that one or more signs or symptoms of diabetes is reduced or eliminated or that onset of progression of diabetes is delayed or prevented. In some embodiments, the treatment is prophylactic. The present invention provides compositions and methods for multiple types of diabetes. In some embodiments, diabetes treated with compositions and methods of the present invention is type I or type II diabetes. In some embodiments, the prophylactic treatment prevents the onset of signs and symptoms of diabetes in the subject. In some embodiments, the composition comprising selenium (e.g., organic selenium (e.g., selenized yeast (e.g., SEL-PLEX))) comprises one or more different forms of selenium. In some embodiments, the composition comprising selenium (e.g., organic selenium (e.g., selenized yeast (e.g., SEL-PLEX))) is co-administered with a diabetes therapeutic. Multiple diabetes therapeutics find use with the compositions and methods of the present invention including, but not limited to, Vanadium, metformin, thiazolidinedione, TZD, intermediate-acting insulin, neutral protamine Hagedorn, NPH, a long-acting insulin, glargine, Lantus, insulin, insulin detemir, Levemir, Incretin mimetic, Exenatide, Byetta, Sulfonylurea agent, chlorpropamide, tolbutamide, tolazamide, acetohexamide, glyburide, glipizide, glimepiride, Meglitinides, Repaglinide, Prandin, Biguanides, Metformin, Glucophage, Alpha-glucosidase inhibitor, AGI, Acarbose, Precose, Miglitol, Glyset, thiazolidinedione, Pioglitazone, Actos, Rosiglitazone, Avandia, Amylin analog, Pramlintide acetate, and Symlin.

The present invention also provides a method of altering the expression of Neurog3 in a subject comprising providing a subject; and a composition comprising selenium; and administrating the composition to the subject under conditions such that expression of Neurog3 is altered in the subject. In some embodiments, the expression of Neurog3 in said subject is characterized prior to and/or subsequent to administration of a composition comprising selenium to said subject. In some embodiments, the expression of Neurog3 is reduced in the subject. In some embodiments, the expression of Neurog3 is associated with pathology of diabetes. In some embodiments, the diabetes in type-I diabetes. In some embodiments, the reduction of expression of Neurog3 reduces signs and symptoms of diabetes in the subject. In some embodiments, the reduction of expression of Neurog3 prevents the onset of signs and symptoms of diabetes in the subject. In some embodiments, the composition comprising selenium comprises SEL-PLEX.

The present invention also provides a composition comprising selenium (e.g., organic selenium (e.g., selenized yeast (e.g., SEL-PLEX))) and a diabetes therapeutic.

DEFINITIONS

Figure 1:
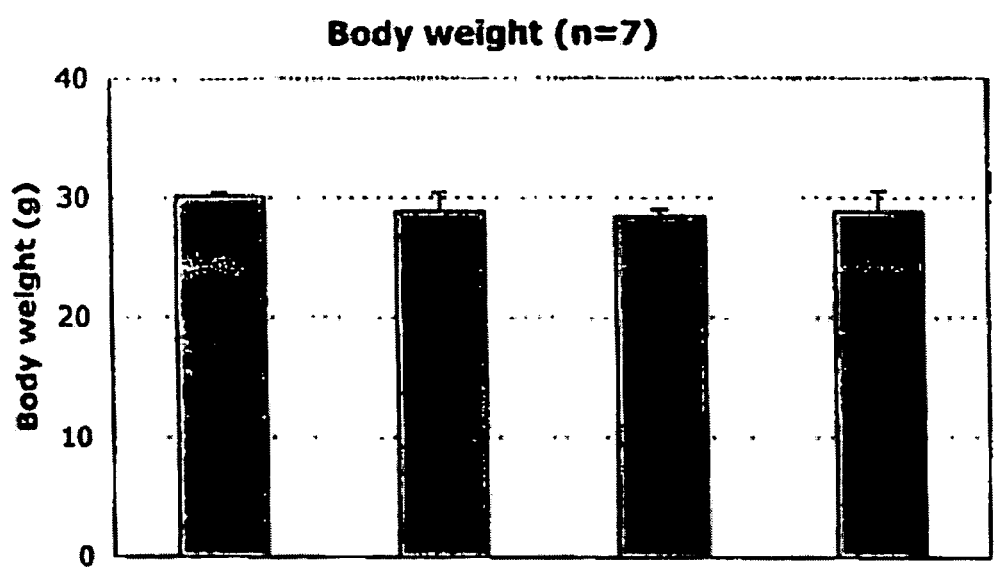
FIG. 1 shows the body weight of mice receiving a selenium deficient diet (Se def) or a diet comprising selnomethionine (SeM), sodium-selenite (Sod-sel), or SEL-PLEX.

As used herein, the terms "peptide," "polypeptide" and "protein" all refer to a primary sequence of amino acids that are joined by covalent "peptide linkages." In general, a peptide consists of a few amino acids, typically from 2-50 amino acids, and is shorter than a protein. The term "polypeptide" encompasses peptides and proteins. In some embodiments, the peptide, polypeptide or protein is synthetic, while in other embodiments, the peptide, polypeptide or protein are recombinant or naturally occurring. A synthetic peptide is a peptide that is produced by artificial means in vitro (i.e., was not produced in vivo).

The terms "sample" and "specimen" are used in their broadest sense and encompass samples or specimens obtained from any source. As used herein, the term "sample" is used to refer to biological samples obtained from animals (including humans), and encompasses fluids, solids, tissues, and gases. In some embodiments of this invention, biological samples include cerebrospinal fluid (CSF), serous fluid, urine, saliva, blood, and blood products such as plasma, serum and the like. However, these examples are not to be construed as limiting the types of samples that find use with the present invention.

As used herein, the terms "selenium-enriched yeast" and "selenized yeast" refer to any yeast (e.g., *Saccharomyces cerevisiae*) that is cultivated in a medium containing inorganic selenium salts. The present invention is not limited by the selenium salt used. Indeed, a variety of selenium salts are contemplated to be useful in the present invention including, but not limited to, sodium selenite, sodium selenate, cobalt selenite or cobalt selenate. Free selenomethionine (e.g., not associated with a cell or yeast) can also be used as the selenium source for selenium enriched yeast as yeast does incorporate this form of selenium. During cultivation, because of the chemical similarity between selenium and sulfur, yeast incorporate selenium in place of sulfur in what are normally sulfur-containing organic compounds within the cell. A selenium-containing compound in such yeast preparations is selenomethionine which will be present in a form that is incorporated into polypeptides/proteins. The amount of total cellular selenium present in the form of selenomethionine in such preparations will vary, but can be between 10 and 100%, 20-60%, 50-75% and between 60 and 75%. The remainder of the organic selenium in selenized yeast preparations is predominantly made up of intermediates in the pathway for selenomethionine biosynthesis. These include, but are not limited to, selenocysteine, selenocystathionine, selenohomocysteine and seleno-adenosylselenomethionine. The amount of residual inorganic selenium salt in the finished product is generally quite low (<2%). However, the present invention is not limited by this percentage, as preparations that contain more (e.g., between 2 and 70%) or less (e.g., between 0.1 and 2%) than this percentage are also encompassed by the invention.

As used herein, the term "SEL-PLEX" refers to a dried, nonviable selenium-enriched yeast (e.g., *Sacchoromyces cerevisiae* of accession number CNCM I-3060, Collection Nationale De Cultures De Microorganismes (CNCM), Institut Pasteur, Paris, France) cultivated in a fed-batch fermentation that provides incremental amounts of cane molasses and selenium salts in a manner that minimizes the detrimental effects of selenium salts on the growth rate of the yeast and allows for optimal incorporation of inorganic selenium into cellular organic material. Residual inorganic selenium is eliminated (e.g., using a rigorous washing process) and does not exceed 2% of the total selenium content.

As used herein, the term "organic selenium" refers to any organic compound wherein selenium replaces sulfur. Thus, organic selenium can refer to any such compound biosynthesized by yeast, or it can refer to free organic seleno-compounds that are chemically synthesized. An example of the latter is free selenomethionine.

As used herein, the term "inorganic selenium" generally refers to any selenium salt (e.g., sodium selenite, sodium selenate, cobalt selenite and cobalt selenate). There are also a variety of other inorganic selenium sources (See e.g., those listed in the Merck index). Selenized yeast may be generated using a source of inorganic selenium including, but not limited to, sodium selenite, sodium selenate, cobalt selenite, cobalt selenate, selenic acid, selenious acid, selenium bromide, selenium chloride, selenium hexafluoride, selenium oxide, selenium oxybromide, selenium oxychloride, selenium oxyfluoride, selenium sulfides, selenium tetrabromide, selenium tetrachloride and selenium tetrafluoride.

As used herein, the term "β-amyloid protein" refers to a protein or peptide proteolytically derived from the transmembrane amyloid precursor protein (APP). β-amyloid proteins can form soluble, non-fibrillar oligomeric amyloid β protein assembly (e.g., oligomeric amyloid β protein assembly or oligomeric assembly) and generally comprise between 2-12 β-amyloid proteins or peptides. β-amyloid proteins can also form fibrillar assemblies that generally comprise more than 12 β-amyloid proteins or peptides. β-amyloid proteins (e.g., individually or as found in the structures described above) are involved in forming plaques, one of the characterisitic traits of Alzheimer's disease.

As used herein, the term "oxidative stress" refers to the cytotoxic effects of oxygen radicals (e.g., superoxide anion ($O_2^{31}$), hydroxy radical (OH), and hydrogen peroxide ($H_2O_2$)), generated, for example, as byproducts of metabolic processes that utilize molecular oxygen (See e.g., Coyle et al., Science 262:689-695 (1993)).

As used herein, the terms "host," "subject" and "patient" refer to any animal, including but not limited to, human and non-human animals (e.g., dogs, cats, cows, horses, sheep, poultry, fish, crustaceans, etc.) that is studied, analyzed, tested, diagnosed or treated. As used herein, the terms "host," "subject" and "patient" are used interchangeably, unless indicated otherwise.

As used herein, the terms "Alzheimer's disease" and "AD" refer to a neurodegenerative disorder and encompasses familial Alzheimer's disease and sporadic Alzheimer's disease. The term "familial Alzheimer's disease" refers to Alzheimer's disease associated with genetic factors (i.e., demonstrates inheritance) while "sporadic Alzheimer's disease" refers to Alzheimer's disease that is not associated with prior family history of the disease. Symptoms indicative of Alzheimer's disease in human subjects typically include, but are not limited to, mild to severe dementia, progressive impairment of memory (ranging from mild forgetfulness to disorientation and severe memory loss), poor visuo-spatial skills, personality changes, poor impulse control, poor judgement, distrust of others, increased stubbornness, restlessness, poor planning ability, poor decision making, and social withdrawal. In severe cases, patients lose the ability to use language and communicate, and require assistance in personal hygiene, eating and dressing, and are eventually bedridden. Hallmark pathologies within brain tissue include extracellular neuritic β-amyloid plaques, neurofibrillary tangles, neurofibrillary degeneration, granulovascular neuronal degeneration, synaptic loss, and extensive neuronal cell death.

As used herein, the term "early-onset Alzheimer's disease" refers to the classification used in Alzheimer's disease cases diagnosed as occurring before the age of 65. As used herein, the term "late-onset Alzheimer's disease" refers to the classification used in Alzheimer's disease cases diagnosed as occurring after the age of 65.

As used herein, the terms "subject having Alzheimer's disease" or "subject displaying signs or symptoms or pathology indicative of Alzheimer's disease" or "subjects suspected of displaying signs or symptoms or pathology indicative of Alzheimer's disease" refer to a subject that is identified as having or likely to have Alzheimer's disease based on known Alzheimer's signs, symptoms and pathology.

As used herein, the terms "subject at risk of displaying pathology indicative of Alzheimer's disease" and "subject at risk of Alzheimer's disease" refer to a subject identified as being at risk for developing Alzheimer's disease (e.g., due to age or familial inheritance pattern of Alzheimer's disease in the subject's family).

As used herein, the term "Alzheimer's therapeutic" refers to an agent used to treat or prevent Alzheimer's disease. Such agents include, but are not limited to, small molecules, drugs, antibodies, pharmaceuticals, and the like. For example, therepeutics used to treat Alzheimer's disease include, but are not limited to, NMDA antagonists (e.g., memantine), and AChE inhibitors (e.g., tacrine (Cognex), donepezil (Aricept), rivastigmine (Exelon), and galantamine (galanthamine, Reminyl)).

As used herein, the term "lesion" refers to a wound or injury, or to a pathologic change in a tissue. For example, the β-amyloid plaque lesions observed in the brains of patients having Alzheimer's disease are considered the hallmark pathology characteristic of the disease.

As used herein, the terms "amyotrophic lateral sclerosis" and "ALS" refer to a neurodegenerative disorder that is characterized as a devastating disorder of the anterior horn cells of the spinal cord and the motor cranial nuclei that leads to progressive muscle weakness and atrophy. Symptoms indicative of ALS in human subjects typically include, but are not limited to, mild to severe weakness of bulbar muscles or of single or multiple limb muscle groups (e.g., bilateral or symmetrical) limb weakness, weakness and atrophy of the intrinsic hand muscles that progresses to involve the forearms and shoulder girdle muscles and the lower extremities. Involvement of both upper and lower motor neurons is characteristic. Patients develop variable hyperreflexia, clonus, spasticity, extensor plantar responses, and limb or tongue fasciculations. Wallerian degeneration of corticospinal and corticobulbar tracts may be demonstrated by MRI (high-intensity T2 lesions in frontal lobes) or in postmortem examination.

As used herein, the terms "subject having ALS" or "subject displaying signs or symptoms or pathology indicative of ALS" or "subjects suspected of displaying signs or symptoms or pathology indicative of ALS" refer to a subject that is identified as having or likely to have ALS based on known ALS signs, symptoms and pathology.

As used herein, the terms "subject at risk of displaying pathology indicative of ALS" and "subject at risk of ALS" refer to a subject identified as being at risk for developing ALS (e.g., due to age or familial inheritance pattern of ALS in the subject's family).

As used herein, the term "ALS therapeutic" refers to an agent used to treat or prevent ALS. Such agents include, but are not limited to, small molecules, drugs, antibodies, pharmaceuticals, and the like. For example, therepeutics used to treat ALS include, but are not limited to, Riluzole, Baclofen (Lioresal) and Tizanidine (Zanaflex).

As used herein, the terms "Huntington's Disease" and "HD" refer to a neurodegenerative disorder that is an adult-onset, autosomal dominant inherited disorder associated with cell loss within a specific subset of neurons in the basal ganglia and cortex. Characteristic features of HD include involuntary movements (e.g., chorea, a state of excessive, spontaneous movements, irregularly timed, randomly distributed, and abrupt, is a characteristic feature of HD), dementia, and behavioral changes. Neuropathology in HD occurs within the neostriatum, in which gross atrophy of the caudate nucleus and putamen is accompanied by selective neuronal loss and astrogliosis. Marked neuronal loss also is seen in deep layers of the cerebral cortex. Other regions, including the globus pallidus, thalamus, subthalamic nucleus, substantia nigra, and cerebellum, show varying degrees of atrophy depending on the pathologic grade.

As used herein, the terms "subject having HD" or "subject displaying signs or symptoms or pathology indicative of HD" or "subjects suspected of displaying signs or symptoms or pathology indicative of HD" refer to a subject that is identified as having or likely to have HD based on known HD signs, symptoms and pathology.

As used herein, the terms "subject at risk of displaying pathology indicative of HD" and "subject at risk of HD" refer to a subject identified as being at risk for developing HD (e.g., due to age or familial inheritance pattern of HD in the subject's family).

As used herein, the term "HD therapeutic" refers to an agent used to treat or prevent HD. Such agents include, but are not limited to, small molecules, drugs, antibodies, pharmaceuticals, and the like. For example, therepeutics used to treat HD include, but are not limited to, anticonvulsant medications including, but not limited to valproic acid (e.g., Depakote, Depakene, and Depacon) and benzodiazepines such as clonazepam (e.g., Klonopin), Antipsychotic medications (e.g., risperidone (e.g., Risperdal), and haloperidol (e.g., Haldol)), Rauwolfia alkoids (e.g., resperine), and antidepressants (e.g., paroxetine (e.g., Paxil)).

As used herein, the terms "Parkinson's disease" and "PD" refer to a neurodegenerative disorder that is a progressive neurodegenerative disorder associated with a loss of dopaminergic nigrostriatal neurons. Characteristic features of PD include loss of pigmented dopaminergic neurons in the substantia nigra and the presence of Lewy bodies.

As used herein, the terms "subject having PD" or "subject displaying signs or symptoms or pathology indicative of PD" or "subjects suspected of displaying signs or symptoms or pathology indicative of PD" refer to a subject that is identified as having or likely to have PD based on known PD signs, symptoms and pathology.

As used herein, the terms "subject at risk of displaying pathology indicative of PD" refer and "subject at risk of PD" refer to a subject identified as being at risk for developing PD (e.g., due to age or familial inheritance pattern of PD in the subject's family).

As used herein, the term "PD therapeutic" refers to an agent used to treat or prevent PD. Such agents include, but are not limited to, small molecules, drugs, antibodies, pharmaceuticals, and the like. For example, therepeutics used to treat PD include, but are not limited to, dopamine prodrugs such as levadopa/PDI and levodopa/carbidopa (e.g., Sinemet, Sinemet CR), dopamine agonsts such as apomorphine (e.g., Apokyn), bromocriptine (e.g., Parlodel), pergolide (e.g., Permax), pramipexole (e.g., Mirapex), and ropinirole (e.g., Requip), catechol-O-methyltransferase (COMT) inhibitors such as tolcapone (e.g., Tasmar), and entacapone (e.g., Comtan), anticholinergics such as trihexyphenidyl (e.g., Artane, Trihexy), and benztropine mesylate (e.g., Cogentin), MAO-B inhibitors such as selegiline (e.g., Eldepryl), and amantadine (e.g., Symmetrel).

As used herein, the terms "Multiple sclerosis" and "MS" refer to a neurodegenerative disorder that is an inflammatory, demyelinating disease of the central nervous system (CNS). MS lesions, characterized by perivascular infiltration of monocytes and lymphocytes, appear as indurated areas in pathologic specimens; hence, the term "sclerosis in plaques." Characteristic features of MS include perivenular infiltration of lymphocytes and macrophages in the parenchyma of the brain, brain stem, optic nerves, and spinal cord, almost constant lesion formation and a progressive clinical course leading to physical disability.

As used herein, the terms "subject having MS" or "subject displaying signs or symptoms or pathology indicative of MS" or "subjects suspected of displaying signs or symptoms or pathology indicative of MS" refer to a subject that is identified as having or likely to have MS based on known MS signs, symptoms and pathology.

As used herein, the terms "subject at risk of displaying pathology indicative of MS" and "subject at risk of MS" refer to a subject identified as being at risk for developing MS.

As used herein, the term "MS therapeutic" refers to an agent used to treat or prevent MS. Such agents include, but are not limited to, small molecules, drugs, antibodies, pharmaceuticals, and the like. For example, therepeutics used to treat MS include, but are not limited to, immunomodulators (e.g., Interferon beta-1a (Avonex), Interferon beta-1a (Rebif), Interferon beta-1b (Betaseron), Glatiramer acetate (Copaxone), and Natalizumab (Tysabri)), corticosteroids (e.g., methylprednisolone), and immunosuppressors (e.g., Mitoxantrone (Novantrone), Cyclophosphamide (Cytoxan, Neosar), Azathioprine (IMURAN, Methotrexate (Rheumatrex).

As used herein, the term "diabetes" refers to an autoimmune disease characterized by necrosis of pancreatic islet cells and a lack of insulin secretion. For example, patients with type 1 diabetes are dependent on insulin. Characteristics traits of diabetes include peripheral insulin resistance with an insulin-secretory defect that varies in severity, and complications that include hypoglycemia and hyperglycemia, increased risk of infections, microvascular complications (eg, retinopathy, nephropathy), neuropathic complications, and macrovascular disease.

As used herein, the terms "subject having diabetes" or "subject displaying signs or symptoms or pathology indicative of diabetes" or "subjects suspected of displaying signs or symptoms or pathology indicative of diabetes" refer to a subject that is identified as having or likely to have diabetes based on known diabetes signs, symptoms and pathology.

As used herein, the term "subject at risk of displaying pathology indicative of diabetes" and "subject at risk of diabetes" refer to a subject identified as being at risk for developing diabetes (e.g., due to age, weight, race, or familial inheritance pattern of diabetes in the subject's family).

As used herein, the term "diabetes therapeutic" refers to an agent used to treat or prevent diabetes. Such agents include, but are not limited to, small molecules, drugs, antibodies, pharmaceuticals, and the like. For example, therepeutics used to treat diabetes include, but are not limited to, oral medication to increase insulin sensitivity (eg, metformin, a thiazolidinedione (TZD)), intermediate-acting insulin (eg, neutral protamine Hagedorn (NPH)), a long-acting insulin (eg, glargine (Lantus) insulin, insulin detemir (Levemir)), Incretin mimetics (e.g., Exenatide (Byetta)), Sulfonylurea agents (e.g., chlorpropamide, tolbutamide, tolazamide, acetohexamide, glyburide, glipizide, and glimepiride), Meglitinides (e.g., Repaglinide (Prandin)), Biguanides (e.g., Metformin (Glucophage)), Alpha-glucosidase inhibitors (AGIs) (e.g., Acarbose (Precose), Miglitol (Glyset)), thiazolidinediones (e.g., Pioglitazone (Actos), Rosiglitazone (Avandia)), and Amylin analogs (e.g., Pramlintide acetate (Symlin)).

As used herein, the terms "subject at risk of displaying pathology indicative of stroke" and "subject at risk of stroke" refer to a subject identified as being at risk for developing stroke (e.g., due to age, weight, race, or familial inheritance pattern of stroke in the subject's family).

As used herein, the term "cognitive function" generally refers to the ability to think, reason, concentrate, or remember. Accordingly, the term "decline in cognitive function" refers to the deterioration of lack of ability to think, reason, concentrate, or remember.

As used herein, the term "antibody" (or "antibodies") refers to any immunoglobulin that binds specifically to an antigenic determinant, and specifically binds to proteins identical or structurally related to the antigenic determinant that stimulated their production. Thus, antibodies can be useful in assays to detect the antigen that stimulated their production. Monoclonal antibodies are derived from a single clone of B lymphocytes (i.e., B cells), and are generally homogeneous in structure and antigen specificity. Polyclonal antibodies originate from many different clones of antibody-producing cells, and thus are heterogenous in their structure and epitope specificity, but all recognize the same antigen. In some embodiments, monoclonal and polyclonal antibodies are used as crude preparations, while in preferred embodiments, these antibodies are purified. For example, in some embodiments, polyclonal antibodies contained in crude antiserum are used. Also, it is intended that the term "antibody" encompass any immunoglobulin (e.g., IgG, IgM, IgA, IgE, IgD, etc.) obtained from any source (e.g., humans, rodents, non-human primates, lagomorphs, caprines, bovines, equines, ovines, etc.).

As used herein, the terms "auto-antibody" or "auto-antibodies" refer to any immunoglobulin that binds specifically to an antigen that is native to the host organism that produced the antibody (i.e., the antigen is directed against "self" antigens). The presence of auto-antibodies is referred to herein as "autoimmunity."

As used herein, the term "antigen" is used in reference to any substance that is capable of being recognized by an antibody. It is intended that this term encompass any antigen and "immunogen" (i.e., a substance that induces the formation of antibodies). Thus, in an immunogenic reaction, antibodies are produced in response to the presence of an antigen or portion of an antigen. The terms "antigen" and "immunogen" are used to refer to an individual macromolecule or to a homogeneous or heterogeneous population of antigenic macromolecules. It is intended that the terms antigen and immunogen encompass protein molecules or portions of protein molecules, that contains one or more epitopes. In many cases, antigens are also immunogens, thus the term "antigen" is often used interchangeably with the term "immunogen." In some preferred embodiments, immunogenic substances are used as antigens in assays to detect the presence of appropriate antibodies in the serum of an immunized animal.

As used herein, the terms "antigen fragment" and "portion of an antigen" and the like are used in reference to a portion of an antigen. Antigen fragments or portions typically range in size, from a small percentage of the entire antigen to a large percentage, but not 100%, of the antigen. However, in situations where "at least a portion" of an antigen is specified, it is contemplated that the entire antigen is also present (e.g., it is not intended that the sample tested contain only a portion of an antigen). In some embodiments, antigen fragments and/or portions thereof, comprise an "epitope" recognized by an antibody, while in other embodiments these fragments and/or portions do not comprise an epitope recognized by an antibody. In addition, in some embodiments, antigen fragments and/or portions are not immunogenic, while in preferred embodiments, the antigen fragments and/or portions are immunogenic.

The terms "antigenic determinant" and "epitope" as used herein refer to that portion of an antigen that makes contact with a particular antibody variable region. When a protein or fragment (or portion) of a protein is used to immunize a host animal, numerous regions of the protein are likely to induce the production of antibodies that bind specifically toga given region or three-dimensional structure on the protein (these regions and/or structures are referred to as "antigenic determinants"). In some settings, antigenic determinants compete with the intact antigen (i.e., the "immunogen" used to elicit the immune response) for binding to an antibody.

The terms "specific binding" and "specifically binding" when used in reference to the interaction between an antibody and an antigen describe an interaction that is dependent upon the presence of a particular structure (i.e., the antigenic determinant or epitope) on the antigen. In other words, the antibody recognizes and binds to a protein structure unique to the antigen, rather than binding to all proteins in general (i.e., non-specific binding).

As used herein, the term "immunoassay" refers to any assay that uses at least one specific antibody for the detection or quantitation of an antigen. Immunoassays include, but are not limited to, Western blots, ELISAs, radio-immunoassays, and immunofluorescence assays.

The terms "Western blot," "Western immunoblot" "immunoblot" and "Western" refer to the immunological analysis of protein(s), polypeptides or peptides that have been immobilized onto a membrane support. The proteins are first resolved by polyacrylamide gel electrophoresis (i.e., SDS-PAGE) to separate the proteins, followed by transfer of the protein from the gel to a solid support, such as nitrocellulose or a nylon membrane. The immobilized proteins are then exposed to an antibody having reactivity towards an antigen of interest. The binding of the antibody (i.e., the primary antibody) is detected by use of a secondary antibody that specifically binds the primary antibody. The secondary antibody is typically conjugated to an enzyme that permits visualization of the antigen-antibody complex by the production of a colored reaction product or catalyzes a luminescent enzymatic reaction (e.g., the ECL reagent, Amersham).

As used herein, the term "ELISA" refers to enzyme-linked immunosorbent assay (or EIA). Numerous ELISA methods and applications are known in the art, and are described in many references (See, e.g., Crowther, "Enzyme-Linked Immunosorbent Assay (ELISA)," in Molecular Biomethods Handbook, Rapley et al. (eds.), pp. 595-617, Humana Press, Inc., Totowa, N.J. (1998); Harlow and Lane (eds.), Antibodies: A Laboratory Manual, Cold Spring Harbor Laboratory Press (1988); Ausubel et al. (eds.), Current Protocols in Molecular Biology, Ch. 11, John Wiley & Sons, Inc., New York (1994)). In addition, there are numerous commercially available ELISA test systems.

As used herein, the terms "reporter reagent," "reporter molecule," "detection substrate" and "detection reagent" are used in reference to reagents that permit the detection and/or quantitation of an antibody bound to an antigen. For example, in some embodiments, the reporter reagent is a colorimetric substrate for an enzyme that has been conjugated to an antibody. Addition of a suitable substrate to the antibody-enzyme conjugate results in the production of a colorimetric or fluorimetric signal (e.g., following the binding of the conjugated antibody to the antigen of interest). Other reporter reagents include, but are not limited to, radioactive compounds. This definition also encompasses the use of biotin and avidin-based compounds (e.g., including but not limited to neutravidin and streptavidin) as part of the detection system.

As used herein, the term "signal" is used generally in reference to any detectable process that indicates that a reaction has occurred, for example, binding of antibody to antigen. It is contemplated that signals in the form of radioactivity, fluorimetric or colorimetric products/reagents will all find use with the present invention. In various embodiments of the present invention, the signal is assessed qualitatively, while in alternative embodiments, the signal is assessed quantitatively.

As used herein, the term "solid support" is used in reference to any solid or stationary material to which reagents such as antibodies, antigens, and other test components are attached. For example, in an ELISA method, the wells of microtiter plates provide solid supports. Other examples of solid supports include microscope slides, coverslips, beads, particles, cell culture flasks, as well as many other suitable items.

As used herein, the term "characterizing tissue in a subject" refers to the identification of one or more properties of a tissue sample. In some embodiments, tissues are characterized by the identification of the expression, or lack thereof, of various genes described in detail herein.

As used herein, the term "reagent(s) capable of specifically detecting gene expression" refers to reagents capable of or sufficient to detect the expression of various genes described in detail herein (e.g., including, but not limited to, Se1W, Sepn1, Se1R, Sod2, Dio2, Glo1, Phb, Lhx8, TGF-β2, Neurog3, Spry2, Gstt2, Gstt1, Gsta3, Gsta4, Gstm1, Gstm2, or Gstm3, C1q, C1q alpha, C1q beta, C1q gamma, CORS-26, cathepsin B, cathepsin D, cathepsin Z, cathepsin O, nicastrin, presenilin 1, presenilin 2, calsenilin, Apbb1/Fe65, Aplp 1, Apba1, Gstp1, Gstz1, Gstm7, Gadd45g1p, Gadd45b). Examples of suitable reagents include, but are not limited to, nucleic acid probes capable of specifically hybridizing to mRNA or cDNA, and antibodies (e.g., monoclonal or polyclonal antibodies).

As used herein, the term "effective amount" refers to the amount of a composition (e.g., comprising selenium—e.g., SEL-PLEX) sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., composition comprising SEL-PLEX and one or more other agents—e.g., an Alzheimer's disease therapeutic, or, a second form of selenium) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" or grammatical equivalents encompasses the improvement and/or reversal of the symptoms of disease (e.g., neurodegenerative disease). A compound which causes an improvement in any parameter associated with disease when used in the screening methods of the instant invention may thereby be identified as a therapeutic compound. The term "treatment" refers to both therapeutic treatment and prophylactic or preventative measures. For example, those who may benefit from treatment with compositions and methods of the present invention include those already with a disease and/or disorder (e.g., neurodegenerative disease, diabetes or lack of or loss of cognitive function) as well as those in which a disease and/or disorder is to be prevented (e.g., using a prophylactic treatment of the present invention).

As used herein, the term "at risk for disease" refers to a subject (e.g., a human) that is predisposed to experiencing a particular disease. This predisposition may be genetic (e.g., a particular genetic tendency to experience the disease, such as heritable disorders), or due to other factors (e.g., age, weight, environmental conditions, exposures to detrimental compounds present in the environment, etc.). Thus, it is not intended that the present invention be limited to any particular risk, nor is it intended that the present invention be limited to any particular disease.

As used herein, the term "suffering from disease" refers to a subject (e.g., a human) that is experiencing a particular disease. It is not intended that the present invention be limited to any particular signs or symptoms, nor disease. Thus, it is intended that the present invention encompass subjects that are experiencing any range of disease (e.g., from sub-clinical manifestation to full-blown disease) wherein the subject exhibits at least some of the indicia (e.g., signs and symptoms) associated with the particular disease.

As used herein, the terms "disease" and "pathological condition" are used interchangeably to describe a state, signs, and/or symptoms that are associated with any impairment of the normal state of a living animal or of any of its organs or tissues that interrupts or modifies the performance of normal functions, and may be a response to environmental factors (such as malnutrition, industrial hazards, or climate), to specific infective agents (such as worms, bacteria, or viruses), to inherent defect of the organism (such as various genetic anomalies, or to combinations of these and other factors.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of disease (e.g., neurodegenerative disease).

As used herein, the term "kit" is used in reference to a combination of reagents and other materials. It is contemplated that the kit may include reagents such as nutrients and drugs as well as administration means. It is not intended that the term "kit" be limited to a particular combination of reagents and/or other materials.

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., composition comprising SEL-PLEX) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells that line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "nucleic acid molecule" refers to any nucleic acid containing molecule, including but not limited to, DNA or RNA. The term-encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "gene expression" and "expression" refer to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refer to regulation that increases and/or enhances the production of gene expression products (e.g., RNA or protein), while "down-regulation" or "repression" refer to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization (1985)). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharamcia), 5 g BSA (Fraction V; Sigma)) and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest.

A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk⁻ cell lines, the CAD gene that is used in conjunction with CAD-deficient cells and the mammalian hypoxanthine-guanine phosphoribosyl transferase (hprt) gene that is used in conjunction with hprt⁻ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., Alzheimer's disease, ALS, Parkinson's disease, etc.). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "target RNA molecule" refers to an RNA molecule to which at least one strand of the short double-stranded region of an siRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

DETAILED DESCRIPTION OF THE INVENTION

Selenium is a trace element involved in regulating aspects of the antioxidant defense mechanism in all living tissues by interacting with the body's glutathione (GSH) and its major Se-containing antioxidant enzymes, glutathione peroxidase (GPX) and thioredoxin reductase (See, e.g., Goehring et al., J. Anim. Sci. 59, 725-732 (1984); Gerloff et al., J. Anim. Sci. 70, 3934-3940 (1992)). Glutathione and GPX have the capacity to protect the integrity of unsaturated bonds of membrane phospholipids by extinguishing free radical attacks capable of initiating and propagating lipid oxidation (See, e.g., Meister and Anderson, Annu. Rev. Biochem. 52, 711-760 (1983); Deleve and Kaplowitz, Pharm. Ther. 52, 287-305 (1991); Palmer and Paulson, Nutr. Rev. 55, 353-361 (1997)).

Selenium has also been associated with reduced cancer risk in several epidemiologic studies (See, e.g., Salonen et al., Am. J. Epidemiol. 120: 342-349 (1984); Willett et al., Lancet 2: 130-134 (1983); Virtamo et al., Cancer 60: 145-148 (1987)). Various selenium compounds of natural and synthetic origin have been shown to inhibit tumor development in animal studies in a wide range of dosages (See, e.g., Ip, J. Nutr. 128: 1845-1854 (1998)). Although most animal studies have employed pharmacologic doses of selenium (>2 mg/kg) in cancer chemoprevention (See, e.g., Ip, J. Nutr. 128: 1845-1854 (1998)), selenium deficiency has also been shown to enhance mammary (See, e.g., Ip and Daniel, Cancer Res. 45: 61-65 (1985)) and UVB-induced skin carcinogenesis (See, e.g., Pence et al., 102: 759-761 (1994)).

A recent double-blind, randomized cancer prevention trial in humans involving physiologic doses (0.2 mg) of selenium demonstrated a reduction in incidence of lung, prostate and intestinal cancers (See, e.g., Clark et al., J. Am. Med. Assoc. 276:1957-1963 (1996)).

Despite decades of research in the mechanisms of action of selenium, little to nothing is known regarding other potential targets of selenium (e.g., genes or regulatory pathways) and beneficial effects that could be provided to a subject through administration of selenium. Also lacking is information regarding what forms of selenium (e.g., organic, inorganic, or both) can and cannot be used for bringing about these effects. Thus, it would be of great value to elucidate various ways in which different forms of selenium could be used to benefit certain systems (e.g., nervous, endocrine, and metabolic systems) of a subject (e.g., a human, bovine or other mammal). Furthermore, understanding how various forms of selenium differ in their ability to exert effects on a subject provides the ability to customize treatments for subjects suffering from, or at risk of, a disease or disorder that might be benefited by such treatment (e.g., specific forms of selenium could be used independently or with other known agents to treat or prevent diseases or disorders).

Accordingly, the present invention demonstrates how specific forms of selenium (e.g., selenomethionine (SeM), Sodium-selenite (Sod-sel), and SEL-PLEX) may be used to benefit a subject. In particular, the present invention demonstrates that compositions and methods of the present invention can be used to stabilize or increase the general health and cognitive function of a subject. For example, as described in detail herein, the present invention provides compositions and methods that alter cellular function thereby providing beneficial effects to multiples systems of a subject including, but not limited to, the neurological system, the nervous system, the endocrine system, the metabolic system, and the immune system. The present invention also provides methods of using selenium with other agents for treating or preventing disease. Thus, the present invention provides compositions comprising selenium (e.g., SEL-PLEX) and methods of using the same as a therapeutic and/or prophylactic treatment (e.g., for neurodegenerative disease, for enhancing cognitive function, or retarding age-associated gene expression). The following examples are provided in order to illustrate multiple ways that compositions and methods of the present invention may be utilized in order to provide a beneficial effect to a subject, and are not meant to be construed as limiting the scope of the invention.

I. Neurodegenerative Diseases.

In some embodiments, the present invention provides the administration of selenium, independently or in combination with one or more other agents, for the prophylactic or therapeutic treatment of neurodegenerative disease. In preferred embodiments, the present invention provides a prophylactic treatment comprising administering a composition comprising selenium to a subject at risk of developing a neurodegenerative disease, thereby preventing the neurodegenerative disease. In other preferred embodiments, the present invention provides a method of treating or preventing a neurodegenerative disease comprising providing to a subject an agent used for treatment or prevention of a neurodegenerative disease in combination with a composition comprising selenium. The present invention demonstrates for the first time that certain forms of selenium may be compatible with the above mentioned methods, while others forms of selenium may not. Thus, in some embodiments, the present invention provides one or more forms of selenium (e.g., SEL-PLEX and/or Sod-sel) that is biologically available and is administered alone or co-administered with an agent used for treatment or prevention of a neurodegenerative disease, wherein the form of selenium chosen functions to treat or prevent the neurodegenerative disease.

The form of selenium administered to a subject will depend on the target (e.g., gene) sought to be treated. As demonstrated by the present invention, the presence and level of beneficial effect attained varies depending on the form of selenium used (See Examples 2-10). In preferred embodiments, selenium is provided in the form of SEL-PLEX. In other embodiments, selenium is provided as sodium-selenite. In still other embodiments, selenium is provided as selenomethionine or selenium enriched yeast. In some embodiments, selenium is provided as selenocysteine or a selenate compound. In some embodiments, selenium may be chemically linked to an agent (e.g., an agent used for treating neurodegenerative disease) to form a selenium-agent derivative.

Once the desired form of selenium is chosen, it can be administered alone or in combination with one or more agents used for the prevention or treatment of a neurodegenerative disease. The agent may be one approved by a regulatory authority for such a treatment (e.g., the US Food and Drug Administration (FDA) or the European Medicines Evaluation Agency (EMEA)). Compositions and methods of the present invention are contemplated to be useful for the treatment of a variety of neurodegenerative diseases including, but not limited to, Alzheimer's disease, amyotrophic lateral sclerosis, Parkinson's disease, Huntington's disease, multiple sclerosis, spinocerebellar ataxias, Friedreich's ataxia, and myotonic dystrophy.

A. Alzheimer's Disease

In some embodiments of the present invention, compositions and methods of the present invention are utilized in the treatment of Alzheimer disease. Alzheimer disease (AD) is a common cause of dementia, which is an acquired cognitive and behavioral impairment of sufficient severity to markedly interfere with social and occupational functioning.

AD affects approximately 5 million people in the United States and more than 30 million people worldwide. A larger number of individuals have decreased levels of cognitive impairment (eg, minimal cognitive impairment), which frequently evolves into a full-blown dementia, thereby increasing the number of affected persons. The prevalence of AD is expected to substantially increase in this century because it preferentially affects the elderly, who constitute the fastest growing age group in many, especially industrialized, countries. Statistical projections indicate that the number of persons affected by the disorder in the United States will nearly triple by the year 2050.

AD is also a major public health problem from the economic perspective. In the United States, the cost of caring for patients with AD was more than $110 billion per year in the early 1990s, and the average yearly cost per patient is about $45,000. Because methods for assessing the economic effects of neurodegenerative disorders are still in their infancy, these figures are likely underestimates.

The anatomic pathology of AD includes neurofibrillary tangles (NFTs); senile plaques (SPs) at the microscopic level; and cerebrocortical atrophy, which predominantly involves the association regions and particularly the medial aspect of the temporal lobe. Although NFTs and SPs are characteristic of AD, they are not pathognomonic. In fact many other neurodegenerative conditions distinct from AD are characterized by NFTs (eg, progressive supranuclear palsy, dementia pugilistica) or SPs (eg, normal aging). Therefore, the mere presence of these lesions is not sufficient to diagnose AD. These lesions must be present in sufficient numbers and in a characteristic topographic distribution to fulfill the current histopathologic criteria for AD.

In addition to NFTs and SPs, many other lesions of AD have been recognized since Alzheimer's original papers were published. These include (1) the granulovacuolar degeneration of Shimkowicz; (2) the neuropil threads of Braak et al; and (3) neuronal loss and synaptic degeneration, which are thought to ultimately mediate the cognitive and behavioral manifestations of the disorder.

AD is the most common neurodegenerative disorder worldwide. In AD, neurons of the hippocampus and cerebral cortex are selectively lost. Brains of individuals with AD manifest two characteristic lesions: extracellular amyloid (or senile) plaques and intracellular neurofibrillary tangles of hyperphosphorylated tau protein (See, e.g., Selkoe, Nature 426, 900-904 (2003)). Amyloid plaques contain small, toxic cleavage products (denoted as Aβ40 and Aβ42) of the amyloid precursor protein (APP). The apoE4 (apolipoprotein E4) genotype is a powerful risk factor for developing AD, and it may possibly affect β-amyloid protein (Aβ) deposition and neurofibrillary tangle formation (See, e.g., Roses, Curr. Opin. Neurol. 4, 265-270 (1996)). Mutations in three genes that are inherited in an autosomal dominant fashion have been linked to rare familial, early-onset forms of AD. These genes include those encoding APP, presenilin 1 (PS1) and presenilin 2 (PS2). One common event in both familial and sporadic types of AD is the increased production and accumulation of the toxic β-amyloid protein. This observation has led to the 'amyloid cascade hypothesis' that excessive Aβ production is the primary cause of the disease.

APP is a type I membrane protein and contains a large extracellular region, a transmembrane helix and a short cytoplasmic tail. Toxic Aβ originates from regulated intramembrane proteolysis of APP by a complex of secretases. The first cleavage of APP is mediated by β- or α-secretase, releasing most of the extracellular portion of APP as two fragments, APPs-α and APPs-β, leaving behind the C-terminal membrane bound fragment. This portion of APP is then cleaved by a large protein complex, γ-secretase, at several sites including amino acid (aa) 711 (Ab40) and at least three additional subsites at aa713 (Aβ42), aa714 (Aβ43) and aa720 (Aβ49). Several mutations in APP, such as the Swedish mutation, cluster at the γ-secretase cleavage sites; these mutations result in increased amounts of Aβ peptide and protofibril formation (See, e.g., Singleton et al., Hum. Mol. Genet. 13 (Spec. no. 1), R123-R126 (2004)).

The precise composition of the γ-secretase complex is still under debate, but presenilin 1 (PS1), presenilin 2 (PS2), nicastrin, Aph-1 and Pen-2 appear to be required (See, e.g., Haas and Steiner, Trends Cell Biol. 12, 556-562 (2002); Edbauer et al., Nat. Cell Biol. 5, 486-488 (2003); Haass, EMBO J. 23, 483-488 (2004)). PS1 is a transmembrane domain aspartyl protease that cleaves its substrates in the membrane-spanning region. PS1 is probably responsible for the generation of Aβ fragments. An additional protein involved is calsenilin. Calsenilin is over-expressed (e.g., up-regulated) in neurons and astrocytes in an Alzheimer's diseased brain (See, e.g., Jin et al., Neuroreport 16, 451-455 (2005)). Overexpression of calsenilin enhances g-secretase activity, demonstrating that calsenilin is a regulatory factor for g-secretase (See, e.g., Jo et al., Neurosci Lett, 378, 59-64 (2005)).

More than 100 missense mutations in PS1 and PS2 have been identified in rare familial, early-onset AD (See, e.g., Hutton et al., Essays Biochem. 33, 117-131 (1998)). Experiments in culture and transgenic mice reveal that these mutations result in increased Aβ production (See, e.g., Scheuner. et al., Nat. Med. 2, 864-870 (1996); Borchelt et al., Neuron 19, 939-945 (1997)). Conversely, mice lacking PS1 have decreased Aβ40 and Aβ42 production (See, e.g., De Strooper, et al., Nature 391, 387-390 (1998); Naruse, et al., 21, 1213-1221 (1998)), suggesting that PS1 has a pivotal role in γ-secretase activity. C-terminal cleavage of APP by caspase enzymes may also be required for toxicity (See, e.g., Lu et al., Nat. Med. 6, 385-386 (2000)).

Several mechanisms have been proposed regarding how Aβ does its damage. One view suggests that Aβ protofibrils activate microglia, inciting an inflammatory response and release of neurotoxic cytokines. Nonsteroidal anti-inflammatory drugs (NSAIDs) including ibuprofen delay the onset of AD (See, e.g., Stewart et al., Neurology 48, 626-632 (1997)). Additionally, NSAIDs reduce the production of Aβ42 (See, e.g., Weggen et al., Nature 414, 212-216 (2001)).

In a second view, Aβ protofibrils trigger excessive release of excitatory amino acids like glutamate from glial cells that may injure nearby neurons by excitotoxicity. Overactivation of glutamate receptors of the N-methyl-D-aspartate (NMDA) subtype results in increased intracellular $Ca^{2+}$, which activates neuronal nitric oxide synthase and consequently generates nitric oxide (NO). When generated in excess, NO combines with superoxide anion ($O_2^-$), forming the highly reactive and neurotoxic product peroxynitrite ($ONOO^-$), which leads to further oxidative and nitrosative stress in part via mitochondrial injury. In fact, positive phase III human trials of the uncompetitive NMDA receptor channel blocker, memantine, led to its recent approval for the treatment of AD (See, e.g., Lipton, Nature 428, 473 (2004)).

Cholinergic transmission and synaptic density are considerably decreased in AD patients. The mechanism for synaptic damage is unknown, but diffusible oligomeric forms of Aβ may be important. Synaptic dysfunction probably contributes to memory loss and cognitive deficits in AD. In fact, APP transgenic mice manifest cellular, biochemical and electrophysiological evidence of synaptic deficits before Aβ deposition, including reduced excitatory postsynaptic potentials and long term potentiation regarded as a correlate of learning and memory (See, e.g., Chapman et al., Nat. Neurosci. 2, 271-276 (1999)). Inhibition of γ-secretase decreases oligomeric Aβ and LTP deficits (See, e.g., Walsh et al., Nature 416, 535-539 (2002)).

Aβ may also mediate harmful effects by binding redox-reactive metals, which in turn release free radicals (See, e.g., Bush et al., J. Biol. Chem. 268, 16109-16112 (1993); Bush et al., Science 265, 1464-1467 (1994); Lovell et al., J. Neurol. Sci. 158, 47-52 (1998); Dong et al., Biochemistry 42, 2768-2773 (2003); Opazo et al., J. Biol. Chem. 277, 40302-40308 (2002); Bush et al., Alzheimer Dis. Assoc. Disord. 17, 147-150 (2003); 36 Huang et al., Biochemistry 38, 7609-7616 (1999)). Chelation of zinc and copper provides neuroprotective effects (See, e.g., Bush, Aging 23, 1031-1038 (2002)). For example, clioquinol (CQ), an antibiotic that also chelates zinc and copper and crosses the blood-brain barrier, decreases brain Aβ deposition and improves learning in mutant APP transgenic mice (See, e.g., Cherny et al., Neuron 30, 665-676 (2001)).

In the US the lifetime risk of AD is estimated to be 1:4-1:2. More than 14% of individuals older than 65 years have AD, and the prevalence increases to at least 40% in individuals older than 80 years. Prevalences similar to those in the United States have been reported in industrialized nations. Countries experiencing rapid increases in the elderly segments of their population have rates approaching those in the United States.

AD affects both men and women. Many studies indicate that the risk of AD is significantly higher in women than in men. Some authorities have postulated that this difference is due to the loss of the neurotrophic effect of estrogen in postmenopausal women. Other factors may also influence this relative difference.

AD is generally diagnosed by cognitive symptoms. In assessing AD, brain MRIs or CT scans show diffuse cortical and/or cerebral atrophy. These studies are also used to rule out other CNS disease. EEG and Tau protein tests are also used to confirm diagnosis and rule out other diseases that cause dementia.

The mainstay of AD therapy is the use of centrally acting cholinesterase inhibitors to palliate the depletion of ACh in the cerebral cortex and hippocampus. Because the clinical manifestations of AD are believed to be partly due to a loss of the cholinergic innervation to the cerebral cortex, compounds have been developed to palliate the cholinergic defect by interfering with the degradation of ACh by ACHE, the synaptic (or specific) form of cholinesterase. Some of the more recently available compounds are substances that inhibit also the nonsynaptic (or nonspecific) cholinesterases, which are frequently called BuChE.

ACHE inhibitors approved by the FDA for use in the early and intermediate stages of AD are tacrine (Cognex), donepezil (Aricept), rivastigmine (Exelon), and galantamine (galanthamine, Reminyl). Among these, only tacrine and rivastigmine also inhibit BuChE. This may be important for their therapeutic efficacy because BuChE levels increase during the course of AD and are present in some AD lesions, including senile plaques. At present, tacrine, is used seldom if at all because it has been superseded by other treatments.

An increasing number of clinical studies demonstrate that cholinesterase inhibition can have modest but detectable effects, such as improvement in cognitive performance, as measured by tools such as the Alzheimer's Disease Assessment Scale-cognitive subscale (ADAS-cog). More recent evidence indicates that ChEIs may also alleviate the noncognitive manifestations of AD. For example, they can ameliorate behavioral manifestations, as assessed by using tools such as the Neuropsychiatric Inventory, and they may improve the performance of activities of daily living, as evaluated by using the Progressive Deterioration Scale.

In general, the benefits are temporary because ChEIs do not address the underlying cause of the degeneration of cholinergic neurons, which continues during the disease. Although the increasingly large family of ChEIs was originally expected to help in only the early and intermediate stages of AD, results indicate that (1) they improve cognitive performance in advanced stages; (2) they significantly improve behavioral manifestations (eg, wandering, agitation, socially inappropriate behavior associated with advanced stages); and (3) they help in patients with presumed vascular components added to dementia due to AD, as well as in patients with the DLB, which often co-occurs or overlaps with AD (Lewy body variant of AD).

The ChEIs share a common profile of adverse effects, the most frequent of which are nausea, vomiting, diarrhea, and dizziness. These are typically dose related and can be mitigated with slow uptitration to the desired maintenance dose. Use of drugs whose absorption peaks are blunted by food (eg, rivastigmine) can further mitigate adverse effects and improve the tolerability of ChEI treatment.

NMDA antagonists are the newest class of agents indicated for the treatment of AD. As of October 2003, the only approved drug in this class is memantine. These agents may be used alone or combined with ACHE inhibitors. Accordingly, in some embodiments, compositions and methods of the present invention are used in combination with the above described agents for the therapeutic and/or prophylactic treatment of AD.

In preferred embodiments, the present invention provides a method of treating an Alzheimer's disease patient comprising administering to the Alzheimer's disease patient a composition comprising selenium (e.g., SEL-PLEX) under conditions such that symptoms (e.g., described above) of Alzheimer's disease in the patient are reduced. Although an understanding of the mechanism is not necessary to practice the present invention and the present invention is not limited to any particular mechanism of action, administering a composition comprising selenium (e.g., SEL-PLEX) to an Alzheimer's subject reduces symptoms associated with Alzheimer's through reducing the expression of genes that encode proteins involved in processing amyloid precursor protein (APP) (e.g., Nicastrin, presenilin 1, presenilin 2, calsenilin, Cathepsin B, Cathepsin D, Cathepsin Z, or Cathepsin O) (See Example 10). In other preferred embodiments, the expression of genes involved in the generation of beta amyloid peptide (e.g., Apbb1, Aplp 1, and Apba1) are aletered (e.g., reduced) using compositions and methods of the present invention. In some preferred embodiments, compositions and methods of the present invention are used as a prophylactic treatment in order to prevent Alzheimer's disease. In some embodiments, compositions and methods of the present invention are used in combination with other known therapeutic treatments (e.g., those described above) for the treatment Alzheimer's disease. In still other embodiments, the present invention provides a method of prophylactic and/or therapeutic treatment for Alzheimer's disease comprising co-administering to a subject a composition comprising selenium (e.g., SEL-PLEX), an Alzheimer's therapeutic and one or more anti-oxidants. In other embodiments, compositions and methods of the present invention are used to prevent and/or treat neurodegeneration associated with Alzheimer's disease comprising inhibiting expression of genes that encode proteins involved in processing amyloid precursor protein, genes involved in the generation of β-amyloid peptide, and complement associated genes (e.g., Nicastrin, presenilin 1, presenilin 2, calsenilin, Cathepsin B, Cathepsin D, Cathepsin Z, Cathepsin O, Apbb1, Aplp 1, Apba1; C1q, C1q alpha, C1q beta, C1q gamma, and C1qr, See Example 10). Thus, in some embodiments, the present invention provides a method of inhibiting the expression of genes involved in processing amyloid precursor protein in a subject comprising providing to the subject a composition comprising selenium (e.g., SEL-PLEX) under conditions such that the expression of genes involved in processing amyloid precursor protein are reduced. In some embodiments, the present invention provides a method of inhibiting the expression of genes involved in the generation of β-amyloid peptide in a subject comprising providing to the subject a composition comprising selenium under conditions such that the expression of genes involved in the generation of β-amyloid peptide are reduced. In some embodiments, the present invention provides a method of inhibiting the expression of complement genes (e.g., C1q, C1q alpha, C1q beta, C1q gamma, and C1qr) (See Example 10) in a subject comprising providing to the subject a composition comprising selenium under conditions such that the expression of complement genes are reduced. In preferred embodiments, the composition comprising selenium comprises SEL-PLEX. The composition comprising SEL-PLEX may also comprise other forms of selenium, for example, Sod-sel, thereby enhancing downregulation of expression of the above mentioned genes.

B. Amyotrophic Lateral Sclerosis (ALS).

In some embodiments of the present invention, compositions and methods of the present invention are utilized in the prophylactic or therapeutic treatment of amyotrophic lateral sclerosis (ALS). ALS is a devastating disorder of the anterior horn cells of the spinal cord and the motor cranial nuclei that leads to progressive muscle weakness and atrophy.

The frequency of ALS in the United States is approximately 5 cases per 100,000 population. ALS leads to death within a decade. In most cases, death occurs within 5 years. Some patients with familial, juvenile-onset ALS have been reported to survive for longer periods (2-3 decades). In the United States, ALS affects whites more often than nonwhites; the white-to-nonwhite ratio is 1.6:1. The ratio of ALS-affected males to females is 1.5:1. Onset occurs in the fourth to seventh decades of life.

ALS involves degeneration of motor neurons, resulting in progressive muscle wasting and weakness, culminating in paralysis, respiratory failure and death. Perhaps 10% of cases are familial, and of those, about 2-3% are caused by mutations in the gene encoding Cu/Zn superoxide dismutase-1 (SOD1), producing a toxic gain of function rather than loss of (catalytic) function (See, e.g., Rosen et al., Nature 362, 59-62 (1993)). The precise pathogenic mechanism is not clear, but implicated in motor neuron dysfunction and death are protein misfolding and aggregation, defective axonal transport, mitochondrial dysfunction and excitotoxicity via faulty glutamate reuptake into glial cells. Recent structural evidence suggests that some Cu/Zn SOD1 mutations result in destabilization of normal dimers of the enzyme and foster aggregation, forming amyloid or pores depending on the conditions, not unlike familial amyloid polyneuropathy (See, e.g., Hough et al., Proc. Natl. Acad. Sci. USA 101, 5976-5981 (2004); Koo et al., Proc. Natl. Acad. Sci. USA 96, 9989-9990 (1999)). Stabilization of dimers has therefore been proposed as a therapeutic intervention (See, e.g., Ray and Lansbury, Proc. Natl. Acad. Sci. USA 101, 5701-5702 (2004)).

A recent report on sporadic ALS (representing the vast majority of cases) revealed abnormal RNA editing in GluR2 subunits of glutamate receptors, producing increased $Ca^{2+}$ entry into neurons (See, e.g., Kawahara et al., Nature 427, 801 (2004); Lipton, Nat. Med. 10, 347 (2004)). This mechanism may contribute to neuronal demise, suggesting possible therapeutic targets, such as counteracting overly active calcium-permeable glutamate receptors or compensating for potentially dysfunctional RNA-editing enzymes.

Patients may have weakness of bulbar muscles or of single or multiple limb muscle groups. Presentation is not always bilateral or symmetrical. A predominantly bulbar form usually leads to more rapid deterioration and death. Limb weakness is predominantly distal. Weakness and atrophy of the intrinsic hand muscles are prominent. Weakness progresses to involve the forearms and shoulder girdle muscles and the lower extremities.

Involvement of both upper and lower motor neurons is characteristic. Patients develop variable hyperreflexia, clonus, spasticity, extensor plantar responses, and limb or tongue fasciculations. Wallerian degeneration of corticospinal and corticobulbar tracts may be demonstrated by MRI (high-intensity T2 lesions in frontal lobes) or in postmortem examination. Extraocular muscles and bladder and anal sphincter muscles typically are spared.

Nearly 10% of ALS cases are familial; the disease is transmitted in an autosomal dominant fashion. The copper/zinc SOD1 gene is mutated in 10-20% of these familial cases. Although the primary mechanism of SOD1-mediated neural injury is currently unknown, apoptosis, excitotoxicity, and oxidative stress are thought to play major roles in pathogenesis. Sporadic ALS shares clinical features with familial ALS. However, no SOD1 mutations or polymorphisms have been identified in these patients. Common pathways of disease pathogenesis may play a role, with different molecular abnormalities that lead to similar phenotypes.

Knockout mice for SOD1 exhibit typical progressive muscle atrophy and weakness with selective damage to motor neurons that closely resembles human ALS. There appears to be a causal relationship between mutant SOD1 secretion and neural toxicity (e.g., the mutant protein is not secreted). However, infusion of wild-type SOD in an ALS rat model significantly delays disease onset (See, e.g., J. Neurosci, 25, 108-117 (2005)). Additionally, it has been shown that a copper (Cu) chaperone is required for efficient loading of Cu into SOD (See, e.g., Nat. Neurosci, 5, 301-307 (2002)). Thus, the ability to maintain normal levels of wild-type SOD or to enhance expression or function of the same may provide a beneficial therapeutic effect for ALS subjects.

Furthermore, it has been shown that regressive numbers of basal forebrain cholinergic neurons appear in several areas of the brain of ALS subjects (See, e.g., Neurochem Int. 46, 357-368, (2005)). Thus, the ability to upregulate genes involved in basal forebrain cholinergic neuron growth and/or maintenance may provide beneficial effects for a subject with ALS.

Although an inflammatory process may be present, new evidence points toward multiple mechanisms that promote neuronal cell death in the CNS as the underlying basis for ALS. The recent demonstration of superoxide dismutase 1 (SOD1) mutations in human familial ALS and in murine ALS models supports the view that oxidative stress, mitochondrial dysfunction, and excitotoxicity pathways may be involved in the process of neuronal cell death.

ALS begins insidiously as weakness, atrophy, or fasciculations in 1 or more limbs. The manifestations are usually distal but gradually progress to involve the more proximal muscles. Fasciculations and atrophy of the tongue may be noted. Respiratory insufficiency is usually a late event. Physical examination reveals weakness and atrophy of the intrinsic hand muscles, hyperreflexia with extensor plantar responses, and clonus. Thigh fasciculations are common. Hyperreflexia can be variable and in some cases may be absent. Sensory involvement, if any, is minimal. Patients may present with an inability to write due to weakness. Gait function may be preserved.

Needle EMG and nerve conduction studies are the tests of choice for confirming the diagnosis of ALS. The confirmation of ALS is facilitated by demonstrating diffuse denervation signs, decreased amplitude of compound muscle action potentials, and normal conduction velocities. However, for a more detailed confirmation of ALS, more strict electrophysiologic criteria have been developed by a subcommittee of the World Federation of Neurology and are referred to as the "El Escorial" criteria for motor neuron disease.

Riluzole is the only medication that has shown treatment efficacy for ALS. Riluzole is thought to counteract the excitatory amino acid (glutaminergic) pathways, but its exact mechanism of action in ALS is unknown. That it prolongs tracheostomy-free survival compared to placebo has been shown in 2 randomized trials. No statistically significant difference in mortality rates was revealed at the end of these studies, however. In other clinical trials, creatine, human recombinant IGF-1, and ciliary neurotrophic factor (CNTF) also have shown promise.

Antispastic agents are also used to relieve spasticity and muscle spasms in patients with symptoms of limb stiffness. Examples include Baclofen (Lioresal) and Tizanidine (Zanaflex). In some embodiments, SEL-PLEX is used in combination with the above described agents.

Accordingly, in some embodiments, compositions and methods of the present invention are used in combination with other known therapeutic treatments (e.g., those described above) for the treatment ALS. Although an understanding of the mechanism is not necessary to practice the present invention and the present invention is not limited to any particular mechanism of action, administering a composition comprising selenium to a subject suspected of having ALS enhances the expression of genes (e.g., SOD genes, Lhx8, TGFβ-2 or other genes described herein) in the subject thereby treating ALS. In some embodiments, the present invention provides a method of enhancing the expression of SOD genes (e.g., SOD1 and SOD2) in a subject comprising providing to the subject a composition comprising selenium (e.g., SEL-PLEX) under conditions such that the expression of SOD genes are enhanced. In preferred embodiments, the composition comprising selenium comprises SEL-PLEX (See, Example 4). The composition comprising SEL-PLEX may also comprise other forms of selenium, for example, Sod-sel, thereby enhancing the downregulation of expression of SOD genes.

C. Parkinsons' Disease

In some embodiments, compositions and methods of the present invention (e.g., SEL-PLEX) are utilized for the prophylactic and therapeutic treatment of Parkinson's disease. Parkinson's disease (hereinafter, "PD") is a progressive neurodegenerative disorder associated with a loss of dopaminergic nigrostriatal neurons. PD is recognized as a common neurological disorder, affecting approximately 1% of individuals older than 60 years. Clinical features include resting tremor, rigidity, bradykinesia, and postural instability. The symptoms of PD are caused by selective and progressive degeneration of pigmented dopaminergic (DA) neurons in the substantia nigra pars compacta.

Neuropathologic findings in PD include a loss of pigmented dopaminergic neurons in the substantia nigra and the presence of Lewy bodies. The loss of dopaminergic neurons occurs most prominently in the ventral lateral substantia nigra. Approximately 60-80% of dopaminergic neurons are lost before clinical symptoms of PD emerge. Lewy bodies are concentric, eosinophilic, cytoplasmic inclusions with peripheral halos and dense cores. The presence of Lewy bodies within pigmented neurons of the substantia nigra is characteristic, but not pathognomonic, of idiopathic PD. Lewy bodies also are found in the cortex, nucleus basalis, locus ceruleus, intermediolateral column of the spinal cord, and other areas. Lewy bodies are not specific to PD, as they are found in some cases of atypical parkinsonism, Hallervorden-Spatz disease, and other disorders. Incidental Lewy bodies are found at postmortem in patients without clinical signs of parkinsonism. The prevalence of incidental Lewy bodies increases with age. Incidental Lewy bodies have been hypothesized to represent the presymptomatic phase of PD. Alpha-synuclein is a structural component of Lewy bodies. Lewy bodies stain for alpha-synuclein and most also stain for ubiquitin.

The basal ganglia motor circuit modulates cortical output necessary for normal movement. Signals from the cerebral cortex are, processed through the basal ganglia-thalamocortical motor circuit and return to the same area via a feedback pathway. Output from the motor circuit is directed through the internal segment of the globus pallidus (GPi) and the substantia nigra pars reticulata (SNr). This inhibitory output is directed to the thalamocortical pathway and suppresses movement.

Two pathways exist within the basal ganglia circuit; they are referred to as the direct and indirect pathways. In the direct pathway, outflow from the striatum directly inhibits GPi and SNr. The indirect pathway comprises inhibitory connections between the striatum and the external segment of the globus pallidus (GPe) and the GPe and the subthalamic nucleus (STN). The subthalamic nucleus exerts an excitatory influence on the GPi and SNr. The GPi/SNr sends inhibitory output to the ventral lateral (VL) nucleus of the thalamus. Striatal neurons containing D1 receptors constitute the direct pathway and project to the GPi/SNr. Striatal neurons containing D2 receptors are part of the indirect pathway and project to the GPe.

Dopamine is released from nigrostriatal (SNc) neurons to activate the direct pathway and inhibit the indirect pathway. In PD, decreased striatal dopamine causes increased inhibitory output from the GPi/SNr. This increased inhibition of the thalamocortical pathway suppresses movement. Via the direct pathway, decreased striatal dopamine stimulation causes decreased inhibition of the GPi/SNr. Via the indirect pathway, decreased dopamine inhibition causes increased inhibition of the GPe, resulting in disinhibition of the STN. Increased STN output increases GPi/SNr inhibitory output to the thalamus.

Rare hereditary forms of PD have provided insight into the molecular pathways of this disorder (See, e.g., Hardy et al., Lancet Neurol. 2, 221-228 (2003)). Mutations in at least four genes have been linked to PD, including α-synuclein (PARK1), parkin (PARK2), DJ-1 (PARK7), and PTEN (phosphatase and tensin homolog deleted on chromosome 10)-induced kinase 1 (PINK1, also known as PARK6) (See, e.g., Polymeropoulos, et al, Science 276, 2045-2047 (1997); Kitada et al., Nature 392, 605-608 (1998); Bonifati et al., Science 299, 256-259 (2003); Valente et al., Science 304, 1158-1160 (2004)). Parkin is an E3 ligase, catalyzing the addition of ubiquitin to specific substrates that targets them for degradation by the ubiquitin-proteasome system (UPS). Parkin is a target of oxidative and nitrosative stress in sporadic PD. Cysteine residues in the RING domains are sensitive to nitrosative and oxidative modifications, which alter protein function. New findings indicate that parkin's E3 ligase activity is modified by NO, thus linking environmental stress to a molecular abnormality and a clinical phenotype similar to that seen in hereditary forms of PD (See, e.g., Chung et al, Science 304, 1328-1331 (2004)).

In some embodiments, compositions of the present invention (e.g., SEL-PLEX) are administered with other therapeutic interventions for treating PD. The present invention is not limited to particular therapeutic interventions useful in treating PD. In some embodiments, compositions of the present invention are administered along with surgical intervention in the treatment of PD. Surgical interventions useful in the treatment of PD include, but are not limited to, stereotactic surgery (e.g., thalamotomy, thalamic deep brain stimulation, pallidotomy, pallidal stimulation, subthalamotomy, subthalamic stimulation, and neuronal transplantation). In some embodiments, compositions of the present invention are administered along with dopamine prodrugs in the treatment of PD. Dopamine prodrugs useful in treating PD include, but are not limited to, levadopa/PDI and levodopa/carbidopa (e.g., Sinemet, Sinemet CR). Current treatments, such as administration of L-DOPA to produce dopamine, are only symptomatic and do not stop or delay the progressive loss of neurons. In fact, some studies have suggested that oxidative injury via dopamine may lead to further neuronal damage (See, e.g., Xu et al., Nat. Med. 8, 600-606 (2002)). Thus, in some embodiments, compositions of the present invention are administered with a PD therapeutic agent (e.g., L-DOPA) and an anti-oxidant. Anti-oxidants suitable for co-administration are described herein.

In some embodiments, compositions comprising selenium of the present invention are administered along with dopamine agonists in the treatment of PD. Dopamine agonsts useful in treating PD include, but are not limited to, apomorphine (e.g., Apokyn), bromocriptine (e.g., Parlodel), pergolide (e.g., Permax), pramipexole (e.g., Mirapex), and ropinirole (e.g., Requip). In some embodiments, the compounds of the present invention are administered with catechol-O-methyltransferase (COMT) inhibitors in the treatment of PD. COMT inhibitors useful in the treatment of PD include, but are not limited to, tolcapone (e.g., Tasmar), and entacapone (e.g., Comtan). In some embodiments, the compounds of the present invention are administered along with anticholinergics in the treatment of PD. Anticholinergics useful in the treatment of PD include, but are not limited to, trihexyphenidyl (e.g., Artane, Trihexy), and benztropine mesylate (e.g., Cogentin). In some embodiments, the compounds of the present invention are administered along with MAO-B inhibitors in the treatment of PD. MAO-B inhibitors useful in the treatment of PD include, but are not limited to, selegiline (e.g., Eldepryl). In some embodiments, the compounds of the present invention are administered along with amantadine (e.g., Symmetrel) in the treatment of PD.

D. Huntington's Disease

In some embodiments, compositions and methods of the present invention (e.g., SEL-PLEX) are utilized for the prophylactic and therapeutic treatment of Huntington's Disease. Huntington disease (hereinafter, "HD") is an autosomal dominant inherited neurodegenerative disorder affecting 1 in 10,000 individuals. It is caused by an insertion of multiple CAG repeats in the huntingtin gene. This results in an N-terminal polyglutamine (polyQ) expansion of the large protein huntingtin (Htt), similar to other polyQ-related neurodegenerative disorders. Disease severity depends on the length of the polyQ stretch, with repeats greater than 40 clearly linked to HD. The polyQ expansion is thought to confer a toxic gain of function with selective loss of neurons in the striatum and cerebral cortex.

Characteristic features of HD include involuntary movements, dementia, and behavioral changes. Neuropathology in HD occurs within the neostriatum, in which gross atrophy of the caudate nucleus and putamen is accompanied by selective neuronal loss and astrogliosis. Marked neuronal loss also is seen in deep layers of the cerebral cortex. Other regions, including the globus pallidus, thalamus, subthalamic nucleus, substantia nigra, and cerebellum, show varying degrees of atrophy depending on the pathologic grade.

The function of huntingtin is not known. Normally, it is located in the cytoplasm. The association of huntingtin with the cytoplasmic surface of a variety of organelles, including transport vesicles, synaptic vesicles, microtubules, and mitochondria, raises the possibility of the occurrence of normal cellular interactions that might be relevant to neurodegeneration. N-terminal fragments of mutant huntingtin accumulate and form inclusions in the cell nucleus in the brains of patients with HD, as well as in various animal and cell models of HD.

Patients with HD have a mixed pattern of neurological and psychiatric abnormalities. Chorea, a state of excessive, spontaneous movements, irregularly timed, randomly distributed, and abrupt, is a characteristic feature of HD. Severity of chorea may vary from restlessness with mild intermittent exaggeration of gesture and expression, fidgeting movements of the hands, and unstable dancelike gait to a continuous flow of disabling violent movements. Additional clinical features of HD include, for example, bradykinesia, akinesia, dystonia, eye movement abnormalities, dementia, depression, and other psychiatric manifestations.

Calpains are proteases that have a key role in Huntington proteolysis and disease pathology. Calpain family members, including Calpain-5, have increased levels or are activated in HD tissue culture and transgenic mouse models (See, e.g., J Biol Chem, 279, 20211-20220 (2004)).

Compositions and methods of the present invention were analyzed to determine if they were capable of altering the expression levels of calpain genes. Compositions comprising various forms of selenium (e.g., SeM, Sod-sel, and SEL-PLEX) were administered to subjects and the expression levels of calpain genes monitored. The expression level of calpain-5 was altered by treatment in the following ways: free selenomethionine (SM)+1.32*, Sod-sel−1.07, SEL-PLEX−1.44*.

In some embodiments, compositions comprising selenium of the present invention (e.g., SEL-PLEX) are used for treating HD. In preferred embodiments, the present invention provides a method of treating a subject with HD comprising administering to the subject a composition comprising selenium under conditions such that the expression of a calpain gene is reduced. In some embodiments, the calpain gene is calpain-5. In some embodiments, compositions of the present invention are administered with other therapeutic agents for treating HD. The present invention is not limited to particular therapeutic agents useful in treating HD. In some embodiments, the compositions comprising selenium are administered with anticonvulsant medication in the treatment of HD. Anticonvulsant medication useful in treating HD include, but are not limited to, valproic acid (e.g., Depakote, Depakene, and Depacon) and benzodiazepines such as clonazepam (e.g., Klonopin). In some embodiments, the compositions comprising selenium are administered with antipsychotic medication in the treatment of HD. Antipsychotic medication useful in treating HD include, but are not limited to, risperidone (e.g., Risperdal), and haloperidol (e.g., Haldol In some embodiments, the compositions comprising selenium are administered with rauwolfia alkaloids in the treatment of HD. Rauwolfia alkoids useful in treating HD include, but are not limited to, resperine. In some embodiments, the compositions comprising selenium are administered with antidepressants in the treatment of HD. Antidepressants useful in treating HD include, but are not limited to, paroxetine (e.g., Paxil).

E. Multiple Sclerosis

In some embodiments, compositions and methods of the present invention are utilized in the treatment of multiple sclerosis. Multiple sclerosis (MS) is an inflammatory, demyelinating disease of the central nervous system (CNS). MS lesions, characterized by perivascular infiltration of monocytes and lymphocytes, appear as indurated areas in pathologic specimens; hence, the term "sclerosis in plaques."

MS is a dynamic disease, with almost constant lesion formation and a progressive clinical course leading to physical disability. For every 8-10 new lesions detected on magnetic resonance imaging (MRI), only one clinical manifestation typically can be demonstrated. Patients with relapsing remitting MS have an average of 20 new lesions per year and one or two clinical exacerbations.

With the advent of MRI, the ability to confirm the diagnosis of MS has improved dramatically. MRI characteristically shows lesions of high T2 signal intensity of variable location in the white matter of the brain, brain stem, optic nerves, or spinal cord. In typical cases, the lesions tend to occur in periventricular areas and may occur in the corpus callosum. Newer MRI techniques (e.g., magnetization transfer, fluid attenuated inversion recovery (FLAIR), MR spectroscopy (MRS)) promise to yield important information regarding MS heterogeneity, prognosis, and treatment effects.

Despite intensive efforts at finding the source of the disease, no etiologic agent for MS has been identified. The disease presumably can be exacerbated by hormonal changes during the postpartum period. Some argue that MS could be a heterogeneous disorder triggered by several different environmental agents. In fact, only 1 of every 4 MS attacks is associated with a viral infection.

The disease can present in different forms, such as primary progressive, relapsing remitting, relapsing progressive, and secondary progressive phenotypes. Genetic susceptibility factors may play a role, as the disease is more common in Caucasian populations living in northern latitudes. This susceptibility may be part of a complex and heterogeneous group of factors that have an impact, along with environmental factors, on the initiation and maintenance of disease. In addition, migration to high-risk areas before age 15 years is known to increase the risk of developing MS, lending further support to the environmental factor hypothesis.

MS is characterized by perivenular infiltration of lymphocytes and macrophages in the parenchyma of the brain, brain stem, optic nerves, and spinal cord. Expression of adhesion molecules on the surface seems to underlie the ability of these inflammatory cells to penetrate the blood-brain barrier. The elevated immunoglobulin G (IgG) level in the cerebrospinal fluid (CSF), which can be demonstrated by an oligoclonal band pattern on electrophoresis, suggests an important humoral (ie, B cell activation) component to MS. In fact, variable degrees of antibody-producing plasma cell infiltration have been demonstrated in MS lesions (see Image 1). Molecular studies of the white matter plaque tissue have shown that interleukin (IL)-12, a potent pro-inflammatory substance, is expressed at high levels in early formed lesions.

In the US, MS has a prevalence of nearly 350,000 cases in the United States alone. Every year, approximately 10,000 persons are newly diagnosed with MS. More than 1 million worldwide are affected. MS causes considerable disability in the working age group. People with MS usually die of complications rather than of MS itself, including recurrent infections (especially in bedridden patients). Patients with MS have an average life expectancy 7 years shorter than that of the general population.

MS presents more often in populations of northern European ancestry. Whether disease severity also may be accounted for by racial differences is controversial. The concordance rate for MS is 20-40% among monozygotic twins, suggesting the presence of predisposing genetic factors of non-Mendelian inheritance.

MS affects females more than males (1.6-2:1), but the basis for this difference is unknown. This ratio is even higher (3:1) among patients in whom onset of MS is before age 15 years or after age 50 years, suggesting a hormonal component to the disease process. Males have a greater tendency to develop primary progressive MS, while females tend to experience more relapses. MS most commonly afflicts people between the ages of 18 and 50 years, but any age group can be affected.

C4d-immunoreacive complement-activated oligodendrocytes (C4d-CAOs) have been described in MS (See, e.g., Schwab and McGeer, Experimental Neurology, 174, 81-88 (2002)). C4d-CAOs were reported to delineate miniature MS plaques of 300-500 µm. In large MS lesions, immunoreactive fibers corresponding to the C1q-C9 components of the complement cascade were identified indicating that complete activation of the complement cascade is present with MS lesions. Association of C4d-CAOs with areas of demyelination demonstrated a direct attack on oligodendroglial cells by the early complement components as an initiating event in MS. Furthermore, incomplete complement activation idicated that this step may be reversible (See, e.g., Schwab and McGeer, Experimental Neurology, 174, 81-88 (2002)).

Drug therapy seeks to delay progression to disability, reduce relapse rate, increase the number of relapse-free patients, and increase the time to first relapse as well as decrease MRI lesion burden, atrophy, and "T1 holes," or presence of new lesions. Accordingly, in some embodiments, compositions comprising selenium of the present invention (e.g., SEL-PLEX) are used for treating and/or preventing MS. In preferred embodiments, the present invention provides a method of treating a subject with MS comprising administering to the subject a composition comprising selenium under conditions such that the expression of a complement gene is reduced. In some embodiments, the complement gene is comprises C1q, C1q alpha, C1q beta, C1q gamma and/or C1qr. In some embodiments, compositions of the present invention are administered with other therapeutic agents for treating MS. The present invention is not limited to particular therapeutic agents useful in treating MS. In some embodiments, the compositions comprising selenium are administered with immunomodulators (e.g., Interferon beta-1a (Avonex), Interferon beta-1a (Rebif), Interferon beta-1b (Betaseron), Glatiramer acetate (Copaxone), and Natalizumab (Tysabri)), which delay progression to disability and reduce the number of new MS lesions by MRI; corticosteroids (e.g., methylprednisolone), which are used to reduce acute inflammation and expedite recovery from acute exacerbations of MS; and immunosuppressors (e.g., Mitoxantrone (Novantrone), Cyclophosphamide (Cytoxan, Neosar), Azathioprine (MURAN), Methotrexate (Rheumatrex), which are used to suppress immune reactions. Additional drugs may be used to treat common secondary conditions such as depression, spasticity, tonic spasms, fatigue, urinary dysfunction, and erectile dysfunction. In some embodiments, compositions comprising selenium are used in combination with the above described agents.

II. Cognitive Function

The central nervous system consists of the brain and the spinal cord. All other nerves in the body comprise the peripheral nervous system. Efferent nerves carry messages from the central nervous system to all parts of the body (the periphery). Afferent nerves carry information such as pain intensity from the periphery to the central nervous system. There are two types of efferent nerves: somatic, which go to skeletal muscles, and autonomic, which go to smooth muscles, glands and the heart. Messages in the form of electrical activity are conducted along the nerve fibers or axons. Between the terminus of the axon and the muscle or gland that the nerve controls (innervates), there is a gap called the synapse or synaptic cleft. When the conducted electrical impulse (action potential) reaches the nerve terminus, it provokes the release of chemicals called neurotransmitters. These chemicals diffuse across the synaptic cleft and react with a specialized structure (receptor) on the postjunctional membrane. The receptor is then said to be activated or excited, and its activation triggers a series of chemical events resulting ultimately in a biological response such as muscle contraction. The processes involving neurotransmitter release, diffusion and receptor activation are referred to collectively as transmission. There are many types of transmission, and they are named for the specific neurotransmitter involved. Thus, cholinergic transmission involves the release of the neurotransmitter, acetylcholine, and its activation of the postsynaptic receptor. Things that bind to and activate receptors are called agonists. Thus, acetylcholine is the endogenous agonist for all cholinergic receptors.

After leaving the central nervous system, somatic nerves to skeletal muscles have only one synapse, namely, that between the nerve terminus and the muscle it innervates. The neurotransmitter at that synapse is acetylcholine. Thus, this myo- (for muscle)-neural junction is one site of cholinergic transmission. The postjunctional receptor is called the motor end plate. Autonomic nerves, in contrast to somatic nerves, have an additional synapse between the central nervous system and the innervated structure (end organ). These synapses are in structures called ganglia, and these are nerve-to-nerve junctions instead of nerve-to-end organ junctions. Like somatic nerves, however, autonomic nerves also have a final nerve-to-end organ synapse. The neurotransmitter in autonomic ganglia is also acetylcholine; hence, this represents another site of cholinergic transmission. The motor end plate and the ganglionic receptors can also be activated by exogenously added nicotine. Thus, nicotine is an agonist for this particular subfamily of cholinergic receptors which are called nicotinic, cholinergic receptors.

There are two anatomically and functionally distinct divisions of the autonomic nervous system: the sympathetic division and the parasympathetic division. The preganglionic fibers of the two divisions are functionally identical, and they innervate nicotinic, cholinergic receptors in ganglia to initiate action potentials in the postganglionic fibers. Thus, all ganglia are created pretty much equal. Only the postganglionic fibers of the parasympathetic division, however, are cholinergic. The postganglionic fibers of the sympathetic division generally, but not always, secrete norepinephrine. The cholinergic receptors innervated by the postganglionic fibers of the parasympathetic division of the autonomic nervous system can also be activated by exogenously added muscarine, an agonist found in small amounts in the poisonous mushroom, Amanita muscaria. These constitute a second subset of cholinergic receptors which are called muscarinic, cholinergic receptors.

Although the receptors in ganglia and the motor end plate both respond to nicotine, they actually constitute two distinct subgroups of nicotinic receptors. Each of the three families of cholinergic receptors can be blocked by specific receptor antagonists to prevent their activation by endogenous acetylcholine or added agonists. Thus, specific blockers are known for cholinergic, muscarinic receptors innervated by postganglionic fibers of the parasympathetic division of the autonomic nervous system, for cholinergic, nicotinic receptors in both sympathetic and parasympathetic ganglia, and for cholinergic nicotinic receptors at the myoneural junction (motor end plates) of the somatic nervous system. When these receptors are blocked, the on-going biological activity associated with their normal and continuous activation is lost. For example, blockade of the motor end plate leads to generalized, flaccid paralysis.

There are some anomalous fibers in the sympathetic division of the autonomic nervous system. For example, the sympathetic postganglionic nerves that go to sweat glands are cholinergic instead of adrenergic, like most other sympathetic fibers, and they innervate muscarinic receptors. The sympathetic nerve to the adrenal gland innervates a receptor that is nicotinic like all autonomic ganglia, but there is no postganglionic fiber. The gland itself is analogous to a postganglionic sympathetic fiber, but, instead of secreting a neurotransmitter, it secretes epinephrine and norepinephrine into the blood stream, where they function as hormones. These hormones activate adrenergic receptors throughout the body. Nicotinic and muscarinic receptors in the central nervous system are incompletely understood.

Cholinergic drugs are medications that produce the same effects as the parasympathetic nervous system. Cholinergic drugs produce the same effects as acetylcholine. Acetylcholine is the most common neurohormone of the parasympathetic nervous system, the part of the peripheral nervous system responsible for the every day work of the body. While the sympathetic nervous system acts during times of excitation, the parasympathetic system deals with everyday activities such as salivation, digestion, and muscle relaxation.

The cholinergic drugs may be used in several ways. The cholinergic muscle stimulants are used to diagnose and treat myathenia gravis, a disease that causes severe muscle weakness. This class of drugs includes ambenonium chloride (Mytelase), edrophonium chloride (Tensilon), neostigmine (Prostigmine), and piridogstimina (Mestinn). These drugs are also widely used in surgery, both to reduce the risk of urinary retention, and to reverse the effects of the muscle relaxant drugs that are used in surgery.

Cholinergic drugs are also used in control of glaucoma, a disease that is caused by increased pressure inside the eye. The most common drugs used for this purpose are demecarium (Humorsol) and echthiophate (Phospholine iodide).

Cholinergic drugs usually act in one of two ways. Some directly mimic the effect of acetylcholine, while others block the effects of acetylcholinesterase. Acetylcholinesterase is an enzyme that destroys naturally occurring acetylcholine. By blocking the enzyme, the naturally occurring acetylcholine has a longer action. Cholinergic drugs are available only by prescription. They may be available as eye drops, capsules, tablets, or injections.

Cognitive function has been demonstrated to decline or deteriorate in several diseases, such as MS, Alzheimer's disease, Parkinson's disease, Huntington's disease, ALS, among others.

In MS, for example, the cognitive function most likely to be affected appears to be memory. Other cognitive functions frequently affected in subjects with neurodegenerative disease include speed of information processing, executive functions (planning and prioritizing), visuospatial functions (impairment in visual perception and constructional abilities), abstract reasoning and problem-solving, and attention and concentration-especially sustained attention and ability to divide attention between separate tasks. One of the most vexing cognitive deficits seen in MS is word-finding difficulty the experience of having a word on the tip of your tongue but not being able to remember it.

The first signs of cognitive dysfunction or decline may be subtle. The person may have difficulty in finding the right words to say, or trouble remembering what to do on the job or during daily routines at home. Decisions that once were easy now demonstrate poor judgment. Often, the family becomes aware of the problem first, noticing changes in behavior or personal habits. Cognitive dysfunction can have an impact on role performance at home and at work. Cognitive function can also be affected by aging or medications.

Substantial biologic evidence supports the importance of estrogen to cognitive function. Estrogen receptors have been identified throughout the brain, and appear particularly concentrated in the basal forebrain. The basal forebrain is of special interest since it is the major source of cholinergic innervation to the hippocampus. The cholinergic system is a neurotransmitter system important for regulation of memory and learning, while the hippocampus is the primary region of the brain mediating cognitive function. In experiments using animal models and cell lines, several mechanisms have been identified whereby estrogen may influence cognitive function.

Basal forebrain cholinergic neurons (BFCNs) are involved in cognitive functions such as learning and memory and are affected in several neurodegenerative diseases, such as Alzheimer's disease (AD). The LIM homeobox protein 8 gene (Lhx8), is important for the proper development and maintenance of BFCNs (See, e.g., Mori et al., Eur. J. Neurosci., 19, 3129 (2004)).

Mice with a null mutation in the Lhx8 gene are deficient in the development of forebrain cholinergic neurons (Zhao et al., Proc. Nat. Acad. Sci. 100: 9005 (2003)). Lhx8 mutants lacked the nucleus basalis, a major source of the cholinergic input to the cerebral cortex.

Using compositions and methods of the present invention, the observed expression level of Lhx8 was not significantly different between Se-deficient subjects and that of subjects receiving certain forms of selenium (e.g., SeM or Sod-sel). However, when subjects were administered (e.g., received a dietary supplement) a composition comprising SEL-PLEX, the expression of Lhx8 was upregulated 12.9-fold ($p<0.01$) (See Example 5). Thus, in some preferred embodiments, the present invention provides a method of maintaining and/or stabilizing neurologic function (e.g., cholinergic neuron growth and function associated with cognitive function) in a subject comprising administering to the subject a composition comprising SEL-PLEX. In preferred embodiments, SEL-PLEX is administered to the subject under conditions such that the expression of Lhx8 is enhanced. In some preferred embodiments, compositions and methods of the present invention are used as a prophylactic treatment in order to prevent the loss of cognitive function. Although an understanding of the mechanism is not necessary to practice the present invention and the present invention is not limited to any particular mechanism of action, preventing loss of cognitive function may occur due to promoting development of basal forebrain cholinergic neurons or simply the maintenance (e.g., lack of apoptosis) of basal forebrain cholinergic neurons. In some embodiments, a composition comprising SEL-PLEX is administered to a subject suspected of having myasthenia gravis for the treatment of myathenia gravis. In some embodiments, a composition comprising selenium (e.g., SEL-PLEX) is co-administered in combination with other known therapeutic treatments (e.g., those described above) for the treatment of myasthenia gravis. In still other embodiments, the present invention provides a method of prophylactic and/or therapeutic treatment for myathenia gravis comprising co-administering to a subject a composition comprising selenium (e.g., SEL-PLEX) and a cholinergic muscle stimulant.

The product of another gene, transforming growth factor beta 2 (TGF-$\beta$2), is known to increase neuronal proliferation in the developing cerebellum (See, e.g., Elvers et al., Mechanisms of Development, 122, 587 (2004)). Furthermore, it has been shown that TGF-$\beta$2 is a growth and survival factor for granule cell precursors in the cerebellum and that antibody-mediated neutralization of endogenous TGF-$\beta$2 represses proliferation of cerebellar granule cell precursors and induces neurodegeneration. It has also been demonstrated that knocking out (e.g., deleting) TGF-$\beta$2 is a lethal phenotype with TGF-$\beta$2 deficient mice developing a range of defects and dying before development of the cerebellum occurs (See, e.g., Sanford et al., Development, 124, 2659 (1997)).

The expression level of TGF-$\beta$2 was not altered, compared to controls, in subjects administered certain forms of selenium (e.g., SeM or Sod-Sel). However, when subjects were administered (e.g., received a dietary supplement) a composition comprising SEL-PLEX, the expression TGF-$\beta$ was upregulated 2.4-fold (See Example 5). Thus, in some embodiments, the present invention provides a method of increasing cerebellum function in a subject comprising administering to the subject a composition comprising SEL-PLEX. Although an understanding of the mechanism is not necessary to practice the present invention and the present invention is not limited to any particular mechanism of action, administering a composition comprising selenium (e.g., a daily dietary supplement comprising SEL-PLEX) to a subject increases neuronal activity (e.g., increases neuronal proliferation) and/or inhibits neurodegeneration. In some preferred embodiments, the present invention provides a method of maintaining and/or stabilizing neurologic function (e.g., cholinergic neuron growth and function) in a subject comprising administering to the subject a composition comprising SEL-PLEX under conditions such that the expression of TGF-$\beta$ is enhanced. In some preferred embodiments, compositions comprising SEL-PLEX are used as a prophylactic treatment in order to prevent the loss of cognitive function (e.g., by upregulation of genes such as Lhx8 and TGF-$\beta$ that enhance neurologic function).

III. Retardation of Age-Associated Gene Expression

Aging of the brain leads to impairments in cognitive function and motor skills, and is a major risk factor for several common neurological disorders such as Alzheimer disease (AD) and Parkinson disease (PD). Recent studies suggest that normal brain aging is associated with subtle morphological and functional alterations in specific neuronal circuits, as opposed to large-scale neuronal loss (See, e.g., Morrison and Hof, Science 278, 412-419 (1997)). In fact, aging of the central nervous system in diverse mammalian species shares many features, such as atrophy of pyramidal neurons, synaptic atrophy, decrease of striatal dopamine receptors, accumulation of fluorescent pigments, cytoskeletal abnormalities, and reactive astrocytes and microglia (See, e.g., Finch and Roth, in Basic Neurochemistry (eds Seigel, G., Agranoff, J. B., Albers, W. R. W., Fisher, S. K. & Uhler, M. D.) 613-633 (Lippincott-Raven, Philadelphia, 1999).

Postulated mechanisms of CNS aging include instability of nuclear and mitochondrial genomes (See, e.g., Gaubatz, in Molecular Basis of Aging (ed. Macieira-Coelho, A.) 71-182 (CRC Press, Boca Raton, 1995)), neuroendocrine dysfunction (See, e.g., McEwen, Front. Neuroendocrinol. 20, 49-70 (1998)), production of reactive oxygen species (See, e.g., Sohal and Weindruch, Science 273, 59-63 (1996)), altered calcium metabolism (See, e.g., Disterhoft et al., Hypothesis of Aging and Dementia (New York Academy of Sciences Press, New York, 1994), and inflammation-mediated neuronal damage (See, e.g., Blumenthal, J. Gerontol. Biol. Sci. Med. Sci. 52, B1-B9 (1997)). Caloric restriction, the only intervention shown to slow the intrinsic rate of aging in mammals (See, e.g., Weindruch and Walford, The Retardation of Aging and Disease by Dietary Restriction (C. C. Thomas, Springfield, Ill., 1988), retards age-related declines in psychomotor and spatial memory tasks (See, e.g., Ingram et al., J. Gerontol. 42, 78-81 (1987)), reduces the age-associated loss of dendritic spines (See, e.g., Moroi-Fetters et al., Neurobiol. Aging 10, 317-322 (1989)) and reduces neuronal degeneration in models of PD (See, e.g., Duan and Mattson, J. Neurosci. Res. 57, 195-206 (1999)).

Brain aging has been characterized at the molecular level (e.g., through gene-expression profiling of the aging neocortex and cerebellum in mice (See, e.g., Lee et al., Nature Genetics, 25, 294-297 (2000)). Aged mice display expression of genes indicative of an inflammatory response, oxidative stress and reduced neurotrophic support. At the transcriptional level, brain aging in mice displays parallels with human neurodegenerative disorders (See, e.g., Lee et al., Nature Genetics, 25, 294-297 (2000)).

In aged mice, a concerted induction of the complement cascade genes C4, C1qa, C1qb and C1qc, was observed (See, e.g., Lee et al., Nature Genetics, 25, 294-297 (2000)). As described elsewhere herein, these genes are part of the humoral immune system involved in inflammation and cytolysis. Production of complement proteins in the brain, which leads to the generation of proinflammatory peptide fragments, contributes to neuronal damage associated with stroke (See, e.g., Huang et al., Science 285, 595-599 (1999)) and has been observed in the striatum of aged rats (See, e.g., Pasinetti et al., Synapse 31, 278-284 (1999)).

Additionally, a coordinated induction of the genes encoding cathepsins D, S, and Z were observed in aged mice (See, e.g., Lee et al., Nature Genetics, 25, 294-297 (2000)). Cathepsins are major components of the lysosomal proteolytic system. Cathepsins have been implicated in the processing of amyloid precursor protein (APP) to amyloid $\beta$-peptides and are induced in the brains of Alzheimer's disease patients (See, e.g. Lemere et al., Am. J. Pathol. 146, 848-860 (1995)).

Aging is well known to be associated with increased oxidant generation (See, e.g., Peinado et al., Anat Rec, 247, 420 (1997)). For example, highly reactive oxygen species (ROS) promote a wide spectrum of cell damage, including DNA damage, lipid peroxidation, alteration of intracellular redox balance and inactivation of enzymes. A key host mechanism in the defense against ROS is performed by the family of Glutathione-S-Transferases (GSTs) that protect against the by-products of oxidative stress through a variety of reactions (See, e.g., Hayes et al., Annu. Rev. Phramacol. Toxicol., 45, 51, (2004)).

Accordingly, in some preferred embodiments, the present invention provides a method of retarding age related expression of complement associated genes (e.g., C1q, C1q alpha, C1q beta, C1q gamma, or C1qr) in a subject comprising administering to the subject a composition comprising SEL-PLEX (e.g., a dietary supplement comprising SEL-PLEX) under conditions such that complement associated gene expression is reduced (See Example 10). In some embodiments, the present invention provides a prophylactic or therapeutic treatment for stroke comprising administering to a subject at risk of stroke (e.g., an elderly person) a composition comprising selenium (e.g., SEL-PLEX) under conditions such that the expression of complement genes (e.g., C1q, C1q alpha, C1q beta, C1q gamma, or C1qr) are reduced. In other preferred embodiments, the present invention provides a method of retarding age related expression of cathepsin gene expression (e.g., Cathepsin D, Cathepsin S, or Cathepsin Z) in a subject comprising administering to the subject a composition comprising SEL-PLEX (e.g., a dietary supplement comprising SEL-PLEX) under conditions such that cathepsin gene expression is reduced (See Example 10). In some embodiments, the present invention provides a method of treating an Alzheimer's disease patient comprising administering to the Alzheimer's disease patient a composition comprising selenium (e.g., SEL-PLEX) under conditions such that symptoms of Alzheimer's disease in the patient are reduced. Although an understanding of the mechanism is not necessary to practice the present invention and the present invention is not limited to any particular mechanism of action, administering a composition comprising selenium (e.g., SEL-PLEX) to an Alzheimer's subject reduces symptoms associated with Alzheimer's through reducing the expression of cathepsin genes (e.g., Cathepsin D, Cathepsin S, or Cathepsin Z). In some embodiments, compositions and methods of the present invention are used as a prophylactic treatment in order to prevent age-associated gene expression. In some embodiments, a composition comprising selenium (e.g., SEL-PLEX) is administered to a subject in combination with a calorie restricted diet in order to prevent aging (e.g., attenuate age-associated gene expression). In some preferred embodiments, the present invention provides a method of altering neuronal circuit changes (e.g., described above) associated with age comprising administering to a subject a composition comprising selenium (e.g., SEL-PLEX) under conditions such that the expression of Lhx8 is enhanced and/or elevated (See Example 6). Although an understanding of the mechanism is not necessary to practice the present invention and the present invention is not limited to any particular mechanism of action, enhanced and/or elevated expression of Lhx8 stimulates the proper development and/or works to maintain levels basal forebrain cholinergic neurons (BFCNs).

It has further been shown that there is a significant up-regulation of certain transcription factors in response to a calorie restricted diet, itself providing age retardation (See, e.g., Lee et al., Nature Genetics, 25, 294-297 (2000)). For example, homeobox (Hox) transcription factors were upregulated, which are proposed to be involved in neural development. Using compositions and methods of the present invention, it was demonstrated that several Hox transcriptions factors were upregulated in a subject administered a composition comprising selenium (e.g., SEL-PLEX), Although an understanding of the mechanism is not necessary to practice the present invention and the present invention is not limited to any particular mechanism of action, enhanced and/or elevated expression of Hox factors functions to maintain normal neural activity in an aging subject.

IV. The Endocrine System and Diabetes

In some embodiments of the present invention, compositions and methods of the present invention are utilized in the treatment of diabetes. Diabetes mellitus is a chronic disease that requires long-term medical attention both to limit the development of its devastating complications and to manage them when they do occur. It is a disproportionately expensive disease; patients diagnosed with diabetes accounted for 6.2% of the US population in 2002, or 18.2 million people. In that year, the per capita cost of healthcare for people with diabetes was $13,243 for people with diabetes and $2560 for people without diabetes.

The 2 basic types of diabetes mellitus are type 1 and type 2. Type 1 diabetes is an autoimmune disease characterized by necrosis of pancreatic islet cells and a complete lack of insulin secretion. Patients with type 1 diabetes are dependent on insulin. Complications are similar to those described below for type 2 diabetes. The only treatment is insulin injections.

Type 2 diabetes mellitus was once called adult-onset diabetes. Now, because the epidemic of obesity and inactivity in children, type 2 diabetes is occurring at younger and younger ages. Although type 2 diabetes typically affects individuals older than 40 years, it has been diagnosed in children as young as 2 years of age who have a family history of diabetes.

Type 2 diabetes is characterized by peripheral insulin resistance with an insulin-secretory defect that varies in severity. For type 2 diabetes to develop, both defects must exist: All overweight individuals have insulin resistance, but only those with an inability to increase beta-cell production of insulin develop diabetes. In the progression from normal glucose tolerance to abnormal glucose tolerance, postprandial glucose levels first increase. Eventually, in hepatic gluconeogenesis increases, resulting in fasting hyperglycemia.

About 90% of patients who develop type 2 diabetes are obese. Because patients with type 2 diabetes retain the ability to secrete some endogenous insulin, those who are taking insulin do not develop DKA if they stop taking it for some reason. Therefore, they are considered to require insulin but not to depend on insulin. Moreover, patients with type 2 diabetes often do not need treatment with oral antidiabetic medication or insulin if they lose weight.

Maturity-onset diabetes of the young (MODY) is a form of type 2 diabetes that affects many generations in the same family with an onset in individuals younger than 25 years. Several types exist. Some of the genes responsible can be detected by using commercially available assays.

Gestational diabetes mellitus (GDM) is defined as any degree of glucose intolerance with onset or first recognition during pregnancy. GDM is a complication in approximately 4% of all pregnancies in the United States, though the rates may be 1-14% depending on the population studied. Untreated GDM can lead to fetal macrosomia, hypoglycemia, hypocalcemia, and hyperbilirubinemia. In addition, mothers with GDM have increased rates of cesarean delivery and chronic hypertension. To screen for GDM, a 50-g glucose screening test should be done at 24-28 weeks of gestation. This is followed by a 100-g, 3-hour oral glucose tolerance test if the patient's plasma glucose concentration at 1 hour after screening is greater than >140 mg/dL.

Approximately 13 million people in the United States have a diagnosis of diabetes, and diabetes is undiagnosed in another 5 million. Approximately 10% have type 1 diabetes, and the rest have type 2.

The morbidity and mortality associated with diabetes are related to the short- and long-term complications. Complications include hypoglycemia and hyperglycemia, increased risk of infections, microvascular complications (eg, retinopathy, nephropathy), neuropathic complications, and macrovascular disease.

Diabetes is the major cause of blindness in adults aged 20-74 years, as well as the leading cause of nontraumatic lower-extremity amputation and end-stage renal disease (ESRD).

Type 2 diabetes mellitus is more prevalent among Hispanics, Native Americans, African Americans, and Asians/Pacific Islanders than in non-Hispanic whites. The incidence is essentially equal in women and men in all populations. Type 2 diabetes is becoming increasingly common because people are living longer, and the prevalence of diabetes increases with age. It is also seen more frequently now than before in young people, in association with the rising prevalence of childhood obesity. Although type 2 diabetes still occurs most commonly in adults aged 40 years or older, though the incidence of disease is increasing more rapidly in adolescents and young adults than in other age groups.

Neurogenin 3 (Neurog3) is a key transcription factor in the differentiation of the endocrine pancreas. Neurog3 is an important part of the activation pathway for insulin gene expression and helps to ameliorate glucose tolerance (See, e.g., Watada, Endocrine Journal, 51, 255 (2004)). It is thought that lower than normal levels (e.g., under-expression) of Neurog 3 plays a role in certain types of Diabetes (See, e.g., Lee et al., Genes Dev. 16: 1488 (2002)).

Fingerstick glucose test is appropriate in the diagnosis for virtually all patients with diabetes. In patients who present with symptoms of uncontrolled diabetes (eg, polyuria, polydipsia, nocturia, fatigue, weight loss) with a confirmatory random plasma glucose level of >200 mg/dL, diabetes can be diagnosed.

In asymptomatic patients whose random serum glucose level suggests diabetes, a fasting plasma glucose (FPG) concentration should be measured. The oral glucose tolerance test no longer is recommended for the routine diagnosis of diabetes. An FPG level of >126 mg/dL on 2 separate occasions is diagnostic for diabetes. An FPG level of 110-125 mg/dL is considered impaired IFG. An FPG level of <110 mg/dL is considered normal glucose tolerance, though blood glucose levels above >90 mg/dL may be associated with an increased risk for the metabolic syndrome if other features are present.

Islet-cell autoantibodies are present in early type 1 but not type 2 diabetes. Measurements of these autoantibodies within 6 months of diagnosis can help differentiate type 1 and type 2 diabetes.

Most diabetic patients have type 2 diabetes, and most of those are asymptomatic at diagnosis. Initial treatment for these patients is a trial of medical nutrition therapy (MNT, diet therapy). Therefore, if an asymptomatic patient is incidentally found to have an elevated blood glucose level in the ED, the patient's primary physician can perform follow-up. Patients with mild symptoms of poorly controlled and previously undiagnosed diabetes can usually be treated as an outpatient, often with the initiation of a low dose of a sulfonylurea agent or metformin.

The treatment of markedly symptomatic patients with newly discovered type 2 diabetes and glucose levels >400 mg/dL is controversial. If close follow-up can be arranged, maximal doses of a sulfonylurea agent can be started, and they can be treated as outpatients. Patients generally feel better in 1-2 days, and in a week, their blood glucose levels are markedly lower. Their sulfonylurea dose can be tapered as they comply with MNT; in some, diabetes can be controlled with diet alone. Patients who cannot drink adequate amounts of fluid, those with serious coexisting medical conditions (eg, myocardial infarction (MI), systemic infection), and those without reliable follow-up should generally be hospitalized to start therapy.

The goal of oral antidiabetic therapy is to lower blood glucose levels to near-normal (preprandial levels of 90-130 mg/dL or 80-140 mg/dL and HbA1C levels <7%) and to maintain them in this range for the patient's lifetime. Patients with no or mild symptoms should initially be treated with MNT (diet therapy), and MNT should be encouraged throughout treatment. Drugs are started when a patient presents with moderate-to-marked symptoms of diabetes.

Treatment of type 2 diabetes is aimed at lowering insulin resistance and increasing function of beta cells. In many patients, beta-cell dysfunction worsens over time, necessitating exogenous insulin. Because patients with type 2 diabetes have both insulin resistance and beta-cell dysfunction, oral medication to increase insulin sensitivity (eg, metformin, a thiazolidinedione (TZD)) is often given with an intermediate-acting insulin (eg, neutral protamine Hagedorn (NPH)) at bedtime or a long-acting insulin (eg, glargine (Lantus) insulin, insulin detemir (Levemir)) given in the morning or evening. An insulin secretagogue, such as a sulfonylurea agent, can also be given to increase preprandial insulin secretion.

Drugs include Incretin mimetics (e.g., Exenatide (Byetta)) which mimic glucose-dependent insulin secretion, suppresses elevated glucagon secretion, and delays gastric emptying, Sulfonylurea agents (e.g., chlorpropamide, tolbutamide, tolazamide, acetohexamide, glyburide, glipizide, and glimepiride) that reduce glucose by increasing insulin secretion from pancreatic beta cells in patients with residual beta cell function, Meglitinides (e.g., Repaglinide (Prandin)) that are short-acting insulin secretagogues, Biguanides (e.g., Metformin (Glucophage)) that increase sensitivity of insulin by decreasing hepatic gluconeogenesis (primary effect) and increasing peripheral insulin sensitivity (secondary effect), Alpha-glucosidase inhibitors (AGIs) (e.g., Acarbose (Precose), Miglitol (Glyset)) that inhibit action of alpha-glucosidase (carbohydrate digestion), delaying and attenuating postprandial blood glucose peaks, thiazolidinediones (e.g., Pioglitazone (Actos), Rosiglitazone (Avandia)) that increase peripheral insulin sensitivity by increasing transcription of nuclear proteins that help increase uptake of glucose, probably with effects on free fatty acid levels, Amylin analogs (e.g., Pramlintide acetate (Symlin)) that have endogenous amylin effects by delaying gastric emptying, decreasing postprandial glucagon release, and modulate appetite. In some embodiments, SEL-PLEX is used in combination with the above described agents.

Using compositions and methods of the present invention, it was determined that Neurog3 expression was significantly upregulated 1.7-fold in subjects administered a composition comprising SEL-PLEX, whereas subjects that were administered SeM or Sod-sel treatments displayed no significant alteration of Neurog3 expression (See Example 6).

Thus, in some preferred embodiments, the present invention provides a method of treating a subject (e.g., a subject with diabetes) comprising administering to the subject a composition comprising SEL-PLEX under conditions such that the expression of Neurog3 is altered (e.g., enhanced) in the subject. Although an understanding of the mechanism is not necessary to practice the present invention and the present invention is not limited to any particular mechanism of action, administering to a subject with diabetes a composition comprising SEL-PLEX ameliorates glucose tolerance in the subject via up-regulating the expression of Neurog3 expression. In some embodiments, the present invention provides a method of treating a subject with diabetes comprising administrating to the subject a composition comprising SEL-PLEX with one or more other agents (e.g., vanadium, or those described above). In some embodiments, the present invention provides a method of enhancing the expression of Neurog3 in a subject comprising providing to the subject a composition comprising selenium under conditions such that the expression of Neurog3 is enhanced. In preferred embodiments, the composition comprising selenium comprises SEL-PLEX. The composition comprising SEL-PLEX may also comprise other forms of selenium, for example, Sod-sel.

V. Compositions and Formulations Comprising Selenium

Nutritional selenium levels have been established by the FDA (See 21 C.F.R. 101.9(c)(8)(iv), January 1994). Humans and animals can safely metabolize limited amounts of both inorganic and organic forms of selenium and can convert non-methylated selenium to mono-ordi-or trimethylated derivatives, of which the monomethylated derivatives are most toxic. (See, e.g., Bedwal, R. S., et al., Medical Hypotheses, 41 (2):150-159 (August 1993)). The FDA has adopted Reference Daily Intakes (RDIs) of 70 micrograms for selenium. Selenium dosage of 600 micrograms per day has been reported as safe. (See, e.g., Ferris G. M. Lloyd, et al., App. Clin. Biochem., 26:83-88 (1989)). At about this dosage, normal activity of the enzyme glutathione reductase safely converts selenogluthatione to hydrogen selenide in the liver and erythrocytes and is ultimately excreted. Thus, at such lower dosages, the body is able to safely metabolize and excrete selenium that is present in a free metallic form. However, as with many trace elements (e.g., selenium), at higher dosage levels or concentrations the beneficial effects are reversed and dangerous toxicity is manifested. (See, e.g., Furnsinn, C. et al., Internat'l J. of Obesity and Related Metab. Dis., 19(7): 458-463 (1995)).

Therefore, the administration of selenium in the natural form involves a scientific and medical trade-off because, when administered in relatively low concentrations, selenium provides beneficial health effects, however, at higher concentrations, selenium exhibits dramatic toxicity such that the potential health benefits are lost and toxicity becomes the primary concern.

As described above, the present invention demonstrates for the first time that certain forms of selenium (e.g., SEL-PLEX) are capable of providing beneficial effects to a subject that other forms of selenium (e.g., selenomethionine) do not. The present invention contemplates the use of multiple forms of selenium. The source of selenium may be a synthetic or natural source, and the selenium may be organic or inorganic. Evidence has shown that organic forms of selenium (e.g., selenomethionine and selenium enriched yeast) may be less toxic and better absorbed than inorganic forms (See, e.g., Mahan, Proceedings of the 15th Annual Symposium Nottingham University Press, Nottingham, UK, pp. 523-535 (1999)). As described herein, and depending on the target sought to be treated in a subject (e.g., gene expression involved in a neurodegenerative or other disease), multiple forms of selenium may be used independently or in combination with one another. Natural sources of selenium include, but are not limited to, selenium enriched (e.g., selenized) yeast. The yeast strain used is not limiting.

In certain preferred embodiments of the present invention, SEL-PLEX (Alltech, Lexington, Ky.) is the selenium form of choice for formulations and compositions. In some embodiments, compositions comprising SEL-PLEX provide a more biologically available form of selenium compared to other forms of selenium (See Example 9). However, other forms of selenium may also find use in the present invention including derivative or modifications of SEL-PLEX or other forms of selenium enriched yeast, selenomethionine, selenocysteine, a selenite compound, a selenate compound, or derivatives, salts, or modifications thereof. Thus, in some preferred embodiments, each of these forms of selenium may be used as a component of a formulation. Alternatively, each of the above described forms of selenium may be linked (e.g., chemically or physically) to a drug or therapeutic (e.g., an Alzheimer's therapeutic) to form a selenium-drug derivative. Additionally, compositions and formulations are not limited to one form or selenium. Indeed, a composition or formulation may comprise multiple forms of selenium (e.g., SEL-PLEX and Sod-sel).

Other forms of selenium that find use in various embodiments of the present invention are described in U.S. Pat. Nos. 6,911,550 6,197,295, 5,221,545, 6 and 6,576,233, and U.S. Pat. App. Nos. 20010043925, 20050069594, and 20050089530, herein incorporated by reference in their entireties.

Accordingly, the present invention provides pharmaceutical compositions which may comprise one or more forms of selenium, alone or in combination with at least one other agent, such as a stabilizing compound, or Alzheimer's therapeutic, and may be administered in any sterile, biocompatible pharmaceutical carrier, including, but not limited to, saline, buffered saline, dextrose, and water.

The methods of the present invention find use in treating (e.g., prophylacticly or therapeutically) diseases or altering physiological states. Selenium (e.g., SEL-PLEX) can be administered to a subject (e.g., a patient) intravenously in a pharmaceutically acceptable carrier such as physiological saline. Standard methods for intracellular delivery of compounds can be used (e.g., delivery via liposome). Such methods are well known to those of ordinary skill in the art. The formulations of this invention are useful for parenteral administration, such as intravenous, subcutaneous, intramuscular, and intraperitoneal.

As is well known in the medical arts, dosages for any one subject may depend upon many factors, including the patient's size, body surface area, age, the particular compound to be administered, sex, time and route of administration, general health, and interaction with other drugs being concurrently administered.

Accordingly, in some embodiments of the present invention, compositions and/or formulations comprising selenium can be administered to a subject alone, or in combination with other forms of selenium, drugs, small molecules, or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, compositions comprising selenium may be administered alone to individuals subject to or suffering from a disease or condition (e.g., Alzheimer's disease, Parkinson's disease, diabetes, etc.). Compositions comprising selenium (e.g., SEL-PLEX alone or in combination with one or more other forms of selenium) may be added to a nutritional drink or food (e.g., ENSURE, POWERBAR, or the like), a multi-vitamin, nutritional products, food products, etc. for daily consumption.

Depending on the target sought to be altered by treatment (e.g., gene expression associated with aging), these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of the pharmaceutical agent may be that amount that alters the expression of a specific gene (e.g., Lhx8, presenilin 1, presenilin 2, or Apbb1). Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For compositions or formulations comprising selenium, conditions indicated on the label may include treatment of condition related to prophylactic or therapeutic treatment of neurodegenerative disease or cognitive function.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the methods of the invention, the therapeutically effective dose can be estimated initially from cell culture assays. Then, preferably, dosage can be formulated in animal models (particularly murine models) to achieve a desirable circulating concentration range.

A therapeutically effective dose refers to that amount of which ameliorates or prevents symptoms of a disease state or condition (e.g., through altering gene expression) Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds which exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage may be chosen by a subject or by a physician in view of the patient to be treated. Dosage and administration are adjusted to provide sufficient levels of the active moiety or to maintain the desired effect (e.g., alteration of gene expression in a subject). Additional factors that may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

In some embodiments, selenium (e.g., organic selenium (e.g., selenized yeast (e.g., SEL-PLEX))) is administered at a daily dose of between 25 and 800 µg per day (e.g., SEL-PLEX is administered to a subject in such a way so as to provide between 25 and 800, µg of selenium to the subject each day). In preferred embodiments, the selenium (e.g., organic selenium (e.g., selenized yeast (e.g., SEL-PLEX))) is administered at a daily dose of between 200 and 500 µg per day. In other preferred embodiments, selenium is administered at a daily dose of between 200 and 400 µg per day. Doses outside of 25 and 800 µg may be used. In some embodiments, a single dose of selenium (e.g., organic selenium (e.g., selenized yeast (e.g., SEL-PLEX))) is administered once daily. In other embodiments, 2, 3, 4, or more doses may be administered each day (e.g., once in the morning and once at night, or once every 4 to 6 hours). For example, in some embodiments, selenium is adminitstered to a subject in three separate, more than three separate, two separate, or less than two separate doses. In some preferred embodiments, the daily dose is administered in a time release capsule. In some preferred embodiments, the daily dose is between 25-75 µg of selenium. In other preferred embodiments, the daily dose is 200 µg of selenium (e.g., organic selenium (e.g., selenized yeast (e.g., SEL-PLEX))).

The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Compositions and formulations comprising selenium are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Thus, in some embodiments, pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

Thus, in some embodiments, the compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

In some embodiments, the invention provide pharmaceutical compositions containing (a) one or more forms of selenium (e.g., SEL-PLEX and/or Sod-sel) and (b) one or more other agents (e.g., Alzheimer's therapeutic). Examples of such Alzheimer's therapeutic agents are described above. In some embodiments, two or more combined agents (e.g., Alzheimer's therapeutics) may be used together or sequentially.

The present invention also includes methods involving co-administration of compounds comprising selenium described herein with one or more additional active agents (e.g., an Alzheimer's therapeutic, anti-oxidant, etc.). Indeed, it is a further aspect of this invention to provide methods for enhancing prior art therapies and/or pharmaceutical compositions by co-administering a composition comprising selenium of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered agents may each be administered using different modes or different formulations.

The agent or agents to be co-administered depends on the type of condition being treated. For example, when the condition being treated is a neurodegenerative disease, the additional agent can be an Alzheimer's therapeutic, an ALS therapeutic, a Huntington's therapeutic, or the like. When the condition being treated is diabetes, the additional agent can be a diabetes therapeutic. When the condition being treated is cognitive function, the additional agent can be an antioxidant. The additional agents to be co-administered, such as Alzheimer's therapeutics, diabetes therapeutics, or antioxidants, can be any of the well-known agents in the art, including, but not limited to, those that are currently in clinical use.

Treatment of the various diseases and disorders described herein are often generally limited by the following two major factors: (1) the development of drug resistance and (2) the toxicity of known therapeutic agents. Some therapeutic agents have deleterious side effects, including non-specific lymphotoxicity and renal toxicity.

The methods described herein address both these problems. Drug resistance, where increasing dosages are required to achieve therapeutic benefit, is overcome by co-administering the compounds comprising selenium described herein with the known agent. In some embodiments, the compounds described herein sensitize target cells to known agents (and vice versa) and, accordingly, less of these agents are needed to achieve a therapeutic benefit.

The sensitizing function of the claimed compounds also addresses the problems associated with toxic effects of known therapeutics. In instances where the known agent is toxic, it is desirable to limit the dosages administered in all cases, and particularly in those cases were drug resistance has increased the requisite dosage. Thus, in some embodiments, when the claimed compounds are co-administered with the known agent, they reduce the dosage required which, in turn, reduces the deleterious effects. Further, because the claimed compounds are themselves both effective and non-toxic in moderate doses, co-administration of proportionally more of these compounds than known toxic therapeutics will achieve the desired effects while minimizing toxic effects.

VI. Antioxidants

In some embodiments of the present invention, antioxidants are co-administered with compositions or formulations of the present invention. The present invention is not limited by the type of antioxidant utilized. Indeed, a variety of antioxidants are contemplated to be useful in the present invention including, but not limited to, alkylated diphenylamines, N-alkylated phenylenediamines, phenyl-α-naphthylamine, alkylated phenyl-α-naphthylamine, dimethyl quinolines, trimethyldihydroquinolines and oligomeric compositions derived therefrom, hindered phenolics, alkylated hydroquinones, hydroxylated thiodiphenyl ethers, alkylidenebisphenols, thiopropionates, metallic dithiocarbamates, 1,3,4-dimercaptothiadiazole and derivatives, oil soluble copper compounds, and the like, Naugalube® 438, Naugalube 438L, Naugalube 640, Naugalube 635, Naugalube 680, Naugalube AMS, Naugalube APAN, Naugard PANA, Naugalube TMQ, Naugalube 531, Naugalube 431, Naugard BHT, Naugalube 403, and Naugalube 420, ascorbic acid, tocopherols including alpha-tocopherol, water-soluble antioxidants such as sulfhydryl compounds and their derivatives (e.g., sodium metabisulfite and N-acetyl-cysteine), lipoic acid and dihydrolipoic acid, resveratrol, lactoferrin, ascorbic acid derivatives (e.g., ascorbyl palmitate and ascorbyl polypeptide), butylated hydroxytoluene, retinoids (e.g., retinol and retinyl palmitate), tocotrienols, ubiquinone, extracts containing flavonoids and isoflavonoids and their derivatives (e.g., genistein and diadzein), extracts containing resveratrol and the like, grape seed, green tea, pine bark, propolis, Irganox1010, 1035, 1076, 1222 (manufactured by Ciba Specialty Chemicals Co., Ltd.), Antigene P, 3C, FR, Sumilizer GA-80 (manufactured by Sumitomo Chemical Industries Co., Ltd.), beta-carotene, lycopene, vitamins C, E, and A, and other substances.

For example, in some embodiments, the present invention provides a method of protecting against the by-products of oxidative stress in brain tissue comprising administering to a subject a composition comprising SEL-PLEX. Although an understanding of the mechanism is not necessary to practice the present invention and the present invention is not limited to any particular mechanism of action, in some embodiments, administering a composition comprising SEL-PLEX to a subject reduces the expression of GST genes (e.g., Gstp1, Gstz1, and Gstm7) in the subject. In some embodiments, administering a composition comprising SEL-PLEX to a subject reduces the level of DNA damage in brain tissue (e.g., neocortex) of a subject. Although an understanding of the mechanism is not necessary to practice the present invention and the present invention is not limited to any particular mechanism of action, in some embodiments, treatment with compositions and methods of the present invention (e.g., dietary supplementation with SEL-PLEX) stabilizes cellular homeostasis (e.g., in the brain) such that the expression of DNA-damage inducible genes (e.g., Gadd45b) is reduced.

In some embodiments, the present invention provides a method of reducing sensitivity of cells to $H_2O_2$ cytotoxicity comprising administering to the cells a composition comprising Sod-sel and/or SEL-PLEX under conditions such that the expression of SelW is altered (e.g., increased) (See, e.g., Example 3). In some embodiments, the present invention provides a method of reducing the expression of SelW in a subject comprising administering a composition comprising selenium (e.g., SEL-PLEX and/or Sod-sel) and an antioxidant under conditions such that the expression of SelW is altered. In some embodiments, the present invention provides a method of promoting repair of oxidatively damaged proteins in a subject comprising administering to the subject a composition comprising Sod-sel and/or SEL-PLEX under conditions such that the expression of SelR is altered (e.g., increased) (See, e.g., Example 3).

The present invention further provides a method of reducing superoxide radicals in a subject (e.g., in a subject experiencing oxidative stress) comprising administering a composition (e.g., a nutritional supplement) comprising selenium (e.g., SEL-PLEX) to the subject. Furthermore, in some embodiments, the present invention provides that subjects receiving certain compositions comprising selenium (e.g., selenium supplements comprising SEL-PLEX) have an enhanced ability to deal with oxidative stress. Although an understanding of the mechanism is not necessary to practice the present invention and the present invention is not limited to any particular mechanism of action, in some embodiments, subjects receiving a composition comprising selenium (e.g., a dietary supplement comprising SEL-PLEX) have an enhanced ability to cope with oxidative stress due to the ability of select forms of selenium (e.g., SEL-PLEX) to alter (e.g., reduce) the level of superoxide radicals in the subject. In some embodiments, reduction of superoxide radicals occurs in the brains (e.g., cerebral cortex) of subjects treated with the compositions and methods of the present invention (See e.g., Example 10, below).

It is contemplated that the compositions and methods of the present invention will find use in various settings, including research and clinical diagnostics. For example, compositions and methods of the present invention also find use in studies of APP metabolism (e.g., via analysis of proteins and pharmaceuticals capable of altering levels thereof) and in in vivo studies to observe Alzheimer's disease pathology. In addition, methods to quantitate oligomeric and/or fibrillar β-amyloid protein assemblies in samples find use in monitoring and/or determining the effectiveness of Alzheimer's disease treatment, as it is contemplated that decreasing levels of oligomeric β-amyloid protein assemblies in a subject's samples over time indicates the effectiveness of an Alzheimer's disease treatment.

Also provided herein is a method of identifying new treatments for neurodegenerative disease (e.g., Alzheimer's disease) comprising treating a subject having neurodegenerative disease (e.g., Alzheimer's disease) with a composition comprising selenium (e.g., organic selenium (e.g., selenized yeast (e.g., SEL-PLEX))) under conditions such that the expression level of a gene associated with neurodegenerative disease (e.g., Alzheimer's disease) is altered (e.g., presenilin 1, presenilin 2), and then co-administering one or more test compounds, wherein the one or more test compounds are examined for the ability to alter the expression of a gene associated with neurodegenerative disease (e.g., Alzheimer's disease) (e.g., presenilin 1, presenilin 2). Changes in the expression levels of a gene associated with neurodegenerative disease (e.g., Alzheimer's disease) is indicative of a compound that could be used for treating neurodegenerative disease (e.g., Alzheimer's disease). These methods can be used to screen compounds for other diseases and conditions (e.g., those described herein).

Uses of the compositions and methods provided by the present invention encompass human and non-human subjects and samples from those subjects, and also encompass research as well as diagnostic applications. Thus, it is not intended that the present invention be limited to any particular subject and/or application setting.

EXPERIMENTAL

The following examples are provided in order to demonstrate and further illustrate certain preferred embodiments and aspects of the present invention and are not to be construed as limiting the scope thereof.

Example 1

Materials and Methods

Animal Care. Male C57BL/6J mice were housed singly and started on the experimental diets described below immediately after weaning (21 days of age). The mice were maintained in the Shared Aging Rodent Facility at the William S. Middleton Memorial Veterans Administration Medical Center (Madison, Wis.). Temperature and humidity were maintained at constant levels. Room light was controlled to provide 12-hr cycles of light and dark.

Experimental diets were created by Harlan Teklad (Madison, Wis.). Selenium content of the diets was determined by Covance Inc. (Madison, Wis.). Five (5) animals were included in each of the following treatment groups: a diet deficient in selenium (SD); a diet supplemented with selenomethionine (SM, obtained from Sigma, St. Louis, Mo.) such that the final selenium content of the diet was one (1) part per million; a diet supplemented with sodium selenite (SS, Sigma) such that the final concentration of selenium in this diet was one (1) part per million; or a diet supplemented with the yeast selenium SEL-PLEX (SP, Alltech, Lexington, Ky.), such that the final concentration of selenium in this diet was one (1) part per million. SEL-PLEX. Mice were provided with water and their respective diet ad libitum for 100 days. Diets were stored at the dark at 4° C. and fresh diet was added to feeder twice weekly.

Tissue sample preparation and microarray analysis. Mice were killed at 100 days of age by cervical dislocation. For intestinal expression studies, the intestine was flushed twice with saline solution and small intestine was measured and divided in three equal segments. A 3-cm region of the middle segment of the small intestine corresponding to the jejunum (~300 mg of tissue) was cut and rinsed again with physiological saline to completely remove contents, flash frozen in liquid nitrogen and stored at −80° C. For brain (e.g., cerebral cortex) studies, the cerebral cortex was separated from the surrounding brain tissue and was flash frozen in liquid nitrogen and stored at −80° C.

Total RNA was isolated from using the guanidinium isothiocyanate method of TRIZOL (Life Technologies, Grand Island, N.Y.) and individual samples were used for gene expression profiles. Total RNA was cleaned up by RNeasy Mini kit (Qiagen, Valencia, Calif.). Target RNA was prepared by converting 5 mg total RNA into double-strand cDNA using GeneChip Expression 3'-Amplification Reagents One-Cycle cDNA Synthesis Kit (Affymetrix, Santa Clara, Calif.) with a $T7-(dT)_{24}$ primer incorporating a T7 RNA polymerase promoter. After cleaning up double-strand cDNA using Genechip Sample Cleanup Module (Affymetrix, Santa Clara, Calif.), biotin-labeled cRNA was synthesized from double-strand cDNA using GeneChip Expression 3'-Amplification Reagents for IVT Labeling (Affymetrix, Santa Clara, Calif.). The biotin-labeled cRNA was cleaned up using Genechip Sample Cleanup Module and was fragmented by heating (35 min at 94° C.).

Fifteen (15) µg of cRNA fragments were hybridized (16 h at 45° C.) to Mouse Genome 430 2.0 Array (Affymetrix, Santa Clara, Calif.) using GeneChip Hybridization Oven 640. After hybridization, the gene chips were automatically washed and stained with streptavidin-phycoerythrin biotinylated anti-streptavidin using Affymetrix GeneChip Fluidics Station 450. The DNA chips were scanned with Affymetrix GeneChip Scanner 3000 (Affymetrix, Santa Clara, Calif.) to detect the cell signal intensities by laser. All calculations were performed with Affymetrix GeneChip Operating Software (GCOS) version 1.3 after scanning.

Data Analysis.
1. The spreadsheet containing probe set identifiers and signal intensity values was opened in Microsoft Excel (version 11.1.1 for the Macintosh OS-X operating system) and summary statistics were generated (mean signal intensity for each treatment group, standard error of the mean). Two-tailed t-tests (equal variance) were performed for the following treatment groups: SM vs. SD, SS vs. SD, and SP vs. SD. Additionally, a "signal intensity score" was calculated for each probe set as the sum of the signal intensities for all chips (N=20).
2. The most recent annotation file was downloaded from the Affymetrix website. The data in this file was used to annotate the gene expression data in Step 1. The resulting file was exported as a comma separated value (CSV) file.
3. The CSV file from Step 2 was imported into a database application (MySQL version 4.1.12 for the Macintosh OS-X operating system).
4. Using MySQL, probe set identifiers ending with the letters "_x_at" and "_s_at" were removed from the data set. According to Affymetrix, probe sets with these extensions do not map to unique genes (i.e., transcripts from more than one gene may hybridize to one probe set). After removing these probe sets, the data were exported as a CSV file.

5. The file from Step 3 was opened in Microsoft Excel to identify multiple occurrences of the same gene within the data set. When two (or more) probe sets were determined to represent the same gene, the probe set with the largest "signal intensity score" (see Step 2) was retained and the additional probe set(s) were deleted from the data set. At this stage, each probe set represent only a single transcript, and so hereafter the term "probe set" is interchangeable with the term "gene".

6. A new column in the data file was created to include information about how the expression of a particular gene was affected by the dietary treatment. Using the p-values from the t-tests described in Step 1, genes were sorted into one of the following categories (and this information was noted in the new column); note that "statistically significant", as referred to below, means that the p-vaule(s) of interest were ≤ (less than or equal to) 0.01:
   a. "SelMeth specific": there was a statistically significant change in expression of this gene only in the SM vs. SD comparison (i.e., expression of the gene was not statistically significantly different for either the SS vs. SD or the SP vs. SD comparisons.
   b. "SodSel" specific": there was a statistically significant change in expression of this gene only in the SS vs. SD comparison
   c. "SelPlex specific": there was a statistically significant change in expression of this gene only in the SP vs. SD comparison
   d. "SelMeth-SodSel": there was a statistically significant change in expression of this gene in only for the SM vs. SD and the SS vs. SD comparisons
   e. "SelMeth-SelPlex": there was a statistically significant change in expression of this gene in only for the SM vs. SD and the SP vs. SD comparisons
   f. "SodSel-SelPlex": there was a statistically significant change in expression of this gene in only for the SS vs. SD and the SP vs. SD comparisons
   g. "Unaffected": the expression of this gene was not significantly affected by the SM, SS or SP diets relative to the SD diets
   h. "Affected by all": the expression of this gene was significantly different for the SM, SS, and SP groups relative to the SD group 7. The dataset was divided into two sub-sets, one containing "well-characterized genes" (essentially those transcripts that have a unique gene title and gene symbol according to Affymetrix's probeset annotation information) and "Uncharacterized transcripts" (all remaining probesets in the data set, including expressed sequence tags, cDNA sequences, etc.).

8. Each gene in the "well-characterized genes" subset of data was then assigned a "gene function" using the "GO Biological Process" column of the annotation information provided by Affymetrix. in cases where multiple and diverse gene ontology (GO) information is provided, information from the National Center for Biotechnology Information (NCBI) databases (Entrez-Gene, PubMed, etc.) were used to generate a "consensus opinion" for the function of that gene.

Example 2

Dietary Selenium Alters Gene Expression in the Mouse Intestine

The ability of dietary selenium (e.g., derived from various sources such as SeM, Sel-sod, and SEL-PLEX) to alter the physiology (e.g., physiologic homeostasis) and the expression patterns (e.g., protein or gene expression patterns) of various functional groups of proteins and various protein pathways in mouse intestine and brain (e.g., cerebral cortex) was examined.

Thus, it was an object of the present invention to determine whether compositions and methods of the present invention could alter the expression levels (e.g., mRNA levels) of various genes. One group of genes analyzed were genes classically associated with selenium. As described above, the expression levels of genes were analyzed between mice with and without dietary selenium, or, between mice fed different sources of selenium) (See, e.g., Table 1, below). No significant differences were observed in body weights of mice receiving a diet deficient in selenium, a diet comprising selomethionine (Se-meth, or SeM), a diet comprising sodium selenite (Sod-sel, or SS), or a diet comprising SEL-PLEX (SEL-PLEX, or SP) (See FIG. 1).

Selenium is known for its role in antioxidant systems, mainly because selenium (as selenocysteine) is a key component of glutathione peroxidases (GSH-Px). Glutathione peroxidases are a class of enzymes that metabolize or detoxify hydrogen peroxide and lipid hydroperoxides. Thus, they function to protect the cell against damage caused by reactive oxygen species (ROS) produced as by-products of aerobic cellular metabolism (See, e.g., Arthur, Cell. Mol. Life Sci. 57, 1825, (2000)).

Accordingly, it was determined whether the expression level of GSH-Px would change in subjects that received selenium supplementation (e.g., dietary selenium supplementation) versus those that did not (e.g., selenium deficient subjects). Using the compositions and methods of the present invention, it was demonstrated that there was a significant fold change (FC) in GSH-Px gene expression in subjects receiving selenium supplementation (e.g., receiving Se-meth, Sod-sel, and SEL-PLEX) compared to selenium deficient subjects. The fold change in expression levels of two GSH-Px genes is described in Table 1, below:

TABLE 1

| Gene | Se-meth | Sod-sel | SEL-PLEX |
|---|---|---|---|
| Glutathione Peroxidase 1 (all p < 0.01) | 4.9 | 4.1 | 4.7 |
| Glutathione Peroxidase 3 (all p < 0.01) | 4.6 | 3.5 | 3.6 |

Expression of other genes associated with selenium were also examined and determined to be altered. For example, the upregulation of selenoenzymes (e.g., Thioredoxin Reductase 1 (Trx-1), See, e.g., Rundlof and Arner, Anitoxidants and Redox Signaling, 6, 41 (2004)) was observed. The thioredoxin system is a key defense against ROS and consists of Thioredoxin and Thioredoxin Reductase which reduces Thioredoxin using NADPH. In subjects receiving selenium supplementation, the fold increase in expression of the Thioredoxin Reductase 1 gene was as follows: SeM, 1.8; SS, 1.7; SP 1.8 (all with p values <0.01). Thus, compositions and methods of the present invention functioned to alter the expression of genes previously known to be associated with selenium.

Another selenoenzyme, Type 1 iodothyronine deiodinase (See, e.g., Larsen and Berry, Annu. Rev. Nutr., 15, 323 (1995)), also displayed increased expression using the compositions and methods of the present invention. This enzyme is responsible for the conversion of Thyroxin (T4) to bioactive thyroid hormone (T3). Selenium supplementation significantly increased the expression level (e.g., nucleic acid expression) of Type 1 iodothyronine deiodinase as follows: SeM, 2.0 fold increase; SS, 2.8 fold increase; SP, 2.1 fold increase.

Example 3

Dietary Selenium Alters the Expression Level of Selenoprotein-Encoding Genes in a Selenium Source-Dependent Manner Selenium (Se) is now known to be incorporated as selenocysteine in a number of selenoproteins, glutathione peroxidase (GSH-Px, See Example 2) being the prototypical example. Selenocysteine is specifically encoded by the UGA codon, and inserted in peptide chains by a cotranslational mechanism that is able to override the normal function of UGA as a termination codon. In eukaryotes, efficient selenocysteine incorporation at UGA codons requires a cellular protein factor and a cis-acting structural signal usually located in the mRNA 3'-untranslated region (3'-UTR), consisting of a selenocysteine insertion sequence (SECIS) in a characteristic stem-loop structure (See, e.g., Peterlin et al., (1993), In Human Retroviruses; Cullen, Ed.; Oxford University Press: New York; pp. 75-100; Le and Maizel, Theor. Biol. 138:495 (1989)). The required protein factor is presumed to be present in certain cells types that express selenoproteins, such as liver cells, lymphocytes, macrophages, thrombocytes, and other blood cells. In such cell types, the presence of a SECIS element in an mRNA is necessary and sufficient for in-frame UGA codons to be translated as selenocysteine.

The expression levels of several selenoprotein-encoding genes were affected by selenium supplementation. Importantly, the present invention demonstrates for the first time that there exists significant differences in the ability of various sources of selenium to alter the expression levels of the same genes (e.g., selenoprotein genes and other genes described herein). For example, the expression of Selenoprotein W (SelW), was not significantly altered by SeM. However, Sod-sel and SEL-PLEX upregulated SelW 5.1 fold. SelW is expressed in many tissues, including brain, where its expression level is maintained in selenium deficiency. SelW is a glutathione-dependent antioxidant and it has been shown that overexpression of SelW in CHO cells and H1299 human lung cancer cells markedly reduces the sensitivity of both cell lines to $H_2O_2$ cytotoxicity (See, e.g., Jeong et al., FEBS Letter, 517, 225 (2002)). Thus, in some embodiments, the present invention provides a method of reducing sensitivity of cells to $H_2O_2$ cytotoxicity comprising providing to the cells a composition comprising Sod-sel and/or SEL-PLEX under conditions such that the expression of SelW is altered (e.g., increased).

Further illustrating the selenium source dependent nature of the ability to alter gene expression, the expression level of the gene for selenoprotein N1 (Sepn1), was not significantly affected by SeM or Sod-sel, but was increased 1.8-fold by SEL-PLEX (p<0.02). It is thought that Sepn1 plays an important role in muscle integrity. For example, in humans, multi-minicore disease consists of a spectrum of congenital neuromuscular diseases with clinical conditions such as weakness and structural muscular changes. It is known that a third of all multiminicore disease cases are due to mutations in the Sepn1 gene (See, e.g., Neuromuscul. Disord. 15 (4), 299-302 (2005); Am. J. Hum. Genet. 71 (4), 739-749 (2002)). Thus, in some embodiments, the present invention provides a method of maintaining muscle integrity comprising providing to the cells a composition comprising SEL-PLEX under conditions such that the expression of Sepn1 is altered (e.g., increased).

Methionine sulfoxide reductases catalyze reduction of free and protein-bound methionine sulfoxides to corresponding methionines (See, e.g., Brot et al., Proc. Natl. Acad. Sci. USA 78, 2155 (1981); Weissbach et al., Arch. Biochem. Biophys. 397, 172 (2002)). The oxidation of methionine by reactive oxygen species (ROS) generates a diastereomeric mixture of methionine-S-sulfoxide (Met-S-SO) and methionine-R-sulfoxide (Met-R-SO). Two distinct enzyme families evolved for reduction of these sulfoxides, with methionine-S-sulfoxide reductase (MsrA) being stereospecific for Met-S-SO and methionine-R-sulfoxide reductase (MsrB) for Met-R-SO. Previously described functions of these enzymes include repair of oxidatively damaged proteins, regulation of protein function and elimination of oxidants through reversible formation of methionine sulfoxides (See, e.g., Levine et al., IUBMB Life 50, 301 (2000)).

To date, two mammalian MsrB proteins have been identified: selenocysteine (Sec)-containing protein, designated selenoprotein R (SelR; See, e.g., Kryukov et al., J. Biol. Chem. 274, 33888 (1999); Proc. Natl. Acad. Sci. USA 99, 4245 (2002)) and its homolog, designated CBS-1, in which Cys is present in place of Sec (See, e.g., Jung et al., FEBS Lett. 527, 91 (2002)). The Sec-containing MsrB has only been described in mammals. Members of the MsrB family have been characterized mechanistically (See, e.g., Kumar et al., J. Biol. Chem. 277, 37527 (2002); Olry et al., J. Biol. Chem. 277, 12016 (2002)); and structurally (Lowther et al., Nat. Struct. Biol. 9, 348 (2002)).

The gene for SelR (also known as Selenoprotein X1) was not significantly affected by SeMet dietary supplementation but was upregulated 1.3-fold (p<0.01) and 1.2-fold (p<0.05) by Sod-sel and SEL-PLEX, respectively. As described above, SelR is a methionine sulfoxide reductase. Methionine residues in proteins are susceptible to damage by ROS but can be repaired via reduction of the resulting methionine sulfoxides by enzymes such as SelR (See, e.g., Kim and Gladyshev, Mol Biol Cel 15, 1055, (2004)). Accordingly, in some embodiments, the present invention provides a method of promoting repair of oxidatively damaged proteins in a subject comprising providing to the subject a composition comprising Sod-sel and/or SEL-PLEX under conditions such that the expression of SelR is altered (e.g., increased).

Example 4

Selective Forms of Dietary Selenium Alter the Expression of Stress-Inducible Proteins The superoxide dismutase genes (e.g., SOD1 and SOD2) encode an intramitochondrial free radical scavenging enzymes that are a first line of defense against superoxide (e.g., superoxide radicals) produced as a byproduct of oxidative phosphorylation. (See, e.g., Li et al. Nature Genet. 11: 376 (1995)). Inactivation (e.g., homozygous mutants) of the Sod2 gene in transgenic mice by homologous recombination results in mice dying within the first 10 days of life with a dilated cardiomyopathy, accumulation of lipid in liver and skeletal muscle, and metabolic acidosis (See, e.g., Li et al. Nature Genet. 11: 376 (1995)). Cytochemical analysis revealed a severe reduction in succinate dehydrogenase (complex II) and aconitase (a tricarboxylic acid cycle enzyme) activities in the heart and to a lesser extent in other organs. The findings suggested that MnSOD is required for normal biologic function of tissues by maintaining the integrity of mitochondrial enzymes susceptible to direct inactivation by superoxide.

Reactive oxygen species (ROS) have been implicated in a wide range of degenerative processes including amyotrophic lateral sclerosis, ischemic heart disease, Alzheimer disease, Parkinson disease, and aging. ROS are generated by mitochondria as the toxic by-products of oxidative phosphorylation, their energy generating pathway. As noted above, genetic inactivation of the mitochondrial form of SOD in mice results in dilated cardiomyopathy, hepatic lipid accumulation, and early neonatal death (See, e.g., Li et al. Nature Genet. 11: 376 (1995)). It has been reported that treatment with a SOD mimetic, MnTBAP, rescued Sod2−/− mutant mice from this systemic pathology and dramatically prolonged their survival (See, e.g., Melov et al., Nature Genet. 18: 159 (1998)). Surviving animals developed a pronounced movement disorder progressing to total debilitation by 3 weeks of age. Neuropathologic evaluation showed a striking spongiform degeneration of the cortex and specific brainstem nuclei, associated with gliosis and intramyelinic vacuolization similar to that observed in cytotoxic edema and disorders associated with mitochondrial abnormalities such as Leigh disease and Canavan disease. It has been suggested that because of the failure of MnTBAP to cross the blood-brain barrier progressive neuropathology is caused by excessive mitochondrial production of ROS (See, e.g., Melov et al., Nature Genet. 18: 159 (1998)).

Knockout mice for SOD1 exhibit typical progressive muscle atrophy and weakness with selective damage to motor neurons that closely resembles human ALS. There appears to be a causal relationship between mutant SOD1 secretion and neural toxicity (e.g., the mutant protein is not secreted). However, infusion of wild-type SOD in an ALS rat model significantly delays disease onset (See, e.g., J. Neurosci, 25, 108-117 (2005)). Additionally, it has been shown that a copper (Cu) chaperone is required for efficient loading of Cu into SOD (See, e.g., Nat. Neurosci, 5, 301-307 (2002)). Thus, the ability to maintain normal levels of wild-type SOD or to enhance expression or function of the same may provide a beneficial therapeutic effect for ALS subjects.

Furthermore, it has been shown that regressive numbers of basal forebrain cholinergic neurons appear in several areas of the brain of ALS subjects (See, e.g., Neurochem Int. 46, 357-368, (2005)). Thus, the ability to upregulate genes involved in basal forebrain cholinergic neuron growth and/or maintenance may provide beneficial effects for a subject with ALS.

Thus, it was determined whether dietary selenium supplements could alter the expression levels of SOD genes (e.g., SOD1 and SOD2). Subjects administered a compositions comprising selenium (e.g., SEL-PLEX or Sod-sel) exhibited and enhanced expression of SOD1 (e.g., 1.2 and 1.92 fold, respectively. Additionally, these subjects also exhibited an enhancement in the expression of the Cu chaperone for SOD, (CCS) (1.19 fold and 1.28 fold, respectively). Thus, the present invention provides a method of treating a subject with ALS comprising administering a composition comprising selenium under conditions such that the expression of SOD1 and/or CCS is enhanced.

In some embodiments, the present invention provides a method of reducing superoxide radicals in a subject (e.g., in a subject experiencing oxidative stress) comprising providing a composition (e.g., a nutritional supplement) comprising selenium (e.g., SEL-PLEX) to the subject. Furthermore, in some embodiments, the present invention provides that subjects receiving certain compositions comprising selenium (e.g., selenium supplements comprising SEL-PLEX) have an enhanced ability to deal with oxidative stress. Although an understanding of the mechanism is not necessary to practice the present invention and the present invention is not limited to any particular mechanism of action, in some embodiments, subjects receiving a composition comprising selenium (e.g., a dietary supplement comprising SEL-PLEX) have an enhanced ability to cope with oxidative stress due to the ability of select forms of selenium (e.g., SEL-PLEX) to alter (e.g., reduce) the level of superoxide radicals in the subject. In some embodiments, reduction of superoxide radicals occurs in the brains (e.g., cerebral cortex) of subjects treated with the compositions and methods of the present invention (See e.g., Example 10, below).

Another unique effect of SEL-PLEX was its ability to significantly down-regulate the expression of the stress-inducible selenoprotein, type II iodothyronine deiodinase, (Dio2).

Thyroid hormone has important regulatory effects in some mammalian tissues, such as the developing brain, the anterior pituitary gland, and brown adipose tissue (See, e.g., Croteau et al. J. Clin. Invest. 98: 405-417, (1996)). A relatively high proportion of the receptor-bound triiodothyronine is found within the tissue itself rather than in plasma. The expression in these tissues of type II iodothyronine deiodinase (Dio2), which catalyzes deiodination of thyroxine T4 exclusively on the outer ring (5-prime-position) to yield T3, suggests that Dio2 is responsible for this 'local' production of T3 and is thus important in influencing thyroid hormone action in these tissues. In addition, Dio2 activity is markedly elevated in the hypothyroid state and appears to be responsible for catalyzing the production of a large proportion of the circulating T3 under such conditions. It has been noted that, from the cDNAs of iodothyronine deiodinase types I and III, deiodinases contain in-frame TGATGA codons that code for selenocysteine (See, e.g., Croteau et al. J. Clin. Invest. 98: 405-417, (1996)). The catalytic properties and tissue patterns of expression of these selenoproteins differ from those of Dio2. Unlike Dio2, Dio1 is expressed in liver and kidney and is capable of inner ring deiodination of sulfated thyroid hormone conjugates. Dio3 functions as an inner ring deiodinase to convert T4 and T3 to inactive metabolites. Its expression in placenta and several fetal tissues during early development suggested that it plays a role in preventing premature exposure of developing tissues to adult levels of thyroid hormones. Dio2 also is present in several fetal and neonatal tissues and is essential for providing the brain with appropriate levels of T3 during the critical period of development.

Dio2 is upregulated 10- to 50-fold in brown adipose tissue in response to cold stress (See, e.g., de Jesus et al., J. Clin. Invst., 108, 1379 (2001)).

It has been shown that selenium depletion reduced the basal endogenous Dio2 expression and activity in a mesothelioma cell line (See, e.g., *J. Biol. Chem.* 276: 30183 (2002)). This depletion could be reversed by selenium supplementation in a dose- and time-dependent fashion. Dio2 expression and activity also increased following exposure to a nonhydrolyzable cAMP analog. Exposure to the thyroxine substrate increased the degradation of DIO2, resulting in decreased DIO2 activity. The short half-life of endogenous DIO2 (less than 1 hr) and the increased degradation of DIO2 in the presence of thyroxine were reduced or eliminated by exposure to proteasome inhibitors.

Experiments conducted using compositions and methods of the present invention provided that SeMet and Sod-sel displayed no ability to alter the expression levels of Dio2, while SEL-PLEX caused a significant, 2.3-fold down-regulation of this gene. Thus, the present invention provides a method of reducing stress (e.g., cellular stress) in a subject comprising providing to the subject a composition comprising selenium (e.g., SEL-PLEX) under conditions such that the expression of Dio2 is reduced. In some preferred embodiments, the present invention provides a method of stabilizing endocrine function in a subject comprising administering to the subject a composition comprising SEL-PLEX under conditions such that the expression of Dio2 is reduced.

Although an understanding of the mechanism is not necessary to practice the present invention and the present invention is not limited to any particular mechanism of action, in some embodiments, treating a subject with a composition comprising selenium (e.g., a dietary supplement comprising SEL-PLEX) reduces the expression of Dio2, thereby reducing cellular stress within the subject. Thus, the unique altering (e.g., reduction) of expression of Dio2 demonstrates that subjects receiving certain forms of selenium (e.g., SEL-PLEX) experience/are under less stress that those subject not receiving treatment.

The expression of several other stress-associated genes was uniquely altered (e.g., downregulated) by certain forms of selenium (e.g., expression altered by SEL-PLEX but not altered by treatment with SeM or Sod-sel). One example was the gene for Glyoxalase 1 (Glo1). Glyoxalase is the main detoxification pathway for methyl-glyoxal, a cytotoxic by-product of aerobic glycolysis (See, e.g., Amicarelli et al., Carcinogenesis, 19, 519 (1998)).

It has been shown that the Glo1 gene was upregulated approximately 1.6-fold in brain tissue of a transgenic mouse model of Alzheimer disease (AD) and frontotemporal dementia (See, e.g., Chen et al., Proc. Nat. Acad. Sci. 101: 7687 (2004)). GLO1 was also elevated in human Alzheimer disease brains compared to nondemented controls, and GLO1 immunohistochemistry detected intensely stained flame-shaped neurons in AD brains. Data demonstrated the potential of transcriptomics applied to animal models of human diseases and suggested a previously unidentified role for glyoxalase I in neurodegenerative disease (See, e.g., Chen et al., Proc. Nat. Acad. Sci. 101: 7687 (2004).

Experiments conducted using compositions and methods of the present invention provide that the expression levels of Glo1 were not significantly affected by SeMet or Sod-Sel. However, treatment (e.g., dietary supplementation) with SEL-PLEX resulted in a 1.3 fold reduction of expression ($p<0.01$). Accordingly, the present invention provides a method of treating a subject (e.g., an Alzheimer disease subject) comprising providing to the subject a composition comprising selenium (e.g., SEL-PLEX or derivatives thereof) under conditions such the expression of Glo1 in the subject is reduced.

The expression of growth arrest and DNA damage-inducible genes was also altered (e.g., reduced) by selenium supplementation (See, e.g., Table 2, below). Thus, in some embodiments, the present invention provides compositions (e.g., comprising SEL-PLEX) and methods that reduce DNA damage in a subject, as evidenced by the down-regulation of genes associated with DNA damage and growth arrest in subjects that received certain forms of selenium supplementation (e.g., SEL-PLEX). Thus, in some embodiments, the present invention provides a method of reducing DNA damage in a subject comprising providing to the subject a composition comprising selenium (e.g., SEL-PLEX) under conditions such that DNA damage is reduced.

TABLE 2

| Gene Title/Symbol | FC SM | FC SS | FC SP | Functional Class |
|---|---|---|---|---|
| Growth arrest and DNA-damage-inducible 45 beta. (Gadd45b) | NS | NS | $-1.3$ ($P < 0.05$) | Signal Transduction |
| Growth arrest and DNA-damage-inducible 45 gamma. (Gadd45g) | $-1.5$ ($p < 0.05$) | $-2.0$ ($p < 0.01$) | $-2.2$ ($p < 0.05$) | Stress response |
| P53 and DNA damage-regulated 1. (Pdrg1). | NS | NS | $-1.3$ ($P < 0.05$) | Stress response |

Another class of proteins whose expression was altered with selenium treatment is prohibitins. Prohibitins are proteins that have been ascribed various functions within the cell, including cell cycle regulation, involvement in apoptosis and assembly of mitochondrial respiratory chain enzymes. They are present in the inner mitochondrial membrane and their expression is known to be induced by metabolic stress caused by an imbalance in the synthesis of mitochondrial and nuclear-encoded mitochondrial proteins. Prohibitins act in cooperation with each other to modulate mitochondrial activity, particularly in situations of mitochondrial stress (See, e.g., Coates et al., Exp. Cell. Research, 265, 262 (2001)). Generally, with an increase in age, the is a concomitant increase in mitochaondrial stress.

Using compositions and methods of the present invention, it was observed that subjects treated with certain forms of selenium (e.g., SEL-PLEX) significantly downregulated the expression of Prohibitin (Phb) 1.3-fold ($p<0.05$), whereas Sod-sel did not significantly alter Phb expression and where SeM significantly upregulated Phb expression 1.6-fold ($p<0.05$). Thus, in some embodiments, the present invention provides a method of altering age associated expression of a prohibitin gene in a subject comprising administering to said subject a composition comprising SEL-PLEX under conditions such that age associated expression of a prohibitin gene is reduced. Although an understanding of the mechanism is not necessary to practice the present invention and the present invention is not limited to any particular mechanism of action, providing certain forms of selenium (e.g., SEL-PLEX) reduces mitochondrial stress associated with aging whereas other forms of selenium (e.g., selenomethionine) are incapable of reducing mitochondrial stress and may even increase it. Thus, this provides further support for the use of certain compositions comprising certain forms of selenium (e.g., SEL-PLEX) and not other types of selenium (e.g., SeM or Sod-sel) in order to reduce stress (oxidative or other forms) in a subject. Thus, in general, the present invention provides compositions comprising certain forms of selenium (e.g., SEL-PLEX) that, when administered (e.g., via a dietary supplement) to a subject, do not induce the expression of stress inducible genes that are induced by the administration of other forms of selenium (e.g., SeM and/or Sod-sel). Accordingly, in some embodiments, the present invention provides a method of reducing cellular stress (e.g., metabolic stress) in a subject comprising providing to the subject a composition comprising selenium (e.g., SEL-PLEX) under conditions such that the expression of Phb is reduced.

Example 5

Selective Forms of Dietary Selenium Alter Neuronal Gene Expression

Basal forebrain cholinergic neurons (BFCNs) are involved in cognitive functions such as learning and memory and are affected in several neurodegenerative diseases, such as Alzheimer's disease (AD). The LIM homeobox protein 8 gene (Lhx8), is important for the proper development and maintenance of BFCNs (See, e.g., Mori et al., Eur. J. Neurosci., 19, 3129 (2004)).

It has been reported that mice with a null mutation in the Lhx8 gene are deficient in the development of forebrain cholinergic neurons (Zhao et al., Proc. Nat. Acad. Sci. 100: 9005 (2003)). The Lhx8 mutants lacked the nucleus basalis, a major source of the cholinergic input to the cerebral cortex. In addition, the number of cholinergic neurons was reduced in several other areas of the subcortical forebrain in these mutants. Although cholinergic neurons were not formed, initial steps in their specification appeared to be preserved, as indicated by a presence of cells expressing a truncated Lhx8 mRNA and mRNA of the homeobox gene Gbx1. These results provide genetic evidence supporting an important role for Lhx8 in development of cholinergic neurons in the forebrain.

Using compositions and methods of the present invention, the observed expression level of Lhx8 was not significantly different between Se-deficient subjects and that of subjects receiving certain forms of selenium (e.g., SeM or Sod-sel). However, when subjects were treated (e.g., received a dietary supplement) with a composition comprising SEL-PLEX, the expression of Lhx8 was upregulated 12.9-fold ($p<0.01$). Thus, in some embodiments, the present invention provides methods of maintaining and/or stabilizing neurologic function (e.g., cholinergic neuron growth and function) in a subject comprising providing to the subject a composition comprising SEL-PLEX under conditions such that the expression of Lhx8 is enhanced.

In addition, the product of another gene, transforming growth factor beta 2 (TGF-$\beta$2), is known to increase neuronal proliferation in the developing cerebellum (See, e.g., Elvers et al., Mechanisms of Development, 122, 587 (2004)). Furthermore, it has been shown that TGF-$\beta$2 is a growth and survival factor for granule cell precursors in the cerebellum and that antibody-mediated neutralization of endogenous TGF-$\beta$2 represses proliferation of cerebellar granule cell precursors and induces neurodegeneration. It has also been demonstrated that knocking out (e.g., deleting) TGF-$\beta$2 is a lethal phenotype with TGF-$\beta$2 deficient mice developing a range of defects and dying before development of the cerebellum occurs (See, e.g., Sanford et al., Development, 124, 2659 (1997)).

Using compositions and methods of the present invention, the expression level of TGF-$\beta$2 was not altered, compared to controls, in subjects receiving certain forms of selenium (e.g., SeM or Sod-Sel). However, when subjects were treated (e.g., received a dietary supplement) with a composition comprising SEL-PLEX, the expression TGF-$\beta$ was upregulated 2.4-fold. Thus, in some embodiments, the present invention provides a method of increasing cerebellum function in a subject comprising providing to the subject a composition comprising SEL-PLEX. Although an understanding of the mechanism is not necessary to practice the present invention and the present invention is not limited to any particular mechanism of action, in some embodiments, providing a subject a composition comprising selenium (e.g., a daily dietary supplement comprising SEL-PLEX) increases neuronal activity (e.g., increases neuronal proliferation) and/or inhibits neurodegeneration (See, e.g., Example 10 below).

Example 6

Selective Forms of Dietary Selenium Alter the Expression of Diabetes Related Genes Neurogenin 3 (Neurog3) is a key transcription factor in the differentiation of the endocrine pancreas. Neurog3 is an important part of the activation pathway for insulin gene expression and helps to ameliorate glucose tolerance (See, e.g., Watada, Endocrine Journal, 51, 255 (2004)). It is thought that lower than normal levels (e.g., under-expression) of Neurog 3 plays a role in certain types of Diabetes (See, e.g., Lee et al., Genes Dev. 16: 1488 (2002)). Using compositions and methods of the present invention, it was determined that Neurog3 expression was significantly upregulated 1.7-fold in subjects receiving a composition comprising SEL-PLEX, whereas subjects that received SeM or Sod-sel treatments displayed no significant alteration of Neurog3 expression. Thus, in some embodiments, the present invention provides a method of treating a subject (e.g., a subject with diabetes) comprising administering to the subject a composition comprising SEL-PLEX under conditions such that the expression of Neurog3 is altered (e.g., enhanced) in the subject. Although an understanding of the mechanism is not necessary to practice the present invention and the present invention is not limited to any particular mechanism of action, in some embodiments, providing a subject with diabetes a composition comprising SEL-PLEX ameliorates glucose tolerance in the subject via up-regulating the expression of Neurog3 expression.

Example 7

Selective Forms of Dietary Selenium Up-Regulate the Expression of Genes Associated with Enhanced Respiratory System Function The *Drosophila* respiratory system and the mammalian lung are both formed by a process of branching morphogenesis, which depends on epithelial and mesenchymal interactions mediated by signaling between members of the fibroblast growth factor (FGF) family and their cognate receptors. Branchless, a *Drosophila* FGF homologue, is expressed in the tips of tracheal branches (See, e.g., Sutherland et al., Cell 87, 1091 (1996)). Branchless activates an FGF receptor homologue termed Breathless (See, e.g., Glazer and Shilo, Genes Dev 5, 697 (1991)), which directs tracheal cell migration as well as inducing secondary and terminal branches.

The sprouty gene (Spry2) product functions as an FGF antagonist in *Drosophila*: overexpression of sprouty blocks activation of downstream effectors in the Branchless pathway, whereas sprouty null mutation enhances the function of Branchless downstream genes, resulting in enhanced tracheal branching (See, e.g., Hacohen, et al., Cell 92, 253 (1998)). In *Drosophila* and mice, the product of the Spry2 gene has been demonstrated to negatively modulate respiratory organogenesis (See, e.g., Teftt et al., Current Biology, 9, 219 (1999)).

Using compositions and methods of the present invention, it was demonstrated that SEL-PLEX possessed a unique ability to downregulate the sprouty homolog 2 gene (Spry2). Specifically, subjects receiving a composition comprising SEL-PLEX displayed a significant reduction in Spry2 gene expression (1.7-fold reduction), while subjects receiving compositions comprising other forms of selenium (e.g., SeM or Sod-sel) displayed no alteration in expression levels of Spry2 relative to Se-deficient controls. Thus, the present invention provides a method of enhancing respiratory system function in a subject comprising providing to the subject a composition comprising selenium (e.g., SEL-PLEX). Although an understanding of the mechanism is not necessary to practice the present invention and the present invention is not limited to any particular mechanism of action, in some embodiments, treating a subject with a composition comprising selenium (e.g., SEL-PLEX) enhances respiratory system function via reducing Spry2 gene expression.

Example 8

Selective Forms of Dietary Selenium Alter the Expression of Genes Associated with Aging and Cognitive Function Aging is well known to be associated with increased oxidant generation (See, e.g., Peinado et al., Anat Rec, 247, 420 (1997)). For example, highly reactive oxygen species (ROS) promote a wide spectrum of cell damage, including DNA damage, lipid peroxidation, alteration of intracellular redox balance and inactivation of enzymes. A key host mechanism in the defense against ROS is performed by the family of Glutathione-S-Transferases (GSTs) that protect against the by-products of oxidative stress through a variety of reactions (See, e.g., Hayes et al., Annu. Rev. Phramacol. Toxicol., 45, 51, (2004)). In the area of neurodegeneration, oxidation of cathecholamines yields aminochrome, dopachrome, noradrenochrome and adrenochrome that are harmful because they can produce $O_2^-$ by redox cycling. These quinone-containing compounds can be conjugated with GSH through the actions of GSTs, a reaction that prevents redox cycling (See, e.g., Dagnino-Subiabre et al., Biochem. Biophys. Res. Commun., 274, 32 (2000)). O-quinones formed from dopamine can also be conjugated with GSH by GSTs, and this reaction is thought to combat degenerative processes in the dopaminergic system in the human brain (e.g., loss of the ability to combat this process may play a role in disease such as Parkinson's disease).

In microbes, plants, flies, fish and mammals, expression of GSTs is upregulated by exposure to pro-oxidants and, indeed, the promoter regions of cytosolic GSTs contain anti-oxidant response elements through which they are transcriptionally activated during exposure to Michael reaction acceptors and oxidative stress (See, e.g., Hayes et al., Annu. Rev. Phramacol. Toxicol., 45, 51, (2004)).

Thus, compositions and methods of the present invention were analyzed to determine if they were capable of altering the expression levels of GST genes. Compositions comprising various forms of selenium (e.g., SeM, Sod-sel, and SEL-PLEX) were administered to subjects and the expression levels of GST genes monitored. The expression level of several GST genes were altered by selenium supplementation compared with control subjects receiving Se-deficient diets (See Table 3, below).

| Gene name | Symbol | FC SeM | FC Sod-Sel | FC SEL-PLEX |
|---|---|---|---|---|
| Glutathione S-transferase, alpha 3 | Gsta3 | NS | −2.3 | −2.5 |
| Glutathione S-transferase, alpha 4 | Gsta4 | NS | NS | −1.7 |
| Glutathione S-transferase, mu1 | Gstm1 | NS | −2.4 | NS |
| Glutathione S-transferase, mu2 | Gstm2 | NS | −2.1 | −2.1 |
| Glutathione S-transferase, mu3 | Gstm3 | NS | −2.7 | −2.3 |
| Glutathione S-transferase, theta 1 | Gstt1 | NS | NS | −1.4 |
| Glutathione S-transferase, theta 2 | Gstt2 | NS | −1.3 | NS |

Surprisingly, subjects receiving free dietary selenomethionine (SeM) demonstrated no alteration in the expression pattern of these genes (e.g., the GST genes were not downregulated). However, subjects receiving Sod-sel and SEL-PLEX displayed an altered (e.g., reduced) expression of GST genes. Thus, the present invention provides that distinct differences exist in the ability of different selenium sources to elicit responses in the expression profiles of genes (e.g., GST genes and those described elsewhere herein).

Although an understanding of the mechanism is not necessary to practice the present invention and the present invention is not limited to any particular mechanism of action, in some embodiments, treating a subject with a composition comprising SEL-PLEX brings about less stress in the subject (e.g., provides lower oxidative stress levels), thereby permitting a general down-regulation of the expression of GST genes in subjects receiving SEL-PLEX. Accordingly, the present invention provides a method of reducing oxidative stress in a subject comprising providing to the subject a composition comprising selenium (e.g., SEL-PLEX or sod-sel) under conditions such that the expression of GST genes (e.g., Gstt2, Gstt1, Gsta3, Gsta4, Gstm1, Gstm2, or Gstm3) are reduced. In some embodiments, two or more different forms of selenium (e.g., SEL-PLEX and Sod-sel) are administered to a subject. In some embodiments, administering two of more forms of selenium provides an additive effect (e.g., provides an additive reduction of GST expression). In some embodiments, administering two of more forms of selenium provides a more than additive (e.g., synergistic) effect of reducing GST gene expression. In some embodiments, administering two of more forms of selenium to a subject does not negate the effect of either selenium source to reduce the expression of GST genes. In some embodiments, the present invention provides a method of treating a subject with Parkinson's disease comprising providing to the subject a composition comprising selenium (e.g., a dietary supplement comprising SEL-PLEX) under conditions such that the expression of GST genes ubiquitin genes are down-regulated.

In some embodiments, the present invention provides a method of retarding age-related progression (e.g., increase in oxidative stress levels) in a subject comprising providing to the subject a composition comprising selenium (e.g., a dietary supplement comprising SEL-PLEX). In other embodiments, the present invention provides a method of inhibiting neuronal degeneration (e.g., reducing oxidative stress that leads to or is causative of neuronal degeneration) in a subject comprising providing to the subject a composition comprising selenium (e.g., a dietary supplement comprising SEL-PLEX). Although an understanding of the mechanism is not necessary to practice the present invention and the present invention is not limited to any particular mechanism of action, in some embodiments, age-retardation and prevention of neurodegeneration is attained by treating a subject with a composition comprising selenium (e.g., a dietary supplement comprising SEL-PLEX) that leads to the down-regulation of stress induced genes (e.g., GST genes). Furthermore, the present invention demonstrates that certain forms of selenium (e.g., SEL-PLEX) are capable of altering various gene expression profiles in a subject that other forms of selenium (e.g., SeM and/or Sod-sel) are not. Thus, the present invention provides that, in some embodiments, SEL-PLEX is superior to other forms of selenium (e.g., SeM or Sod-sel) for use in nutritional interventions (e.g., for maintaining and prolonging optimal cognitive function and retarding agedness).

As described below, data demonstrating the selenium source dependent nature of gene expression alteration generated in intestinal tissue (e.g., See Examples 2-8 above) is also observed in other tissue (e.g., brain tissues). Additionally, as described in Example 9, below, certain forms of selenium (e.g., SEL-PLEX) demonstrates superior biological availability in terms of the amount of selenium deposited (e.g., in brain tissue) relative to a variety of other selenium sources.

Example 9

Effect of Various Selenium Sources on Brain Selenium Concentrations in White-Egg-Laying Hens and their Offspring Compositions and methods of the present invention were utilized to evaluate the effects of various Se sources on the accumulation of brain Se concentrations in hens and their offspring.

TABLE 5

| Chick Brain Se Concentration at day 14 | |
|---|---|
| Treatment | ppb |
| Basal | 786 |
| Selenite | 784 |
| SEL-PLEX | 995 |
| TepSel | 862 |
| Se 2000 | 884 |
| Selenosource | 872 |

The study was conducted at the Coldstream Research Facility from Jun. 28, 2004 until Nov. 16, 2004. Six dietary treatments were fed to a total of 48 hens (r=8) that were bred on three consecutive days starting on Sep. 16, 2004.
The dietary treatments were as follows:
Basal (no added Se)
Selenite (0.3 ppm)
Sel Plex (0.3 ppm)
Tepsel (0.3 ppm)
Se 2000 (0.3 ppm)
Selenosource (0.3 ppm)

Chicks that hatched were divided into two groups. Half of the chicks were killed for brain collection and the remaining chicks were allowed to grow for 14 days on a Se deficient diet, at which time they were terminated for brain collection. Hen brains were analyzed for Se content individually, whereas the chick brains were homogenized and pooled because of small sample size.

Brain Se concentrations for the hens and chicks are shown in Tables 4 and 5, below, respectively. The Selenosource value represents only one hen brain analyzed and therefore was not included in the statistical analysis.

Hens fed SEL-PLEX had the highest concentration of Se compared with all other treatments included in the model. No increase in brain Se content was observed due to any of the remaining treatments when compared with the basal treatment. The brain Se concentration in the chick brains represents the numerically highest among all treatments.

TABLE 4

| Hen Brain Se Concentration | | |
|---|---|---|
| Treatment | ppb | S.E. |
| 1. Basal | 870 | 46 |
| 2. Selenite | 850 | 65 |
| 3. SEL-PLEX | 1125 | 46 |
| 4. Tepsel | 825 | 55 |
| 5. Se2000 | 909 | 73 |
| 6. Selenosource | 1102* | NE |
| contrast | P = | |
| 1 vs. 3 | 0.0006 | |
| 3 vs. 5 | 0.0184 | |
| 2 vs. 3 | 0.0018 | |
| 3 vs. 4 | 0.0002 | |

*NE = Not estimated due to one sample
SE - standard error

Thus, in addition to being preferred for use in methods of the present invention (e.g., for altering gene expression profiles), compositions comprising SEL-PLEX also provide (e.g., when provided to a subject as a dietary supplement or through other means), when compared to equal consumption of other forms of selenium, the highest levels of bioavailable selenium (e.g., in brain tissue).

Example 10

Influences of Selective Forms of Dietary Selenium on Brain (e.g., Cerebral Cortex) Gene Expression Compositions and methods of the present invention were tested to determine whether they could play a role in altering the aging process (e.g., altering the level of gene expression known to be associated with aging). In general, subjects treated with compositions and methods of the present invention display gene expression profiles consistent with reversal or retardation of the aging process. For example, by comparing the gene expression profiles obtained with compositions and methods of the present invention, to the gene expression profiles obtained from the brain tissue of very old (e.g., 30-month old) mice (See, e.g., Lee, et al., Nature Genetics 25:294 (2000)), nearly opposite gene expression patterns were observed between the two cohorts.

For example, in aged animals, a concerted induction of the complement cascade genes C4, C1qa, C1qb and C1qc was observed (See, e.g., Lee, et al., Nature Genetics 25:294 (2000)).

The complement system is a complex cascade involving proteolytic cleavage of serum glycoproteins often activated by cell receptors. This cascade ultimately results in induction of the inflammatory response, phagocyte chemotaxis and opsonization, and cell lysis (See, e.g., Villiers et al., Crit Rev Immunol.; 24:465 (2004); Morgan et al., Immunol Lett. 97:171 (2005)).

Complement factors C3a, C5a and C4 can induce vasodilatation, increased capillary, permeability, and expression of leukocyte adhesion molecules. Complements C3a and C4b are opsonins that bridge phagocytes to microorganisms. Comlements C3a and C4a promote phagocyte chemotaxis. Complement C3b may be an opsonin for antgen-antibody complexes which helps prevent damage from the formation of large, insoluble immune aggregates. Complement C5a, like C3a is an anaphylatoxin, and is a chemotactic attractant for induction of neutrophilic release of antimicrobial proteases and oxygen radicals. A complex of complements C5b, C6, C7, and C8 mediates the polymerization of up to eighteen C9 molecules into a tube-like membrane attack complex that is inserted into the plasma membrane of an unwanted organisms such as of gram-negative bacteria and viral infected cells. This channel through the lipid bilayer results in lysis of the cell. Ischaemic infarction may also cause initiation of the complement cascade. Excessive deposits of membrane attack complexes in tissues may occur following ischaemic injury. Other deleterious effects of complement activation include, degranulation of neutrophils, basophils and mast cells, unwanted release of the neutrophil products elastase and oxygen radicals, and extracorporeal blood circulation. Complement inhibitors have been suggested as potential therapeuics for immune diseases and Alzheimer's disease.

Figure 2:
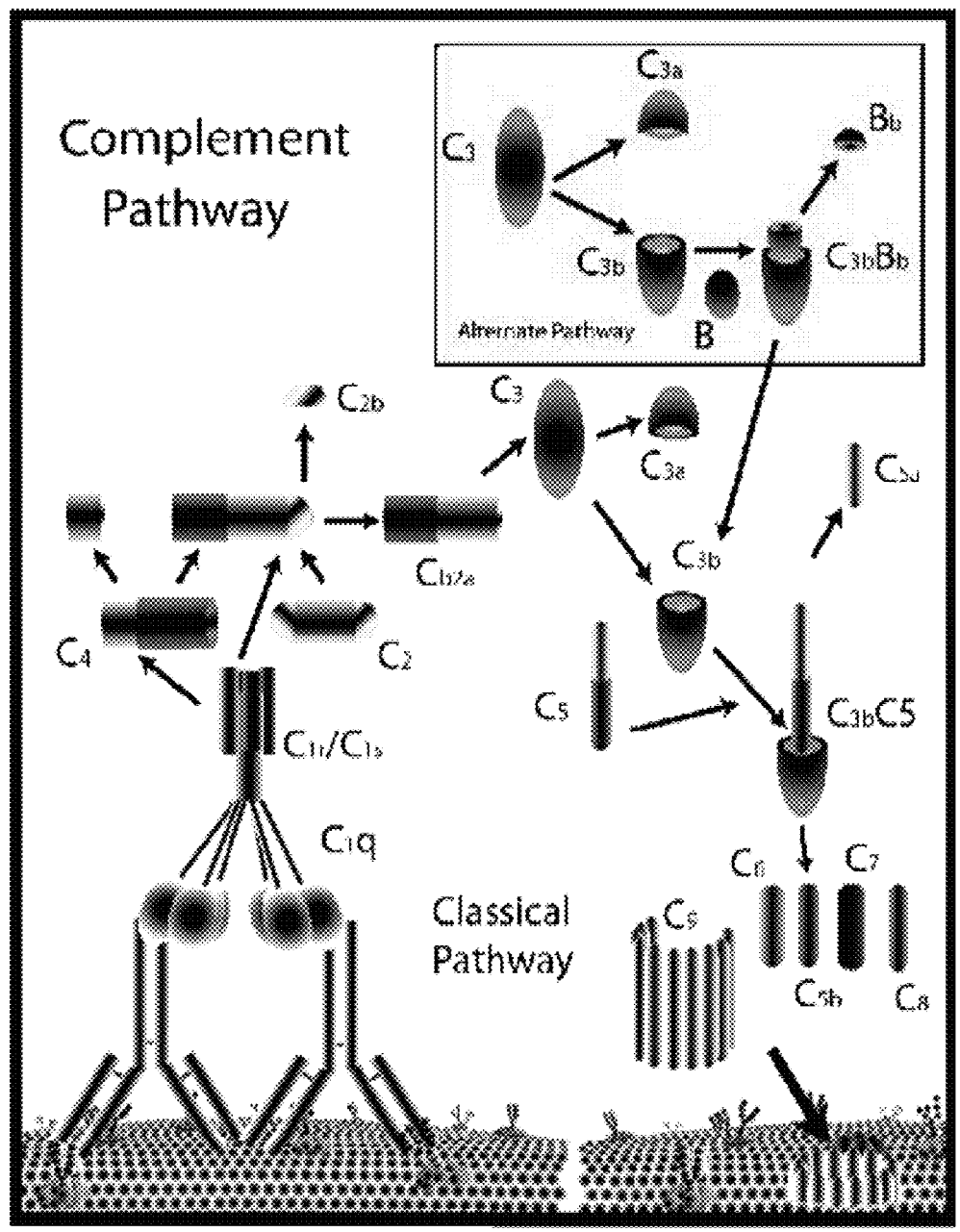
FIG. 2 depicts a cartoon of the complement cascade.
Figure 3:
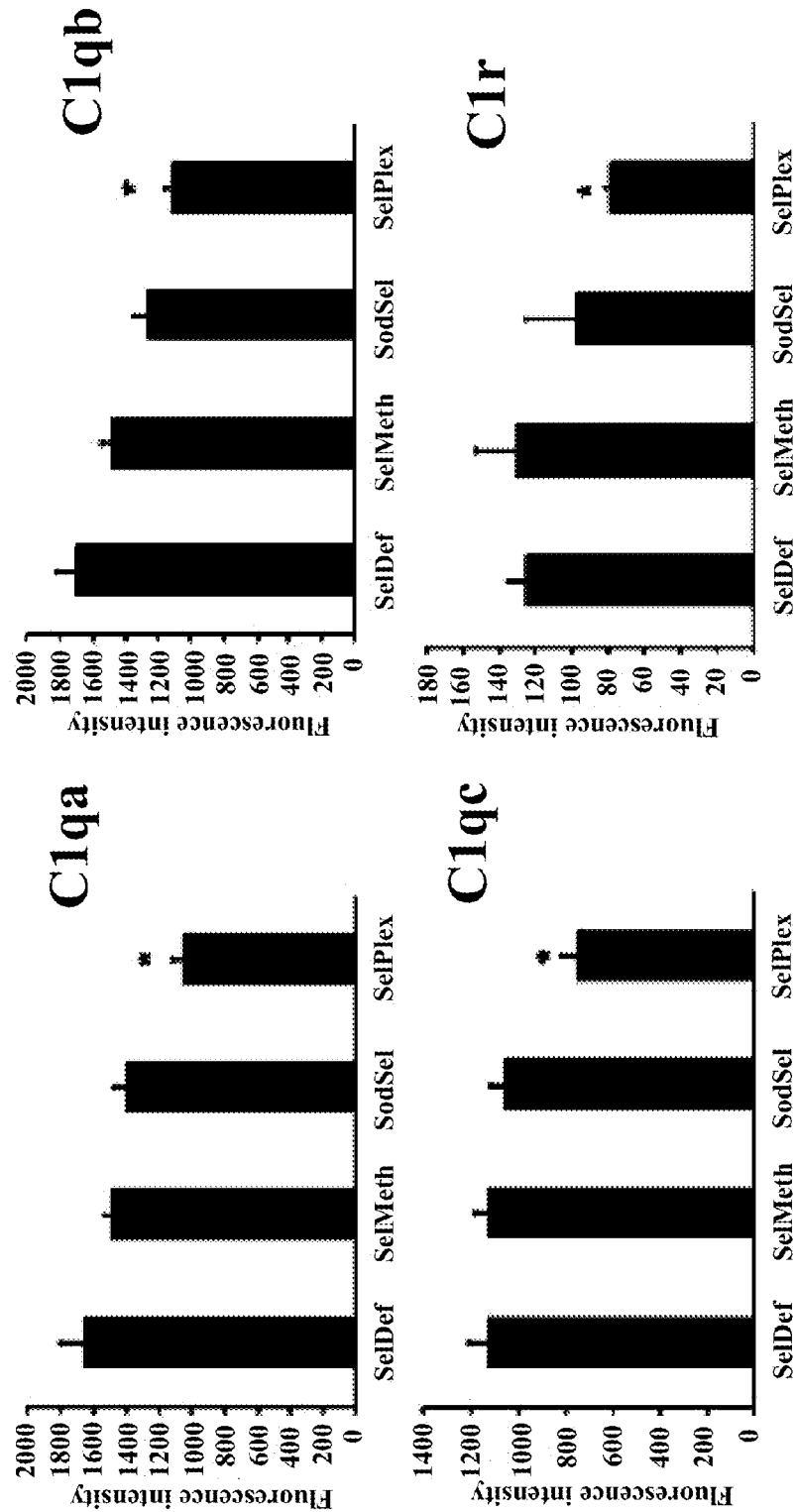
FIG. 3 shows that complement gene expression decreases after a subject is treated with a composition comprising selenium. (* indicates significant reduction, $p<0.01$).
Figure 4:
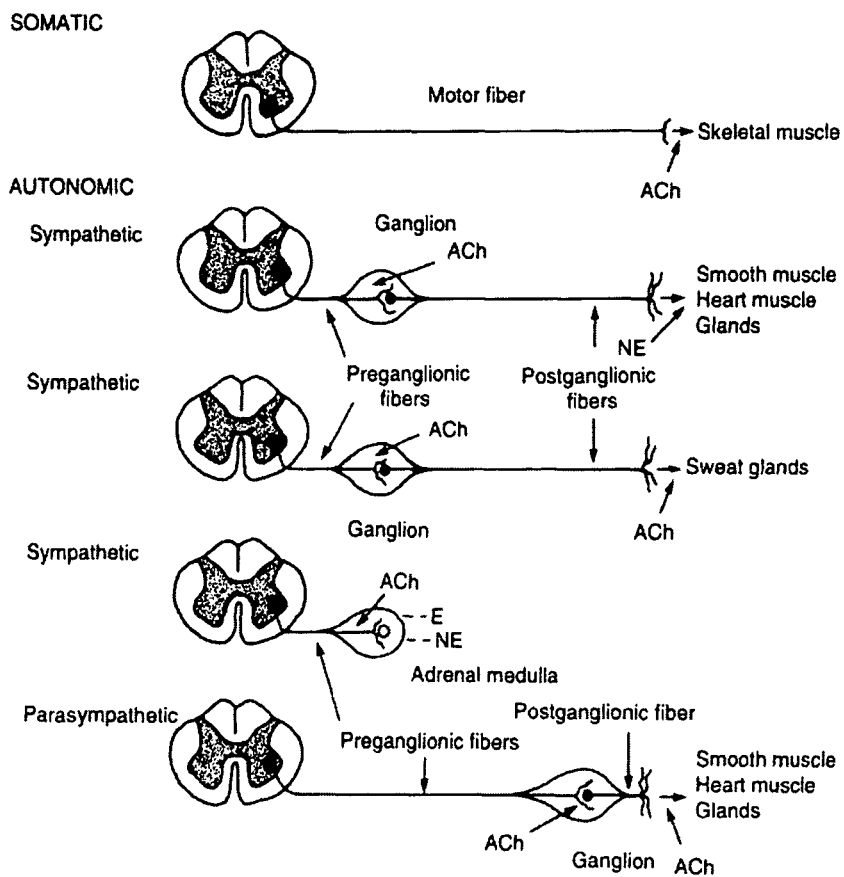
FIG. 4 depicts a cartoon of peripheral efferent nerves.

The Complement Pathways. Three pathways have been elucidated through which the complement cascade can be initiated; Classical, Alternate and Lectin Pathways. All three pathways merge through at common intersection, complement C3 (See, e.g., FIG. 2).

The Classical Pathway: The classical pathway mediates specific antibody responses. The classical pathway is initiated by the binding of antibodies to cell surface antigens. Subsequent binding of the antibody to complement C1q subunits of C1 result in catalytically active C1s subunits. The two activated C1s subunits are then able to catalyze the assembly of the C3 convertase (complement C4b2a) from complements C2 and C4.

The Alternate Pathway: The alternate pathway does not require the action of antibodies to inititate the cascade, but is initiated by foreign cell surface components. In the alternate pathway complement C3 undergoes spontaneous cleavage resulting in complement B binding to C3b. Diffusion of the Ba subunit results in an active alternate pathway C3 convertase (C3bBb). C3bBb is stabilized by binding to properdin prior to merging into the common pathway and conversion of C3.

The Lectin Pathway: The lectin pathway is similar to the classical pathway. C1q is not involved in the lectin pathway. Instead an opsonin, mannan binding protein (MBP), is involved in the initiation process.

Production of complement proteins in the brain leads to the generation of pro-inflammatory peptides and contributes to neuronal damage associated with stroke. Importantly, it has been documented that activated components of the complement pathway are associated with Alzheimer's disease (AD) lesions and other neurodegenerative disorders such as Multiple Sclerosis (See, e.g., Yasojima et al., Am. J. Pathology, 154, 927 (1999); Schwab and McGeer, Exp. Neurology, 174, 81 (2002)). Studies in AD brain have shown vigorous up-regulation of complement genes (e.g., mRNAs) and the appearance of strong bands in Western blots for complement activation products. The fold change in complement components in the brains of old mice versus young mice were as follows: Complement C4, up-regulated 4.9 fold; C1qa, up-regulated 1.7 fold; C1qb, up-regulated 1.8 fold; C1qc, up-regulated 1.8 fold (See, e.g., Lee, et al., Nature Genetics 25:294 (2000)).

Accordingly, it was determined whether compositions and methods of the present could alter the expression of complement genes in the cerebral cortex. The effects of selenium supplementation, using various sources of selenium, on the expression levels of genes encoding components of the complement system were as follows:

TABLE 6

| Gene | FC SeM | FC Sod-Sel | FC SEL-PLEX |
|---|---|---|---|
| Complement component 1, q subcomponent binding protein, C1qbp | 1.12 | 1.11 | −1.28* |
| Complement component 1, q subcomponent, alpha polypeptide, C1qa | −1.11 | −1.18 | −1.58* |
| Complement component 1, q subcomponent, beta polypeptide, C1qbp | −1.15 | −1.35 | −1.51* |
| Complement component 1, q subcomponent, gamma polypeptide, C1qg | 1.0 | −1.07 | −1.49* |
| Complement component 1, r subcomponent, C1r | 1.04 | −1.29 | −1.58* |

As illustrated in Table 6, above, compositions and methods of the present invention were able to alter the expression of various complement genes (e.g., that have been demonstrated to be aberrantly expressed in neurodegenerative diseases such as Alzheimer's disease). Specifically, a statistically significant down-regulation of complement component genes was brought about by selenium (e.g., SEL-PLEX, p<0.01, whereas providing subjects with compositions comprising SeM or Sod-sel did not provide a statistically significant alteration of complement component genes). The ability of selenium (e.g., SEL-PLEX) to reduce the expression of genes associated with the complement cascade produces gene expression profiles (e.g., reduced expression level) that are highly similar to that seen in multiple tissues of calorie-restricted (aging-retarded) mice (See, e.g., Sohal and Weindrich, Science, 273, 59 (1996)).

Accordingly, in some embodiments, the present invention provides a method of retarding age related expression of complement associated genes (e.g., C1q, C1q alpha, C1q beta, C1q gamma, and C1qr) in a subject comprising providing to the subject a composition comprising selenium (a dietary supplement comprising SEL-PLEX) under conditions such that complement associated gene expression is reduced. In some embodiments, the present invention provides a method of treating an Alzheimer's disease patient comprising providing to the Alzheimer's disease patient a composition comprising selenium (e.g., SEL-PLEX) under conditions such that symptoms of Alzheimer's disease in the patient are reduced. Although an understanding of the mechanism is not necessary to practice the present invention and the present invention is not limited to any particular mechanism of action, in some embodiments, providing a composition comprising selenium (e.g., SEL-PLEX) to an Alzheimer's subject reduces symptoms associated with Alzheimer's through reducing the expression of complement associated genes (e.g., C1q, C1q alpha, C1q beta, C1q gamma, and C1qr). In some embodiments, compositions and methods of the present invention are used as a prophylactic treatment in order to prevent the onset of Alzheimer's disease. In some embodiments, compositions and methods of the present invention are used in combination with other known therapeutic treatments for the treatment of neurologic disease (e.g., Alzheimer's disease). In other embodiments, compositions and methods of the present invention are used to prevent neurodegeneration (e.g., by inhibiting expression of complement associated genes, or inhibiting the expression of other genes described herein as having detrimental effects to cellular homeostasis, such as GST genes).

Compositions and methods of the present invention also altered the expression of a novel member of the TNF/C1 q/adiponectin superfamily, CORS-26. CORS-26 displays structural homolgies to adiponectin, which exerts proinflammatory and destructive properties in arthritic synovium (See, e.g., Tarner et al., Arthritis Res.& Therapy, 7, 23 (2005)). Subjects treated with certain forms of selenium (e.g., SeM and Sod-Sel) displayed no alteration in expression levels of CORS-26, whereas subjects that received a dietary supplement comprising other forms of selenium (e.g., SEL-PLEX) displayed a reduction in expression of 4.61 fold. Thus, in some embodiments, the present invention provides a method of treating arthritis in a subject comprising providing to the subject a composition comprising selenium (e.g., SEL-PLEX) under conditions such that symptoms associated with arthritis are reduced. Although an understanding of the mechanism is not necessary to practice the present invention and the present invention is not limited to any particular mechanism of action, in some embodiments, providing a composition comprising SEL-PLEX to a subject with arthritis reduces symptoms associated with arthritis by reducing CORS-26 gene expression.

Another class of genes that display a significant level of expression in aged mice compared to young mice are the cathepsins (e.g., cathepsins D, S and Z, See, e.g., Lee et al., Lee, et al., Nature Genetics 25:294 (2000)). Cathepsins are major components of the lysosomal proteolytic system and have been implicated in the processing of amyloid precursor protein (APP) to amyloid β-peptides. Importantly, they are induced in the brain of AD patients (See, e.g., Lemere et al., Am. J. Pathology, 146, 848 (1995)). Using compositions and methods of the present invention, the expression of genes encoding a number of cathepsins was downregulated in response to selenium supplementation, most notably by sodium selenite and SEL-PLEX (See Table 7, below).

TABLE 7

| Gene | FC SM | FC SS | FC SP |
| --- | --- | --- | --- |
| Cathepsin B | −1.03 | −1.13* | −1.16* |
| Cathepsin D | 1.02 | −1.24* | −1.29* |
| Cathepsin Z | −1.13 | −1.30* | −1.48* |
| Cathepsin O | −1.16 | −1.18 | −1.25* |

*downregulation significant relative to Se-deficient mice

It was further demonstrated that other genes involved in processing amyloid precursor protein (APP) were downregulated in response to selenium supplementation. One example is γ-secretase. The enzyme complex, γ-secretase cleaves APP resulting in the release of amyloid-β peptide, a principal component of AD plaques. Nicastrin is a transmembrane glycoprotein that interacts with presenilin, Aph-1 and Pen-2 to form the high molecular weight complex with γ-secretase activity (Confaloni et al., Molecular Brain Research, 136, 12 (2005)). The expression levels of the genes encoding nicastrin and presenilin were downregulated in response to treatment with certain compositions comprising selenium of the present invention (e.g., most notably, and significantly, by SEL-PLEX).

TABLE 8

| Gene | FC SM | FC SS | FC SP |
| --- | --- | --- | --- |
| Nicastrin | 1.04 | −1.67* | −1.7* |
| Presenilin 1 | 1.02 | −1.11 | −1.22* |

*Significant relative to Se-deficient animals. P < 0.01.

Furthermore, a number of genes involved in the generation of beta amyloid peptide were downregulated in response to treatment with compositions and methods of the present invention (e.g., selenium supplementation, See Table 9 below). For example, the amyloid beta (A4) precursor protein binding, family B, member 1 gene, (Apbb1/Fe65). Apbb1/Fe65 is an adaptor protein expressed mainly in the nervous system. APP is cleaved in the transmembrane region by γ-secretase. Gamma-cleavage of APP produces the extracellular amyloid beta peptide of Alzheimer disease and releases an intracellular tail fragment. It has been demonstrated that the cytoplasmic tail of APP forms a multimeric complex with the nuclear adaptor protein Fe65 and the histone acetyltransferase TIP60 (See, e.g., Cao and Sudhof, Science 293: 115 (2001)). Apbb1/Fe65 binds to APP and the interaction is mediated via a phosphotyrosine binding domain in Apbb1/Fe65 and the carboxy-terminal cytoplasmic domain of APP. Fe65 modulates trafficking and processing of APP, including production of the beta-amyloid peptide that is central to the pathogenesis of AD (See, e.g., Kesavapany et al., Neuroscience, 115, 951, (2002)).

TABLE 9

| Gene | FC SM | FC SS | FC SP |
| --- | --- | --- | --- |
| Amyloid beta (A4) precursor protein-binding, family B, member 1 (Apbb1 or Fe65) | 1.02 | −1.32* | −1.21* |
| Amyloid beta (A4) precursor-like protein (Aplp 1) | 1.02 | −1.55* | −1.45* |
| Amyloid beta (A4) precursor protein-binding, family A, member 1(Apba1) | 1.08 | −1.41 | −1.61* |

*Significant relative to Se-deficient animals. P < 0.01

Thus, in some embodiments, the present invention provides a method of treating an Alzheimer's disease patient comprising providing to the Alzheimer's disease patient a composition comprising selenium (e.g., SEL-PLEX) under conditions such that signs and symptoms of Alzheimer's disease in the patient are reduced. Although an understanding of the mechanism is not necessary to practice the present invention and the present invention is not limited to any particular mechanism of action, in some embodiments, providing a composition comprising selenium (e.g., SEL-PLEX) to an Alzheimer's subject reduces symptoms associated with Alzheimer's through reducing the expression of genes that encode proteins involved in processing amyloid precursor protein (APP) (e.g., Nicastrin, Presenilin 1, Cathepsin B, Cathepsin D, Cathepsin Z, or Cathepsin O) or genes involved in the generation of beta amyloid peptide (e.g., Apbb1, Aplp 1, and Apba1). In some embodiments, compositions and methods of the present invention are used as a prophylactic treatment in order to prevent the onset of Alzheimer's disease. In some embodiments, compositions and methods of the present invention are used in combination with other known therapeutic treatments for the treatment of neurodegenerative disease (e.g., Alzheimer's disease, Parkinson's disease, Huntington's disease, ALS, etc.). In other embodiments, compositions and methods of the present invention are used to prevent neurodegeneration (e.g., by inhibiting expression of genes that encode proteins involved in processing amyloid precursor protein or genes involved in the generation of beta amyloid peptide), conversely, enhancing expression of genes that provide a beneficial effect on cognitive function (e.g., Lhx8).

Studies in the aging mouse brain also identified the induced expression of early response genes, Junb and Fos, that are co-induced in response to neocortical injury or hypoxic stress (See, e.g., Lee, et al., Nature Genetics 25:294 (2000); Hermann et al., Neuroscience, 88, 599 (1999)). In neocortex, Junb was upregulated 1.8-fold. The present invention demonstrates that it is possible to down-regulate the expression of Junb using compositions and methods of the present invention. Specifically, the present invention provides that it is possible to down-regulate the expression of early response genes (e.g., Junb) in brain tissue (e.g., the neocortex) using compositions and methods (e.g., dietary supplementation with SEL-PLEX) of the present invention.

TABLE 10

| Gene | FC SM | FC SS | FC SP |
|------|-------|-------|-------|
| Junb | −1.38 | −1.59 | −2.01* |

*Significant relative to Se-deficient animals.

Similar to data generated in intestinal tissue, a downregulation in DNA-damage inducible genes was noted in response to treatment with compositions and methods of the present invention. For example, in intestinal tissue, a decreased expression was demonstrated for Gadd45b with SEL-PLEX treatments (p<0.05) and a decreased expression of Gadd45g1p for all selenium treatments (e.g., SeM, Sod-sel and SEL-PLEX) (p<0.05) was demonstrated. In brain, gene expression was altered using compositions and methods of the present invention as follows:

TABLE 12

| Gene | FC SM | FC SS | FC SP |
|------|-------|-------|-------|
| Gadd45b | −1.26 | −1.39* | −1.48 |
| Gadd45g1p (Growth arrest and DNA-damage inducible 45 gamma interacting protein | 1.02 | −1.12 | −1.37* |

*Significant relative to Se-deficient animals.

Other similarities between intestinal and brain data were noted in the area of Glutathione-S-Transferase (GST) expression. For example. in intestine, a decreased expression of the GST genes, Gsta3, Gsta4 and Gstm3 was demonstrated in the Sod-sel and SEL-PLEX groups (p<0.05). In brain, gene expression of a number of other GST genes was altered using compositions and methods of the present invention as follows:

TABLE 12

| Gene | FC SM | FC SS | FC SP |
|------|-------|-------|-------|
| Gst pi 1 (Gstp1) | −1.04 | 1.02 | −1.14* |
| Gst zeta 1 (Gstz1) | −1.08 | −1.3 | −1.41* |
| Gst mu 7 (Gstm7) | −1.05 | −1.25* | −1.24* |

*Significant relative to Se-deficient animals.

Thus, the present invention provides a method of protecting against the by-products of oxidative stress in brain tissue comprising providing to a subject a composition comprising selenium (e.g., SEL-PLEX). Although an understanding of the mechanism is not necessary to practice the present invention and the present invention is not limited to any particular mechanism of action, in some embodiments, providing a composition comprising selenium (e.g., SEL-PLEX) to a subject reduces the expression of GST genes (e.g., Gstp1, Gstz1, and Gstm7) in the subject. In some embodiments, providing a composition comprising selenium (e.g., SEL-PLEX) to a subject reduces the level of DNA damage in brain tissue (e.g., neocortex) of a subject. Although an understanding of the mechanism is not necessary to practice the present invention and the present invention is not limited to any particular mechanism of action, in some embodiments, treatment with compositions and methods of the present invention (e.g., dietary supplementation with SEL-PLEX) stabilizes cellular homeostasis (e.g., in the brain) such that the expression of DNA-damage inducible genes (e.g., Gadd45g1p) is reduced.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method of upregulating expression of Neurogenin 3 in a selenium-deficient subject comprising:
    orally administering an effective amount of a composition comprising a dried, nonviable selenium-enriched yeast wherein the total selenium content of said yeast comprises two percent or less inorganic selenium to said subject, wherein the effective amount is an amount that upregulates expression of Neurogenin 3 in said subject as compared to an untreated subject.

2. The method of claim 1, further comprising characterizing the expression level of Neurogenin 3 in said subject both prior to and subsequent to administering the composition.

3. The method of claim 1, further comprising characterizing the expression level of Neurogenin 3 in said subject prior to administering the composition.

4. The method of claim 1, further comprising characterizing the expression level of Neurogenin 3 in said subject subsequent to administering the composition.

5. The method of claim 1, wherein the effective amount of the composition comprises administering to the subject between about 50 µg to about 5000 µg of selenium per day.

6. The method of claim 1, wherein administering the composition comprises administering to the subject about 200 μg to about 500 μg selenium per day.

* * * * *